(12) United States Patent
Reitsamer et al.

(10) Patent No.: US 10,085,884 B2
(45) Date of Patent: *Oct. 2, 2018

(54) INTRAOCULAR DEVICES

(71) Applicant: AqueSys, Inc., Aliso Viejo, CA (US)

(72) Inventors: Herbert A. Reitsamer, Salzburg (AT); Guenther Grabner, Salzburg (AT); Christopher Horvath, Mission Viejo, CA (US); Laszlo O. Romoda, San Clemente, CA (US)

(73) Assignee: AQUESYS, INC., Aliso Viejo, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 14/313,970

(22) Filed: Jun. 24, 2014

(65) Prior Publication Data

US 2015/0011926 A1 Jan. 8, 2015

Related U.S. Application Data

(63) Continuation-in-part of application No. 12/946,572, filed on Nov. 15, 2010, now Pat. No. 8,852,256, and a continuation-in-part of application No. 12/946,222, filed on Nov. 15, 2010, now abandoned, and a continuation-in-part of application No. 12/946,240, filed on Nov. 15, 2010, now Pat. No. 8,828,070, and a continuation-in-part of application No. 12/946,251, filed on Nov. 15, 2010, now Pat. No. 9,095,411, and a continuation-in-part of application No. 12/946,263, filed on Nov. 15, 2010, now Pat. No. 8,801,766, and a continuation-in-part of application No. 13/314,927, filed on Dec. 8, 2011, now abandoned, which is a continuation-in-part of application No. 12/946,351, (Continued)

(51) Int. Cl.
*A61F 2/06* (2013.01)
*A61F 9/007* (2006.01)

(52) U.S. Cl.
CPC .............. *A61F 9/00781* (2013.01)

(58) Field of Classification Search
CPC ... A61F 9/00781; A61F 9/007; A61M 27/002; A61B 2017/00292; A61B 2017/00336
USPC ......................... 606/108; 623/6.12
See application file for complete search history.

(56) References Cited

U.S. PATENT DOCUMENTS 3,788,327 A 1/1974 Donowitz et al.
3,960,150 A 6/1976 Hussain et al.
(Continued)

FOREIGN PATENT DOCUMENTS

GB 2 296 663 A 7/1996
RU 2313315 C2 12/2007
(Continued)

OTHER PUBLICATIONS

U.S. Appl. No. 14/263,957 which has been allowed but not yet published.*

(Continued)

*Primary Examiner* — Melanie Tyson
(74) *Attorney, Agent, or Firm* — Nathan S. Smith; McDermott Will & Emery LLP

(57) ABSTRACT

Glaucoma can be treated by implanting an intraocular shunt into the eye. Such procedures can employ various deployment devices, shunts, and implantation techniques.

23 Claims, 56 Drawing Sheets

Related U.S. Application Data filed on Nov. 15, 2010, now abandoned, and a continuation-in-part of application No. 11/771,805, filed on Jun. 29, 2007, now abandoned, application No. 14/313,970, which is a continuation-in-part of application No. 12/946,556, filed on Nov. 15, 2010, now abandoned, and a continuation-in-part of application No. 14/263,957, filed on Apr. 28, 2014, now Pat. No. 9,283,116, which is a continuation of application No. 12/946,645, filed on Nov. 15, 2010, now Pat. No. 8,721,702, application No. 14/313,970, which is a continuation-in-part of application No. 14/191,340, filed on Feb. 26, 2014, now Pat. No. 9,192,516, which is a continuation of application No. 12/946,653, filed on Nov. 15, 2010, now Pat. No. 8,663,303, application No. 14/313,970, which is a continuation-in-part of application No. 12/946,565, filed on Nov. 15, 2010, now Pat. No. 8,974,511, and a continuation-in-part of application No. 13/336,758, filed on Dec. 23, 2011, now Pat. No. 8,852,137, which is a continuation-in-part of application No. 12/946,351, filed on Nov. 15, 2010, now abandoned, and a continuation-in-part of application No. 12/946,222, filed on Nov. 15, 2010, now abandoned, application No. 14/313,970, which is a continuation-in-part of application No. 13/336,803, filed on Dec. 23, 2011, now Pat. No. 8,758,290, which is a continuation-in-part of application No. 12/946,351, filed on Nov. 15, 2010, now abandoned, and a continuation-in-part of application No. 12/946,222, filed on Nov. 15, 2010, now abandoned, application No. 14/313,970, which is a continuation-in-part of application No. 13/895,170, filed on May 15, 2013, now Pat. No. 9,326,891, which is a continuation of application No. PCT/US2011/060820, filed on Nov. 15, 2011, which is a continuation of application No. 12/946,210, filed on Nov. 15, 2010, now Pat. No. 8,308,701, application No. 14/313,970, which is a continuation-in-part of application No. 13/952,543, filed on Jul. 26, 2013, now Pat. No. 9,017,276, which is a continuation of application No. 12/946,542, filed on Nov. 15, 2010, now abandoned.

(60) Provisional application No. 60/806,402, filed on Jun. 30, 2006.

(56) References Cited

U.S. PATENT DOCUMENTS

| | | | |
|---|---|---|---|
| 4,090,530 A | 5/1978 | Lange | |
| 4,402,308 A * | 9/1983 | Scott | A61B 17/3468 600/7 |
| 4,562,463 A | 12/1985 | Lipton | |
| 4,583,117 A | 4/1986 | Lipton et al. | |
| 4,700,692 A * | 10/1987 | Baumgartner | A61M 37/0069 600/7 |
| 4,722,724 A | 2/1988 | Schocket | |
| 4,744,362 A | 5/1988 | Grundler | |
| 4,750,901 A | 6/1988 | Molteno | |
| 4,787,885 A | 11/1988 | Binder | |
| 4,804,382 A | 2/1989 | Turina et al. | |
| 4,820,626 A | 4/1989 | Williams et al. | |
| 4,826,478 A | 5/1989 | Schocket | |
| 4,836,201 A | 6/1989 | Patton et al. | |
| 4,848,340 A | 7/1989 | Bille et al. | |
| 4,863,457 A | 9/1989 | Lee | |
| 4,902,292 A | 2/1990 | Joseph | |
| 4,911,161 A | 3/1990 | Schechter | |
| 4,915,684 A | 4/1990 | MacKeen et al. | |
| 4,934,363 A | 6/1990 | Smith et al. | |
| 4,936,825 A | 6/1990 | Ungerleider | |
| 4,946,436 A | 8/1990 | Smith | |
| 4,968,296 A | 11/1990 | Ritch et al. | |
| 4,978,352 A | 12/1990 | Fedorov et al. | |
| 5,041,081 A | 8/1991 | Odrich | |
| 5,057,098 A | 10/1991 | Zelman | |
| 5,071,408 A | 12/1991 | Ahmed | |
| 5,092,837 A | 3/1992 | Ritch et al. | |
| 5,098,426 A | 3/1992 | Sklar et al. | |
| 5,098,443 A | 3/1992 | Parel et al. | |
| 5,162,641 A | 11/1992 | Fountain | |
| 5,178,604 A | 1/1993 | Baerveldt et al. | |
| 5,180,362 A * | 1/1993 | Worst | A61F 9/00781 604/164.06 |
| 5,201,750 A | 4/1993 | Hocherl et al. | |
| 5,207,660 A | 5/1993 | Lincoff | |
| 5,275,622 A | 1/1994 | Lazarus et al. | |
| 5,290,295 A | 3/1994 | Querals et al. | |
| 5,300,020 A | 4/1994 | L'Esperance, Jr. | |
| 5,333,619 A | 8/1994 | Burgio | |
| 5,338,291 A | 8/1994 | Speckman et al. | |
| 5,342,370 A | 8/1994 | Simon et al. | |
| 5,360,339 A | 11/1994 | Rosenberg | |
| 5,368,015 A | 11/1994 | Wilk | |
| 5,370,607 A | 12/1994 | Memmen | |
| 5,399,951 A | 3/1995 | Lavallee et al. | |
| 5,410,638 A | 4/1995 | Colgate et al. | |
| 5,443,505 A | 8/1995 | Wong et al. | |
| 5,476,445 A | 12/1995 | Baerveldt et al. | |
| 5,516,522 A | 5/1996 | Peyman et al. | |
| 5,520,631 A | 5/1996 | Nordquist et al. | |
| 5,558,629 A | 9/1996 | Baerveldt et al. | |
| 5,558,630 A | 9/1996 | Fisher | |
| 5,601,094 A | 2/1997 | Reiss | |
| 5,656,026 A | 8/1997 | Joseph | |
| 5,665,093 A | 9/1997 | Atkins et al. | |
| 5,665,114 A | 9/1997 | Weadock et al. | |
| 5,670,161 A | 9/1997 | Healy et al. | |
| 5,688,562 A | 11/1997 | Hsiung | |
| 5,695,474 A | 12/1997 | Daugherty | |
| 5,704,907 A | 1/1998 | Nordquist et al. | |
| 5,707,376 A | 1/1998 | Kavteladze et al. | |
| 5,722,948 A | 3/1998 | Gross | |
| 5,763,491 A | 6/1998 | Brandt et al. | |
| 5,868,697 A | 2/1999 | Richter et al. | |
| 5,908,449 A | 6/1999 | Bruchman et al. | |
| 5,932,299 A | 8/1999 | Katoot | |
| 5,938,583 A * | 8/1999 | Grimm | A61M 37/0069 600/1 |
| 5,964,747 A | 10/1999 | Eaton | |
| 6,007,511 A | 12/1999 | Prywes | |
| 6,007,578 A | 12/1999 | Schachar | |
| 6,050,970 A | 4/2000 | Baerveldt | |
| 6,086,543 A | 7/2000 | Anderson et al. | |
| 6,102,045 A | 8/2000 | Nordquist et al. | |
| 6,146,366 A | 11/2000 | Schachar | |
| 6,159,218 A | 12/2000 | Aramant et al. | |
| 6,165,210 A | 12/2000 | Lau et al. | |
| 6,203,513 B1 | 3/2001 | Yaron et al. | |
| 6,228,023 B1 | 5/2001 | Zaslaysky et al. | |
| 6,228,873 B1 | 5/2001 | Brandt et al. | |
| 6,261,256 B1 | 7/2001 | Ahmed | |
| 6,264,665 B1 | 7/2001 | Yu et al. | |
| 6,280,468 B1 | 8/2001 | Schachar | |
| 6,413,540 B1 | 7/2002 | Yaacobi | |
| 6,450,937 B1 | 9/2002 | Mercereau et al. | |
| 6,471,666 B1 | 10/2002 | Odrich | |
| 6,483,930 B1 | 11/2002 | Musgrave et al. | |
| 6,514,238 B1 | 2/2003 | Hughes | |
| 6,524,275 B1 | 2/2003 | Lynch et al. | |
| 6,533,768 B1 | 3/2003 | Hill | |
| 6,544,249 B1 | 4/2003 | Yu et al. | |
| 6,558,342 B1 | 5/2003 | Yaron et al. | |
| 6,595,945 B2 | 7/2003 | Brown | |
| 6,638,239 B1 | 10/2003 | Bergheim et al. | |
| 6,699,210 B2 | 3/2004 | Williams et al. | |
| 6,726,664 B2 | 4/2004 | Yaron et al. | |
| D490,152 S | 5/2004 | Myall et al. | |

(56) References Cited

U.S. PATENT DOCUMENTS

| | | | |
|---|---|---|---|
| 6,736,791 B1 | 5/2004 | Tu et al. | |
| 6,752,753 B1* | 6/2004 | Hoskins | A61M 37/0069 600/7 |
| 6,881,198 B2 | 4/2005 | Brown | |
| 6,936,053 B1 | 8/2005 | Weiss | |
| 6,939,298 B2 | 9/2005 | Brown et al. | |
| 7,008,396 B1 | 3/2006 | Straub | |
| 7,037,335 B2 | 5/2006 | Freeman et al. | |
| 7,041,077 B2 | 5/2006 | Shields | |
| 7,094,225 B2 | 8/2006 | Tu et al. | |
| 7,118,547 B2 | 10/2006 | Dahan | |
| 7,135,009 B2 | 11/2006 | Tu et al. | |
| 7,163,543 B2 | 1/2007 | Smedley et al. | |
| 7,186,232 B1 | 3/2007 | Smedley et al. | |
| 7,207,980 B2 | 4/2007 | Christian et al. | |
| 7,291,125 B2 | 11/2007 | Coroneo | |
| 7,331,984 B2 | 2/2008 | Tu et al. | |
| 7,431,709 B2 | 10/2008 | Pinchuk et al. | |
| 7,431,710 B2 | 10/2008 | Tu et al. | |
| 7,458,953 B2 | 12/2008 | Peyman | |
| 7,488,303 B1 | 2/2009 | Haffner et al. | |
| 7,594,899 B2 | 9/2009 | Pinchuk et al. | |
| 7,625,384 B2 | 12/2009 | Eriksson et al. | |
| 7,708,711 B2 | 5/2010 | Tu et al. | |
| 7,837,644 B2 | 11/2010 | Pinchuk et al. | |
| 7,867,186 B2 | 1/2011 | Haffner et al. | |
| 8,109,896 B2 | 2/2012 | Nissan et al. | |
| 8,267,882 B2 | 9/2012 | Euteneuer et al. | |
| 8,277,437 B2 | 10/2012 | Saal et al. | |
| 8,308,701 B2 | 11/2012 | Horvath et al. | |
| 8,313,454 B2 | 11/2012 | Yaron et al. | |
| 8,337,393 B2 | 12/2012 | Silvestrini et al. | |
| 8,337,509 B2 | 12/2012 | Schieber et al. | |
| 8,377,122 B2 | 2/2013 | Silvestrini et al. | |
| 8,425,449 B2 | 4/2013 | Wardle et al. | |
| 8,444,589 B2 | 5/2013 | Silvestrini | |
| 8,486,000 B2 | 7/2013 | Coroneo | |
| 8,506,515 B2 | 8/2013 | Burns et al. | |
| 8,512,404 B2 | 8/2013 | Frion et al. | |
| 8,529,492 B2 | 9/2013 | Clauson et al. | |
| 8,535,333 B2 | 9/2013 | de Juan, Jr. et al. | |
| 8,545,430 B2 | 10/2013 | Silvestrini | |
| 8,585,629 B2* | 11/2013 | Grabner | A61F 9/0008 604/181 |
| 8,663,303 B2 | 3/2014 | Horvath et al. | |
| 8,721,702 B2* | 5/2014 | Romoda | A61F 9/00781 604/8 |
| 8,758,290 B2 | 6/2014 | Horvath et al. | |
| 8,765,210 B2 | 7/2014 | Romoda et al. | |
| 8,801,766 B2* | 8/2014 | Reitsamer | A61F 9/0008 623/1.11 |
| 8,828,070 B2* | 9/2014 | Romoda | A61F 9/0008 606/108 |
| 8,852,136 B2 | 10/2014 | Horvath et al. | |
| 8,852,137 B2 | 10/2014 | Horvath et al. | |
| 8,852,256 B2 | 10/2014 | Horvath et al. | |
| 8,974,511 B2 | 3/2015 | Horvath et al. | |
| 9,017,276 B2 | 4/2015 | Horvath et al. | |
| 9,095,411 B2* | 8/2015 | Horvath | A61F 9/00781 |
| 9,095,413 B2 | 8/2015 | Romoda et al. | |
| 9,192,516 B2 | 11/2015 | Horvath et al. | |
| 9,271,869 B2 | 3/2016 | Horvath et al. | |
| 9,283,116 B2* | 3/2016 | Romoda | A61F 9/00781 |
| 9,326,891 B2 | 5/2016 | Horvath et al. | |
| 9,393,153 B2 | 7/2016 | Horvath | |
| 2001/0025150 A1 | 9/2001 | De Juan, Jr. et al. | |
| 2001/0056254 A1 | 12/2001 | Cragg et al. | |
| 2002/0099434 A1 | 7/2002 | Buscemi et al. | |
| 2002/0133168 A1 | 9/2002 | Smedley et al. | |
| 2003/0015203 A1 | 1/2003 | Makower et al. | |
| 2003/0050574 A1 | 3/2003 | Krueger | |
| 2003/0060752 A1 | 3/2003 | Bergheim et al. | |
| 2003/0093084 A1 | 5/2003 | Nissan et al. | |
| 2003/0097053 A1 | 5/2003 | Itoh | |
| 2003/0187383 A1 | 10/2003 | Weber et al. | |
| 2003/0236483 A1 | 12/2003 | Ren | |
| 2003/0236484 A1 | 12/2003 | Lynch et al. | |
| 2004/0077987 A1 | 4/2004 | Rapacki et al. | |
| 2004/0147870 A1 | 7/2004 | Burns et al. | |
| 2004/0199130 A1 | 10/2004 | Chornenky et al. | |
| 2004/0210209 A1 | 10/2004 | Yeung et al. | |
| 2004/0215133 A1 | 10/2004 | Weber et al. | |
| 2004/0216749 A1 | 11/2004 | Tu | |
| 2004/0236343 A1 | 11/2004 | Taylor et al. | |
| 2004/0254521 A1 | 12/2004 | Simon | |
| 2004/0260227 A1 | 12/2004 | Lisk, Jr. et al. | |
| 2005/0049578 A1 | 3/2005 | Tu et al. | |
| 2005/0101967 A1 | 5/2005 | Weber | |
| 2005/0143363 A1 | 6/2005 | De Juan et al. | |
| 2005/0246023 A1 | 11/2005 | Yeung | |
| 2005/0267398 A1 | 12/2005 | Protopsaltis et al. | |
| 2005/0271704 A1 | 12/2005 | Tu et al. | |
| 2005/0277864 A1 | 12/2005 | Haffner et al. | |
| 2006/0052721 A1 | 3/2006 | Dunker et al. | |
| 2006/0064112 A1 | 3/2006 | Perez | |
| 2006/0106370 A1 | 5/2006 | Baerveldt et al. | |
| 2006/0116605 A1* | 6/2006 | Nakao | A61B 10/0266 600/566 |
| 2006/0116625 A1 | 6/2006 | Renati et al. | |
| 2006/0149194 A1 | 7/2006 | Conston et al. | |
| 2006/0155238 A1 | 7/2006 | Shields | |
| 2006/0173397 A1 | 8/2006 | Tu et al. | |
| 2006/0173446 A1 | 8/2006 | Dacquay et al. | |
| 2006/0200113 A1 | 9/2006 | Haffner et al. | |
| 2006/0229633 A1* | 10/2006 | Shepherd | A61F 2/1667 606/107 |
| 2006/0241411 A1* | 10/2006 | Field | A61B 19/54 600/431 |
| 2007/0093783 A1 | 4/2007 | Kugler et al. | |
| 2007/0118065 A1* | 5/2007 | Pinchuk | A61F 9/00781 604/9 |
| 2007/0141116 A1 | 6/2007 | Pinchuk et al. | |
| 2007/0172903 A1 | 7/2007 | Toner et al. | |
| 2007/0191863 A1 | 8/2007 | de Juan, Jr. et al. | |
| 2007/0202186 A1 | 8/2007 | Yamamoto et al. | |
| 2007/0263172 A1 | 11/2007 | Mura | |
| 2007/0293872 A1 | 12/2007 | Peyman | |
| 2008/0015633 A1* | 1/2008 | Abbott | A61B 17/0057 606/207 |
| 2008/0057106 A1 | 3/2008 | Erickson et al. | |
| 2008/0108933 A1* | 5/2008 | Yu | A61M 27/008 604/8 |
| 2008/0147001 A1 | 6/2008 | Al-Marashi et al. | |
| 2008/0181929 A1 | 7/2008 | Robinson et al. | |
| 2008/0249467 A1 | 10/2008 | Burnett et al. | |
| 2008/0281277 A1 | 11/2008 | Thyzel | |
| 2008/0312661 A1* | 12/2008 | Downer | A61F 2/1678 606/107 |
| 2009/0036818 A1 | 2/2009 | Grahn et al. | |
| 2009/0043321 A1 | 2/2009 | Conston et al. | |
| 2009/0124973 A1 | 5/2009 | D'Agostino et al. | |
| 2009/0182421 A1 | 7/2009 | Silvestrini et al. | |
| 2009/0209910 A1 | 8/2009 | Kugler et al. | |
| 2009/0216106 A1 | 8/2009 | Takii | |
| 2009/0264813 A1 | 10/2009 | Chang | |
| 2009/0270890 A1 | 10/2009 | Robinson et al. | |
| 2009/0281520 A1 | 11/2009 | Highley et al. | |
| 2009/0287136 A1 | 11/2009 | Castillejos | |
| 2010/0004581 A1 | 1/2010 | Brigatti et al. | |
| 2010/0063478 A1 | 3/2010 | Selkee | |
| 2010/0098772 A1 | 4/2010 | Robinson et al. | |
| 2010/0100104 A1 | 4/2010 | Yu et al. | |
| 2010/0119696 A1 | 5/2010 | Yu et al. | |
| 2010/0121248 A1 | 5/2010 | Yu et al. | |
| 2010/0121249 A1 | 5/2010 | Yu et al. | |
| 2010/0134759 A1 | 6/2010 | Silvestrini et al. | |
| 2010/0137981 A1 | 6/2010 | Silvestrini et al. | |
| 2010/0173866 A1 | 7/2010 | Hee et al. | |
| 2010/0191103 A1 | 7/2010 | Stamper et al. | |
| 2010/0249691 A1 | 9/2010 | Van Der Mooren et al. | |
| 2010/0328606 A1 | 12/2010 | Peyman | |
| 2011/0009874 A1 | 1/2011 | Wardle et al. | |
| 2011/0046536 A1 | 2/2011 | Stegmann et al. | |

(56) References Cited

U.S. PATENT DOCUMENTS

| | | |
|---|---|---|
| 2011/0098627 A1 | 4/2011 | Wilcox |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0226150 A1 | 9/2012 | Balicki et al. |
| 2012/0310137 A1 | 12/2012 | Silvestrini |
| 2013/0149429 A1 | 6/2013 | Romoda et al. |
| 2013/0150770 A1 | 6/2013 | Horvath et al. |
| 2013/0158462 A1 | 6/2013 | Wardle et al. |
| 2013/0184631 A1 | 7/2013 | Pinchuk |
| 2013/0245573 A1 | 9/2013 | de Juan, Jr. et al. |
| 2013/0253406 A1 | 9/2013 | Horvath et al. |
| 2013/0253528 A1 | 9/2013 | Haffner et al. |
| 2013/0281817 A1 | 10/2013 | Schaller et al. |
| 2013/0281908 A1 | 10/2013 | Schaller et al. |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0180189 A1 | 6/2014 | Horvath et al. |
| 2014/0236065 A1 | 8/2014 | Romoda et al. |
| 2014/0236066 A1 | 8/2014 | Horvath et al. |
| 2014/0236067 A1 | 8/2014 | Horvath et al. |
| 2014/0243730 A1 | 8/2014 | Horvath et al. |
| 2014/0272102 A1 | 9/2014 | Romoda et al. |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0287077 A1 | 9/2014 | Romoda et al. |
| 2014/0303544 A1 | 10/2014 | Haffner et al. |
| 2014/0323995 A1 | 10/2014 | Clauson et al. |
| 2014/0371651 A1 | 12/2014 | Pinchuk |
| 2015/0005689 A1 | 1/2015 | Horvath et al. |
| 2015/0045714 A1 | 2/2015 | Horvath et al. |
| 2015/0057591 A1 | 2/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256323 A1 | 9/2016 | Horvath et al. |
| 2016/0278982 A1 | 9/2016 | Horvath et al. |
| 2016/0354244 A1 | 12/2016 | Horvath et al. |
| 2016/0354245 A1 | 12/2016 | Horvath et al. |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0348150 A1 | 12/2017 | Horvath et al. |

FOREIGN PATENT DOCUMENTS

| | | |
|---|---|---|
| WO | WO 94/13234 A1 | 6/1994 |
| WO | WO 94/21205 A1 | 9/1994 |
| WO | WO 95/08310 A1 | 3/1995 |
| WO | WO 98/23237 A1 | 6/1998 |
| WO | WO-00/056255 A1 | 9/2000 |
| WO | WO-2000/056255 | 9/2000 |
| WO | WO 2002/074052 A2 | 9/2002 |
| WO | WO 2007/087061 A2 | 8/2007 |
| WO | WO 2008/005873 A1 | 1/2008 |

OTHER PUBLICATIONS

U.S. Appl. No. 14/541,070, filed Nov. 13, 2014, entitled "Intraocular Shunt Inserter".

U.S. Appl. No. 14/697,295, filed Apr. 27, 2015, entitled "Shunt Placement Through the Sclera".

U.S. Appl. No. 14/295,020, filed Jun. 3, 2014.

U.S. Appl. No. 14/295,022, filed Jun. 3, 2014.

U.S. Appl. No. 14/313,970, filed Jun. 24, 2014.

Horvath, U.S. Appl. No. 15/703,802, "Intraocular Shunt Implantation," filed Sep. 13, 2017.

Horvath, U.S. Appl. No. 15/807,503, "Manually Adjustable Intraocular Flow Regulation," filed Nov. 8, 2017.

* cited by examiner

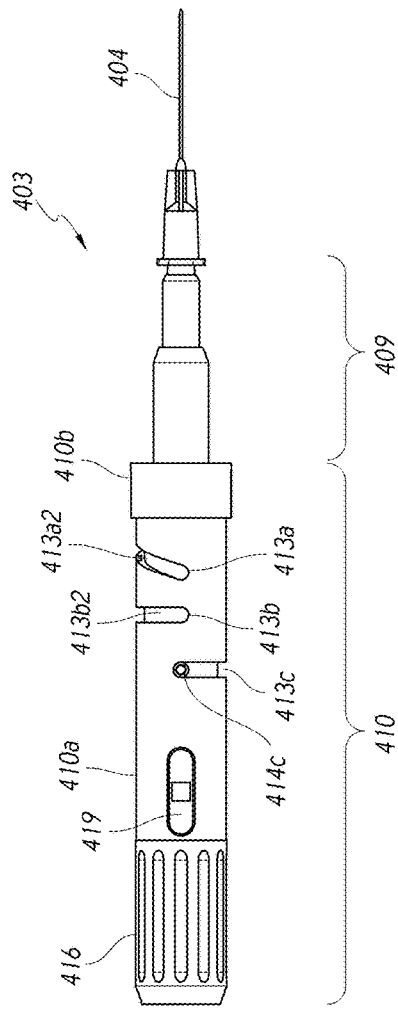
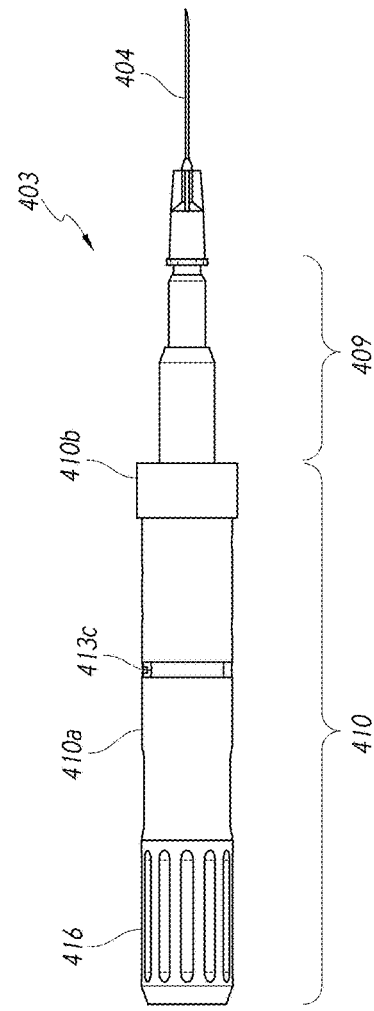

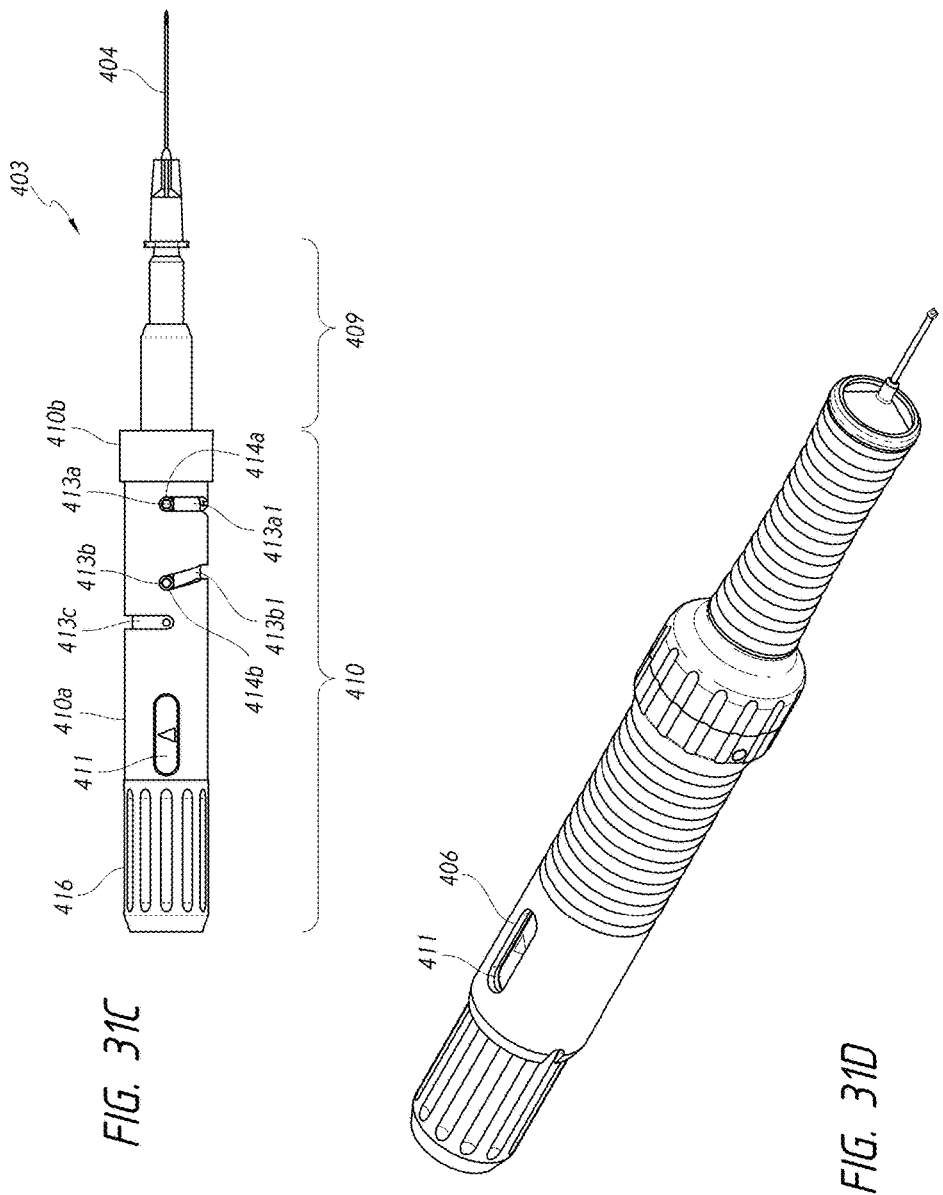

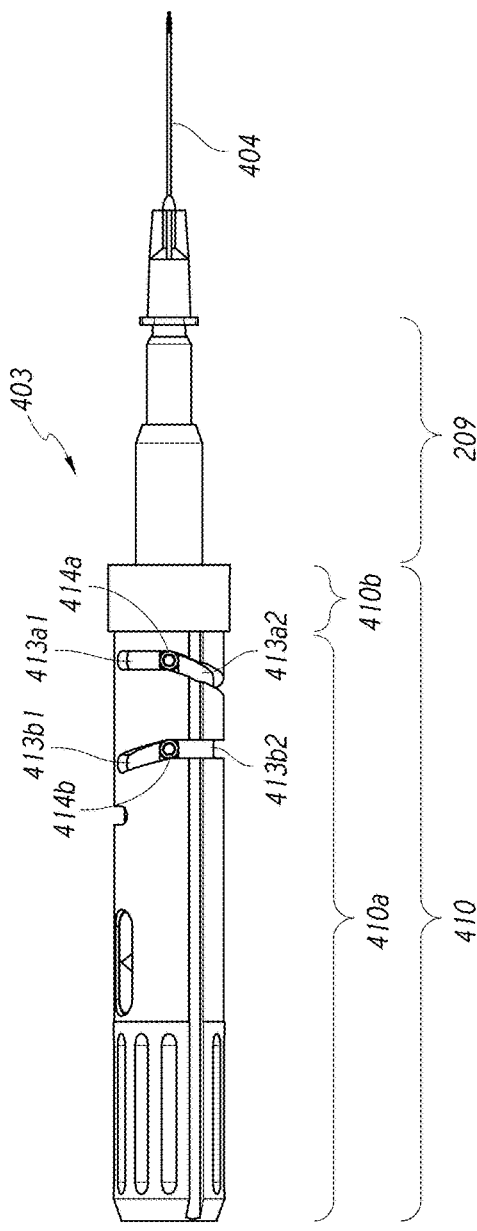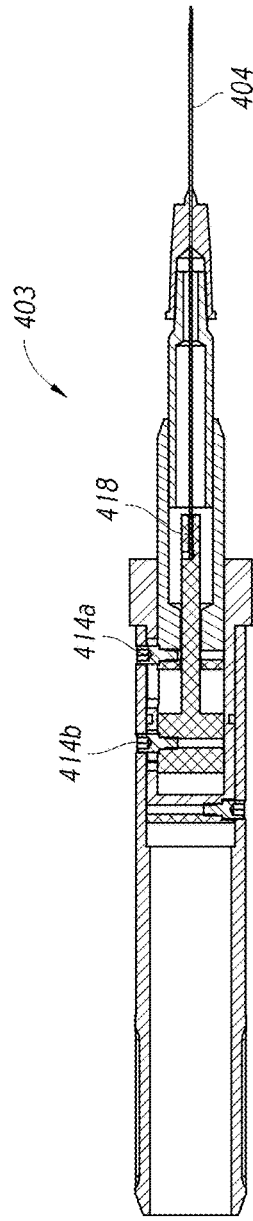
FIG. 34A
FIG. 34B

INTRAOCULAR DEVICES

CROSS-REFERENCE TO RELATED APPLICATIONS

This application is a continuation-in-part of U.S. patent application Ser. No. 12/946,572, filed on Nov. 15, 2010, now U.S. Pat. No. 8,852,256; this application is also a continuation-in-part of U.S. patent application Ser. No. 12/946,222, filed on Nov. 15, 2010, now abandoned; this application is also a continuation-in-part of U.S. patent application Ser. No. 12/946,240, filed on Nov. 15, 2010, now U.S. Pat. No. 8,828,070; this application is also a continuation-in-part of U.S. patent application Ser. No. 12/946,251, filed on Nov. 15, 2010, now U.S. Pat. No. 9,095,411; this application is also a continuation-in-part of U.S. patent application Ser. No. 12/946,263, filed on Nov. 15, 2010, now U.S. Pat. No. 8,801,766; this application is also a continuation-in-part of U.S. patent application Ser. No. 13/314,927, filed Dec. 8, 2011, now abandoned, which is a continuation-in-part of U.S. patent application Ser. No. 12/946,351, filed on Nov. 15, 2010, now abandoned; this application is also a continuation-in-part of U.S. patent application Ser. No. 12/946,556, filed on Nov. 15, 2010, now abandoned; this application is also a continuation-in-part of U.S. patent application Ser. No. 14/263,957, filed on Apr. 28, 2014, now U.S. Pat. No. 9,283,116, which is a continuation of U.S. patent application Ser. No. 12/946,645, filed on Nov. 15, 2010, now U.S. Pat. No. 8,721,702; this application is also a continuation-in-part of U.S. patent application Ser. No. 14/191,340, filed on Feb. 26, 2014, now U.S. Pat. No. 9,192,516, which is a continuation of U.S. patent application Ser. No. 12/946,653, filed on Nov. 15, 2010, now U.S. Pat. No. 8,663,303; this application is also a continuation-in-part of U.S. patent application Ser. No. 12/946,565, filed on Nov. 15, 2010, now U.S. Pat. No. 8,974,511; this application is also a continuation-in-part of U.S. patent application Ser. No. 13/336,758, filed on Dec. 23, 2011, now U.S. Pat. No. 8,852,137; which is a continuation-in-part of U.S. patent application Ser. No. 12/946,351, filed on Nov. 15, 2010, now abandoned, and which is a continuation-in-part of U.S. patent application Ser. No. 12/946,222, filed on Nov. 15, 2010, now abandoned; this application is also a continuation-in-part of U.S. patent application Ser. No. 13/336,803, filed on Dec. 23, 2011, now U.S. Pat. No. 8,758,290, which is a continuation-in-part of U.S. patent application Ser. No. 12/946,351, filed on Nov. 15, 2010, now abandoned, and which is a continuation-in-part of U.S. patent application Ser. No. 12/946,222, filed on Nov. 15, 2010, now abandoned; this application is also a continuation-in-part of U.S. patent application Ser. No. 13/895,170, filed on May 15, 2013, which is a continuation of International Pat. App. No. PCT/US2011/060820, filed on Nov. 15, 2011, which claims the benefit of and priority to U.S. patent application Ser. No. 12/946,210, filed on Nov. 15, 2010, now U.S. Pat. No. 8,308,701; and this application is also a continuation-in-part of U.S. patent application Ser. No. 13/952,543, filed on Jul. 26, 2013, now U.S. Pat. No. 9,017,276, which is a continuation of U.S. patent application Ser. No. 12/946,542, filed on Nov. 15, 2010, now abandoned; the entireties of each of these applications and patents are incorporated herein by reference.

BACKGROUND

Field of the Inventions

The present inventions generally relate to surgical methods, implantation devices, and shunts that can be used to treat glaucoma.

Description of the Related Art

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness. Glaucoma affects 1 in 200 people aged fifty and younger, and 1 in 10 over the age of eighty for a total of approximately 70 million people worldwide, and glaucoma is the second leading cause of blindness in the world.

There are two main types of glaucoma, "open angle" and "closed angle" glaucoma. Open angle glaucoma refers to glaucoma cases in which intraocular pressure increases but an anterior chamber angle (drainage angle) of an eye remains open. A common cause of open angle glaucoma is blockage in the trabecular meshwork, the fluid flow pathways that normally drain aqueous humor from the anterior chamber of the eye. Closed angle glaucoma refers to glaucoma cases in which intraocular pressure increases due to partial or complete closure of the anterior chamber angle. In closed angle glaucoma, swelling or movement of the iris closes the anterior chamber angle and blocks fluid from accessing to the trabecular meshwork, which in turn obstructs outflow of the aqueous humor from the eye.

Generally, glaucoma may be treated by surgical intervention that involves placing a shunt in the eye to result in production of fluid flow pathways between the anterior chamber and various structures of the eye involved in aqueous humor drainage (e.g., Schlemm's canal, the sclera, or the subconjunctival space). Such fluid flow pathways allow for aqueous humor to exit the anterior chamber. Generally, the surgical intervention to implant the shunt involves inserting into the eye a delivery device that holds an intraocular shunt, and deploying the shunt within the eye.

A delivery device holding the shunt enters the eye through a cornea (ab interno approach), and is advanced across the anterior chamber. The delivery device is advanced through the sclera until a distal portion of the device is in proximity to a drainage structure of the eye. The shunt is then deployed from the delivery device, producing a conduit between the anterior chamber and various structures of the eye involved in aqueous humor drainage (e.g., Schlemm's canal, the sclera, or the subconjunctival space). See for example, Yu et al. (U.S. Pat. No. 6,544,249 and U.S. Pat. Pub. No. 2008/0108933) and Prywes (U.S. Pat. No. 6,007,511). Such fluid flow pathways allow for aqueous humor to exit the anterior chamber, thereby reducing IOP.

Such a surgical procedure requires an optical apparatus, such as a goniolens, so that a surgeon may visualize the delivery device within the eye and ensure proper placement of the shunt after it has been deployed from the delivery device.

Further, various manual and automated deployment devices for implanting an intraocular shunt have been described. See, for example, U.S. Pat. No. 6,544,249 and U.S. Pat. Pub. No. 2008/0108933. Most deployment devices are coupled to a hollow needle which holds the intraocular shunt. Whether an ab externo approach or an ab interno approach is used, the needle is inserted into the eye to deploy the intraocular shunt into the eye. The needle is then withdrawn from the eye.

SUMMARY

A problem with treating closed angle glaucoma with surgical intervention is that the closed anterior chamber angle prevents an operator from advancing the deployment device into the anterior chamber angle, and thus the device cannot be properly positioned to deploy an intraocular shunt.

The present inventions generally relate, among other things, to methods for treating closed angle glaucoma that involve using a deployment device that is configured to both re-open a partially or completely closed anterior chamber angle and deploy an intraocular shunt. By re-opening the anterior chamber angle, the deployment device is provided access to the anterior chamber angle so that an operator may properly position the device to deploy the intraocular shunt, thereby generating a fluid flow pathway for outflow of aqueous humor from an anterior chamber of an eye.

In certain aspects, some methods involve inserting into an eye a deployment device configured to hold an intraocular shunt, using the device to re-open an at least partially closed anterior chamber angle of an eye, and deploying the shunt from the device. Deploying the shunt results in a flow path from an anterior chamber of the eye to an area of lower pressure. Exemplary areas of lower pressure include intra-Tenon's space, the subconjunctival space, the episcleral vein, the subarachnoid space, the suprachoroidal space, Schlemm's canal, or drainage structures associated with the intra-scleral space.

In other aspects, some methods involve inserting into an eye a deployment device configured to hold an intraocular shunt, advancing the device such that a protrusion on a distal end of the device advances into an at least partially closed anterior chamber angle of the eye, thereby re-opening the closed angle, and deploying the shunt from the device. In certain embodiments, a distal portion of the device includes a sleeve and a hollow shaft that is movable within the sleeve.

The present inventions generally provide improved shunts that facilitate drainage of fluid from an organ. Particularly, some embodiments of the shunt address and solve the problems with intraocular shunts.

The present inventions also generally relate to devices for deploying intraocular shunts from a delivery device without use of an optical apparatus that contacts the eye, preferably without use of any optical apparatus. Some devices accomplish shunt deployment without use of an optical apparatus by having a biased distal portion, such that upon entry of the distal portion of the device into an anterior chamber of an eye, the distal portion slides to fit within the anterior chamber angle of the eye. A resistance feedback feature of the device informs an operator that the deployment device is properly positioned within the anterior chamber angle of the eye for deployment and proper placement of the shunt within the eye.

In particular embodiments, some methods involve inserting into an eye a deployment device configured to hold an intraocular shunt, determining that a distal portion of the device is properly positioned within the eye without use of an optical apparatus that contacts the eye, and deploying the shunt from the device. In certain embodiments, determining involves advancing the device until a resistance is encountered. The resistance indicates to an operator that a distal end of the device has advanced across the anterior chamber of the eye and that a distal portion of the device is fitted within an anterior chamber angle of the eye, and is thereby properly positioned for deployment of the intraocular shunt.

Another aspect of some embodiments provides methods for deploying a shunt within an eye including inserting into an eye a deployment device configured to hold an intraocular shunt, advancing the device until a protrusion on a distal end of a housing of the device contacts an anterior chamber angle of the eye, thereby providing resistance against further advancement of the device, and deploying the shunt from the device. In certain embodiments, a distal portion of the housing comprises a sleeve and a hollow shaft that is movable within the sleeve.

In certain embodiments, some devices include a housing having an angled distal end, a deployment mechanism at least partially disposed within the housing, and a hollow shaft coupled to the deployment mechanism, in which the shaft is configured to hold an intraocular shunt. Some devices may further include an intraocular shunt that is at least partially disposed within the shaft. In particular embodiments, the angle of the distal end is substantially identical to an anterior chamber angle of an eye.

The housing of some devices may include a proximal portion and a distal portion. In certain embodiments, the distal portion of the housing is movable within the proximal portion of the housing. The housing may further include a member that limits axial retraction of the distal portion of the housing.

In certain embodiments, the distal portion includes a capsule and a sleeve. In other embodiments, a distal end of the sleeve further includes a protrusion. The protrusion may be formed integrally with the distal end of the sleeve or may be connected to a distal end of the sleeve. The protrusion may surround the distal end of the sleeve, or the protrusion may extend around only a portion of the sleeve. In certain embodiments, the protrusion is a collar that surrounds the distal end of the sleeve. In other embodiments, the protrusion includes a flat bottom portion and an angled top portion. In particular embodiments, the angle of the top portion is substantially identical to an anterior chamber angle of an eye.

Some methods and devices are typically conducted using an ab interno approach. Such an approach is contrasted with an ab externo approach, which involves inserting a deployment device through the conjunctiva of the eye. Although, some methods may be conducted using an ab externo approach.

Some methods may be performed such that the distal portion of the deployment device or shaft is inserted above or below the corneal limbus. Some methods may be performed such that the distal portion of the deployment device or shaft is inserted into the eye without removing an anatomical feature of the eye, such as the trabecular meshwork, the iris, the cornea, and the aqueous humor. In certain embodiments, some methods may be conducted without inducing substantial ocular inflammation such as, for example, subconjunctival blebbing or endophthalmitis.

The deployment configuration involves engagement of the deployment mechanism. In certain embodiments, the deployment mechanism may include a two stage system. The first stage is a pusher component and the second stage is a retraction component. Rotation of the deployment mechanism sequentially engages the pusher component and then the retraction component. The pusher component pushes the shunt to partially deploy the shunt from within the shaft, and the retraction component retracts the shaft from around the shunt. The deployment mechanism further includes at least one member that limits axial movement of the shaft.

The hollow shaft of the deployment device may have various shapes and sizes. In certain embodiments, a distal end of the shaft is beveled. In particular embodiments, the bevel is a double bevel. In certain embodiments, the angle of the bevel is such that upon insertion of the shaft through the sclera of an eye, the bevel is substantially parallel with the conjunctiva of an eye. In certain embodiments, the hollow shaft is a needle.

Some devices may be completely automated, partially automated, or completely manual. Some devices may be connected to larger robotic systems or may be used as stand-alone handheld deployment devices. In particular embodiments, the device is a handheld device.

Some devices may include an indicator that provides feedback to an operator as to the state of the deployment mechanism. The indicator may be any type of indicator known in the art, for example a visual indicator, an audio indicator, or a tactile indicator. In certain embodiments, the indicator is a visual indicator.

Other aspects of some embodiments provide devices for deploying an intraocular shunt that include a housing, in which a distal end of the housing includes a protrusion, a deployment mechanism at least partially disposed within the housing, and a hollow shaft coupled to the deployment mechanism, in which the shaft is configured to hold an intraocular shunt. The devices may further include an intraocular shunt that is at least partially disposed within the shaft.

Another aspect of some embodiments provides devices for deploying an intraocular shunt that include a deployment mechanism, a hollow shaft coupled to the deployment mechanism and configured to hold an intraocular shunt, and a member adapted to provide resistance feedback to an operator upon a distal portion of the device contacting an anatomical feature of the eye, such as the sclera. The resistance feedback indicates to an operator that a distal portion of the device is properly positioned to deploy the shunt.

Another aspect of some embodiments provides devices for deploying an intraocular shunt that include a deployment mechanism, a hollow shaft coupled to the deployment mechanism and configured to hold an intraocular shunt, and means for providing feedback to an operator advancing the shaft. The feedback indicates to an operator that a distal portion of the shaft is properly positioned to deploy the shunt. In certain embodiments, the feedback is resistance feedback.

Other aspects of some embodiments provide devices for deploying an intraocular shunt including a housing having a proximal portion and a distal portion, in which the distal portion is movable within the proximal portion, a deployment mechanism at least partially disposed within the housing, and a hollow shaft coupled to the deployment mechanism, in which the shaft is configured to hold an intraocular shunt. The devices may further include an intraocular shunt that is at least partially disposed within the shaft.

Some devices include numerous configurations, such as an insertion configuration, a shaft exposure configuration, and a deployment configuration. The insertion configuration includes the hollow shaft fully disposed within the sleeve. The shaft exposure configuration includes retraction of the capsule to at least partially within the proximal portion of the housing, thereby exposing a distal portion of the hollow shaft from the sleeve.

Other aspects of some embodiments provide devices for deploying an intraocular shunt that includes a housing, a deployment mechanism at least partially disposed within the housing, and a hollow shaft coupled inside the housing to the deployment mechanism, in which the shaft is configured to hold an intraocular shunt. These devices include an insertion configuration and a deployment configuration and the insertion configuration involves the shaft being fully disposed within the housing. The devices may further include an intraocular shunt that is at least partially disposed within the shaft.

Further, some embodiments relate to eliminating or at least minimizing damage to the eye of a patient during an intraocular shunt placement procedure. Intraocular shunts are typically deployed into the eye using a deployment device that includes or is coupled to a hollow shaft, such as a needle, that holds the intraocular shunt. The hollow shaft of the deployment device is inserted into the eye, then the shunt is deployed into the eye from the deployment device. Once inserted into the eye, the interaction between the hollow shaft of the deployment device and surrounding eye tissue oftentimes causes the shaft to become stuck in the surrounding eye tissue (due to frictional resistance, for example), which can cause severe eye trauma upon shunt deployment or withdrawal of the shaft from the eye. This trauma is avoided or at least minimized in some embodiments by loosening the hollow shaft from the surrounding eye tissue prior to deploying the shunt into the eye from the deployment device and/or withdrawing the hollow shaft from the eye.

The present inventions provide improved methods for implantation of intraocular shunts. In one aspect, some methods involve the insertion into the eye of a portion of a deployment device comprising an intraocular shunt, loosening the portion of deployment device from the surrounding eye tissue, deploying the shunt into the eye from the deployment device, then withdrawing the portion of the deployment device from the eye. In one particular embodiment, the methods involve inserting into the eye a portion of a deployment device comprising an intraocular shunt without removing an anatomical feature of the eye, loosening the portion of the deployment device from the surrounding eye tissue, deploying the shunt into the eye from the deployment device, then withdrawing the portion of the deployment device from the eye. Loosening of the portion of the deployment device inserted into the eye from the surrounding eye tissue can be achieved, for example, by rotating the deployment device or a portion of the deployment device, other than the portion inserted into the eye. Rotation of the deployment device, or portion thereof, causes the portion of the deployment device inserted into the eye to also rotate, thereby loosening the deployment device from the surrounding eye tissue. Examples of eye tissue surrounding the portion of the deployment device inserted into the eye include, without limitation, the scleral tissue and/or the trabecular meshwork.

The loosening and deployment steps of some methods do not have to be conducted in any particular order. For example, some methods may involve inserting into the eye a portion of a deployment device comprising an intraocular shunt, deploying the shunt into the eye from the deployment device, loosening the portion of the deployment device from the surrounding eye tissue, then withdrawing the portion of the deployment device from the eye.

The deployment device may be configured such that a proximal portion of the deployment device is rotated to loosen the portion of the deployment device in the eye from the surrounding eye tissue before or after deploying the shunt into the eye. Alternatively, the deployment device may be configured such that a distal portion of the deployment device is rotated to loosen the portion of the deployment device in the eye from the surrounding eye before or after deploying the shunt into the eye. In yet another embodiment, the entire deployment device may be rotated to loosen the portion of the deployment device in the eye from the surrounding eye tissue before or after deploying the shunt into the eye. Preferably, the deployment device, or a portion thereof, is rotated about its longitudinal axis. Rotation can be in a clockwise or counterclockwise direction.

In another aspect, the present inventions relate to methods for implanting an intraocular shunt into an eye by inserting into the eye a portion of a deployment device comprising an intraocular shunt, whereby insertion into the eye is at an angle above or below the corneal limbus, rather than through the corneal limbus. Preferably, the portion of the deployment device is inserted into the eye at an angle above the corneal limbus. For example, a portion of a deployment device comprising an intraocular shunt is inserted into the eye approximately 1 mm to 2 mm above the corneal limbus, or any specific value within said range, e.g., 1 mm, 1.1 mm, 1.2 mm, 1.3 mm, 1.4 mm, 1.5 mm, 1.6 mm, 1.7 mm, 1.8 mm, 1.9 mm or 2 mm above the corneal limbus. The shunt is then deployed into the eye from the deployment device, and the portion of the deployment device is withdrawn from the eye. Shunt implantation methods above or below the corneal limbus are preferably coupled with the step of loosening the deployment device from the surrounding eye tissue before or after deploying the shunt into the eye, as previously described.

Preferably, some methods are conducted using an ab interno approach by inserting a portion of a deployment device comprising an intraocular shunt through the cornea, across the anterior chamber, through the sclera and into an aqueous humor drainage structure such as the intra-Tenon's space, the subconjunctival space, the episcleral vein the suprachoroidal space or Schlemm's canal. Such an approach is contrasted with an ab externo approach, which may also be used, and which involves inserting the portion of the deployment device comprising an intraocular shunt from the outside of the eye through the conjunctiva and inward through the sclera to reach a drainage structure such as Schlemm's canal. Although, some methods may be conducted using an ab externo approach.

In other certain embodiments, some methods are conducted without the use of an optical apparatus, particularly an optical apparatus that directly contacts the eye, such as a goniolens. In yet other certain embodiments, some methods are conducted using an optical apparatus that does not directly contact the eye, such as an ophthalmic microscope.

In a particular embodiment, some methods are reversible. That is, intraocular shunts that are implanted into the eye in accordance with some methods can be removed from the eye and a second shunt can be implanted in the eye.

Deployment of an intraocular shunt into the eye in accordance with some methods results in the formation of a passage that directs aqueous humor fluid flow from an area of high pressure in the eye, typically the anterior chamber, to an area of lower pressure within the eye, such as the intra-Tenon's space, the subconjunctival space, the episcleral vein, the suprachoroidal space or Schlemm's canal. Alternatively, the shunt is deployed in accordance with some methods such that it form a passage that directs aqueous humor fluid flow from an area of high pressure, such as the anterior chamber, to an area of lower pressure within the head, such as the subarachnoid space. In a preferred embodiment, deployment of an intraocular shunt in accordance with some methods results in the formation of a passage that directs aqueous humor fluid flow from the anterior chamber of the eye to the intra-Tenon's space.

The present inventions generally relate to methods for deploying intraocular shunts into the subconjunctival space the eye while avoiding or minimizing contact with the conjunctiva. In particular, the present inventions provide methods for deploying an intraocular shunt into the eye such that the shunt forms a drainage pathway from the anterior chamber of the eye to the region of the eye that is bound between the sclera and Tenon's capsule, referred to herein as the intra-Tenon's space. Deployment of an intraocular shunt such that the shunt inlet (i.e., the portion of the shunt that receives fluid from an anterior chamber of the eye) terminates in the anterior chamber and the shunt outlet (i.e., the portion of the shunt that directs fluid to the intra-Tenon's space) terminates in the intra-Tenon's space safeguards the integrity of the conjunctiva to allow subconjunctival drainage pathways to successfully form.

Some methods involve inserting into the eye a hollow shaft that is configured to hold an intraocular shunt, deploying the shunt from the shaft such that the shunt forms a passage from the anterior chamber to the intra-Tenon's space, and withdrawing the hollow shaft from the eye. The hollow shaft may hold the shunt within the interior of hollow shaft. Alternatively, the hollow shaft may hold the shunt on an outer surface of the shaft. In certain embodiments, some methods involve the use of a hollow shaft configured to hold an intraocular shunt, as previously described, wherein a portion of the hollow shaft extends linearly along a longitudinal axis and at least one other portion of the shaft extends off the longitudinal axis, to insert and deploy the intraocular shunt into the eye such that the shunt forms a passage from the anterior chamber to the intra-Tenon's space.

Optionally, an aqueous fluid is injected into the eye simultaneously with or prior to the insertion and deployment steps of some methods. For example, an aqueous solution may be injected below Tenon's capsule to balloon the capsule away from the sclera and allow positioning of the intraocular shunt in the intra-Tenon's space.

In certain aspects, the present inventions generally provide shunts composed of a material that has an elasticity modulus that is compatible with an elasticity modulus of tissue surrounding the shunt. In this manner, some embodiments of the shunt are flexibility matched with the surrounding tissue, and thus will remain in place after implantation without the need for any type of anchor that interacts with the surrounding tissue. Consequently, some embodiments of the shunt will maintain fluid flow away for an anterior chamber of the eye after implantation without causing irritation or inflammation to the tissue surrounding the eye.

Although discussed in the context of the eye, the elasticity modulus of the shunt may be matched to the elasticity modulus of any tissue. Thus, some embodiments of the shunt may be used to drain fluid from any organ. In particular embodiments, the organ is an eye. Some embodiments of the shunt may define a flow path from an area of high pressure in the eye (e.g., an anterior chamber) to an area of lower pressure in the eye (e.g., intra-Tenon's space, the subconjunctival space, the episcleral vein, the suprachoroidal space, and Schlemm's canal).

In other aspects, the present inventions generally provide shunts in which a portion of the shunt is composed of a flexible material that is reactive to pressure, i.e., an inner diameter of the shunt fluctuates depending upon the pressures exerted on that portion of the shunt. Thus, the flexible portion of the shunt acts as a valve that regulates fluid flow through the shunt. After implantation, intraocular shunts have pressure exerted upon them by tissues surrounding the shunt (e.g., scleral tissue) and pressure exerted upon them by aqueous humor flowing through the shunt. When the pressure exerted on the flexible portion of the shunt by the surrounding tissue is greater than the pressure exerted on the flexible portion of the shunt by the fluid flowing through the shunt, the flexible portion decreases in diameter, restricting flow through the shunt. The restricted flow results in aqueous humor leaving the anterior chamber at a reduced rate.

When the pressure exerted on the flexible portion of the shunt by the fluid flowing through the shunt is greater than the pressure exerted on the flexible portion of the shunt by the surrounding tissue, the flexible portion increases in diameter, increasing flow through the shunt. The increased flow results in aqueous humor leaving the anterior chamber at an increased rate.

The flexible portion of the shunt may be any portion of the shunt. In certain embodiments, the flexible portion is a distal portion of the shunt. In certain embodiments, the entire shunt is composed of the flexible material.

Other aspects of the present inventions generally provide multi-port shunts. Such shunts reduce probability of the shunt clogging after implantation because fluid can enter or exit the shunt even if one or more ports of the shunt become clogged with particulate. In certain embodiments, the shunt includes a hollow body defining a flow path and more than two ports, in which the body is configured such that a proximal portion receives fluid from the anterior chamber of an eye and a distal portion directs the fluid to a location of lower pressure with respect to the anterior chamber.

The shunt may have many different configurations. In certain embodiments, the proximal portion of the shunt (i.e., the portion disposed within the anterior chamber of the eye) includes more than one port and the distal portion of the shunt (i.e., the portion that is located in an area of lower pressure with respect to the anterior chamber such as intra-Tenon's space, the subconjunctival space, the episcleral vein, the suprachoroidal space, or Schlemm's canal) includes a single port. In other embodiments, the proximal portion includes a single port and the distal portion includes more than one port. In still other embodiments, the proximal and the distal portions include more than one port.

The ports may be positioned in various different orientations and along various different portions of the shunt. In certain embodiments, at least one of the ports is oriented at an angle to the length of the body. In certain embodiments, at least one of the ports is oriented 90° to the length of the body.

The ports may have the same or different inner diameters. In certain embodiments, at least one of the ports has an inner diameter that is different from the inner diameters of the other ports.

Other aspects of the present inventions generally provide shunts with overflow ports. Those shunts are configured such that the overflow port remains closed until there is a pressure build-up within the shunt sufficient to force open the overflow port. Such pressure build-up typically results from particulate partially or fully clogging an entry or an exit port of the shunt. Such shunts reduce probability of the shunt clogging after implantation because fluid can enter or exit the shunt by the overflow port even if one port of the shunt becomes clogged with particulate.

In certain embodiments, the shunt includes a hollow body defining an inlet configured to receive fluid from an anterior chamber of the eye and an outlet configured to direct the fluid to a location of lower pressure with respect to the anterior chamber, the body further including at least one slit. The slit may be located at any place along the body of the shunt. In certain embodiments, the slit is located in proximity to the inlet. In other embodiments, the slit is located in proximity to the outlet. In certain embodiments, there is a slit in proximity to both the inlet and the outlet of the shunt.

In certain embodiments, the slit has a width that is substantially the same or less than an inner diameter of the inlet. In other embodiments, the slit has a width that is substantially the same or less than an inner diameter of the outlet. Generally, the slit does not direct the fluid unless the outlet is obstructed. However, the shunt may be configured such that the slit does direct at least some of the fluid even if the inlet or outlet is not obstructed.

In other aspects, the present inventions generally provide a shunt having a variable inner diameter. In particular embodiments, the diameter increases from inlet to outlet of the shunt. By having a variable inner diameter that increases from inlet to outlet, a pressure gradient is produced and particulate that may otherwise clog the inlet of the shunt is forced through the inlet due to the pressure gradient. Further, the particulate will flow out of the shunt because the diameter only increases after the inlet.

In certain embodiments, the shunt includes a hollow body defining a flow path and having an inlet configured to receive fluid from an anterior chamber of an eye and an outlet configured to direct the fluid to a location of lower pressure with respect to the anterior chamber, in which the body further includes a variable inner diameter that increases along the length of the body from the inlet to the outlet. In certain embodiments, the inner diameter continuously increases along the length of the body. In other embodiments, the inner diameter remains constant along portions of the length of the body. Exemplary locations of lower pressure include the intra-Tenon's space, the subconjunctival space, the episcleral vein, the subarachnoid space, and Schlemm's canal.

In certain embodiments, some embodiments of the shunt may be coated or impregnated with at least one pharmaceutical and/or biological agent or a combination thereof. The pharmaceutical and/or biological agent may coat or impregnate an entire exterior of the shunt, an entire interior of the shunt, or both. Alternatively, the pharmaceutical and/or biological agent may coat and/or impregnate a portion of an exterior of the shunt, a portion of an interior of the shunt, or both. Methods of coating and/or impregnating an intraocular shunt with a pharmaceutical and/or biological agent are known in the art. See, for example, Darouiche (U.S. Pat. Nos. 7,790,183; 6,719,991; 6,558,686; 6,162,487; 5,902,283; 5,853,745; and 5,624,704) and Yu et al. (U.S. Pat. Pub. No. 2008/0108933). The content of each of these references is incorporated by reference herein its entirety.

In certain embodiments, the exterior portion of the shunt that resides in the anterior chamber after implantation (e.g., about 1 mm of the proximal end of the shunt) is coated and/or impregnated with the pharmaceutical or biological agent. In other embodiments, the exterior of the shunt that resides in the scleral tissue after implantation of the shunt is coated and/or impregnated with the pharmaceutical or biological agent. In other embodiments, the exterior portion of the shunt that resides in the area of lower pressure (e.g., the intra-Tenon's space or the subconjunctival space) after implantation is coated and/or impregnated with the pharmaceutical or biological agent. In embodiments in which the pharmaceutical or biological agent coats and/or impregnates the interior of the shunt, the agent may be flushed through the shunt and into the area of lower pressure (e.g., the intra-Tenon's space or the subconjunctival space).

Any pharmaceutical and/or biological agent or combination thereof may be used with some embodiments of the shunt. The pharmaceutical and/or biological agent may be released over a short period of time (e.g., seconds) or may be released over longer periods of time (e.g., days, weeks, months, or even years). Exemplary agents include antimitotic pharmaceuticals such as Mitomycin-C or 5-Fluorouracil, anti-VEGF (such as Lucintes, Macugen, Avastin, VEGF or steroids).

The shunts discussed above and herein are described relative to the eye and, more particularly, in the context of treating glaucoma and solving the above identified problems relating to intraocular shunts. Nonetheless, it will be appreciated that shunts described herein may find application in any treatment of a body organ requiring drainage of a fluid from the organ and are not limited to the eye.

The present inventions provide devices and methods for self-guided implantation of soft gel tissue compliant intraocular shunts in the suprachoroidal space. Shunt placement in the suprachoroidal space avoids contact with the conjunctiva, thus safeguarding the integrity of the conjunctiva. Implanting shunts made of soft, tissue compliant material avoid the creation of a cyclodialysis cleft and reduces or eliminates the risk of hypotony and related side effects.

Some embodiments of the device accomplish self-guided shunt deployment in the suprachoroidal space by having a flexible hollow shaft with a bend that biases the shunt to follow the scleral spur as it is deployed from the shaft. The hollow shaft is pre-bent to match the angle or arc of the sclera. In a pre-deployment configuration, the shaft is disposed within the device. The rigidity of the device holds the hollow shaft in a straight configuration. Upon its exposure from the device, the hollow shaft reverts to its pre-bent configuration. Such a pre-bend allows the hollow shaft to follow the scleral spur down along the sclera in a self-guided manner to the suprachoroidal space. Additionally, the flexibility of the hollow shaft allows it to continually bend and flex in response to the anatomy as the hollow shaft advances from the device. Once properly positioned, the shunt is deployed from the shaft. The bend in the shaft self-guides the shunt along the scleral spur of the eye as the shaft is retracted into the device and the shunt is deployed from the shaft.

In certain aspects, some embodiments of the device also include a housing and a deployment mechanism at least partially disposed in the housing. In certain embodiments, the hollow shaft is coupled to the deployment mechanism. The housing may include two components, a proximal portion and a distal portion. The components are configured such that the distal portion is movable within the proximal portion. In certain embodiments, the distal portion of the housing includes a stiff sleeve and the shaft is movably disposed within the sleeve. In other embodiments, the distal portion is without a stiff outer sleeve. As previously described, the shaft is flexible and pre-bent to match an angle of the sclera. In certain embodiments, the distal end of the hollow shaft includes a sharp tip to assist in piercing the sclera. In certain embodiments, the hollow shaft is a flexible needle.

In other embodiments, a distal end of the sleeve further includes a protrusion. The protrusion may be formed integrally with the distal end of the sleeve or may be connected to a distal end of the sleeve. The protrusion may surround the distal end of the sleeve, or the protrusion may extend around only a portion of the sleeve. In certain embodiments, the protrusion is a collar that surrounds the distal end of the sleeve. In other embodiments, the protrusion includes a flat bottom portion and an angled top portion. In particular embodiments, the angle of the top portion is substantially identical to an anterior chamber angle of an eye.

Other aspects of some embodiments provide for methods of using the above described devices for inserting a intraocular shunt into the suprachoroidal space of an eye. Such methods involve inserting the above device into an eye and deploying a shunt from the device within the eye such that a proximal portion of the shunt receives fluid from an anterior chamber of an eye and a distal portion of the shunt directs the fluid to the suprachoroidal space. Some methods may also involve injecting a drug into the suprachoroidal space prior to deploying the shunt from the device. Exemplary drugs include drug is a BSS/steroids or antifibrotic agents.

BRIEF DESCRIPTION OF THE DRAWINGS

FIG. 14A shows an embodiment of a shunt in which the proximal portion of the shunt includes more than one port and the distal portion of the shunt includes a single port.

FIG. 14B shows another embodiment of a shunt in which the proximal portion includes a single port and the distal portion includes more than one port.

FIG. 14C shows another embodiment of a shunt in which the proximal portions include more than one port and the distal portions include more than one port.

FIG. 23B is a side view of the protrusion shown in FIG. 23A.

FIG. 23C is a top view of the protrusion shown in FIG. 23A.

FIGS. 27A-27D are schematics showing different enlarged views of the deployment mechanism of the deployment device with the shaft in a straight configuration, as if the shaft is within the stiff outer sleeve.

FIG. 28C shows the shaft in a straight configuration, as if it is within the stiff outer sleeve.

FIG. 31C show a schematic of the deployment mechanism in a pre-deployment or insertion configuration.

FIG. 31D is another schematic showing deployment some embodiments of the device in a pre-deployment or insertion configuration.

FIG. 32A is a magnified view of the position of the distal portion of the device relative to the proximal portion of the device in the insertion configuration. FIG. 32B is a magnified view of the sleeve of the device inserted into the eye. This figure also shows the sleeve and protrusion fitted within an anterior chamber angle of the eye.

FIGS. 34A-34B show schematics of the deployment mechanism at the end of the first stage of deployment of the shunt from the deployment device with the shaft in a straight configuration, as if the shaft is within the stiff outer sleeve.

FIG. 35A is a magnified view of the position of the distal portion of the device relative to the proximal portion of the device. FIG.

35B is a magnified view of the sleeve of the device inserted into the eye and the shaft extended from the sleeve.

Figure 36A:
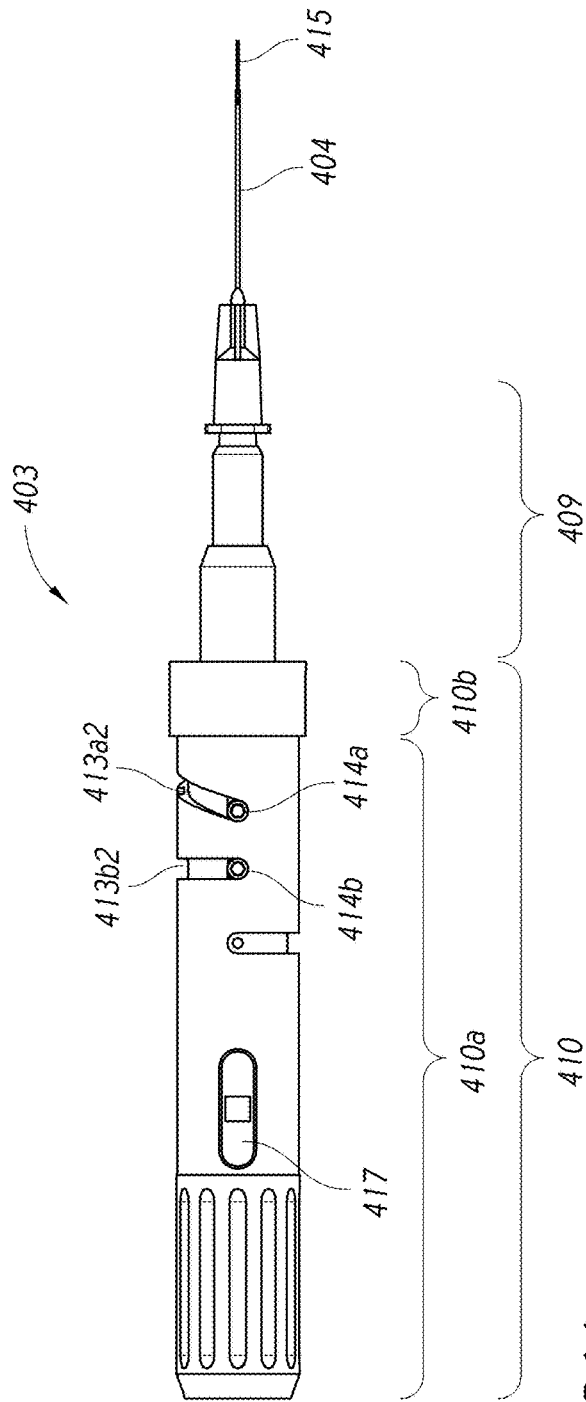

FIG. 36A show a schematic of the deployment mechanism at the end of the second stage of deployment.

Figure 36B:
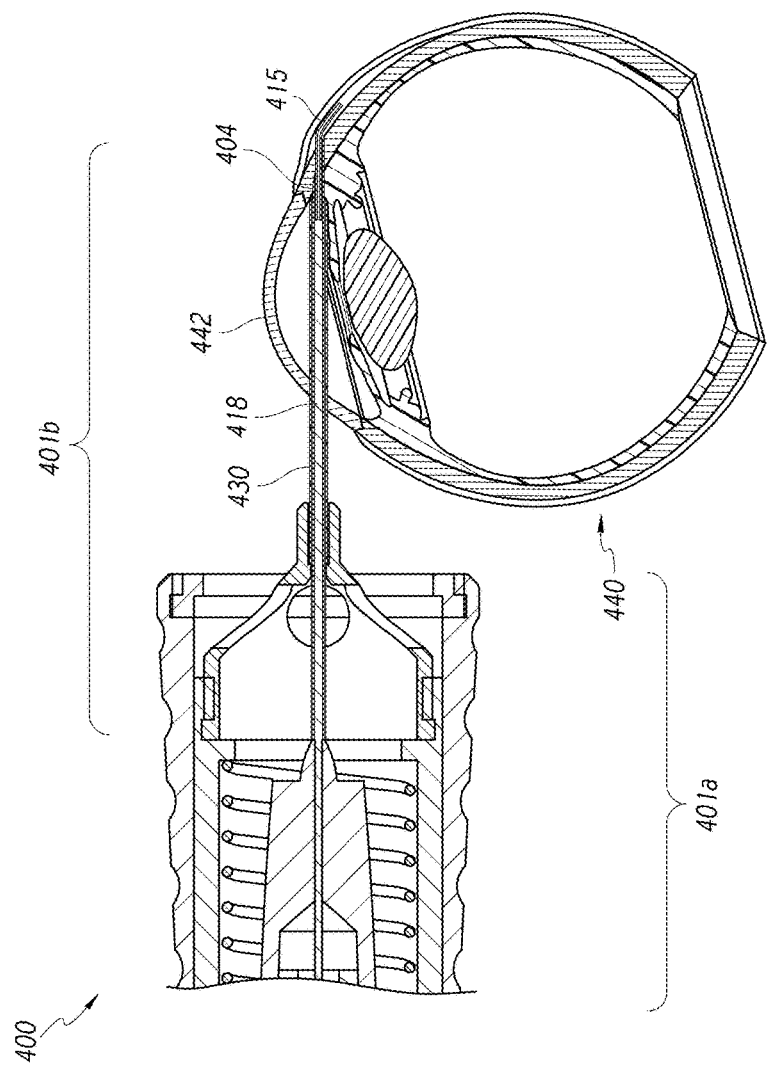

FIG. 36B shows another schematic of the deployment device at the end of the second stage of deployment.

Figure 36C:
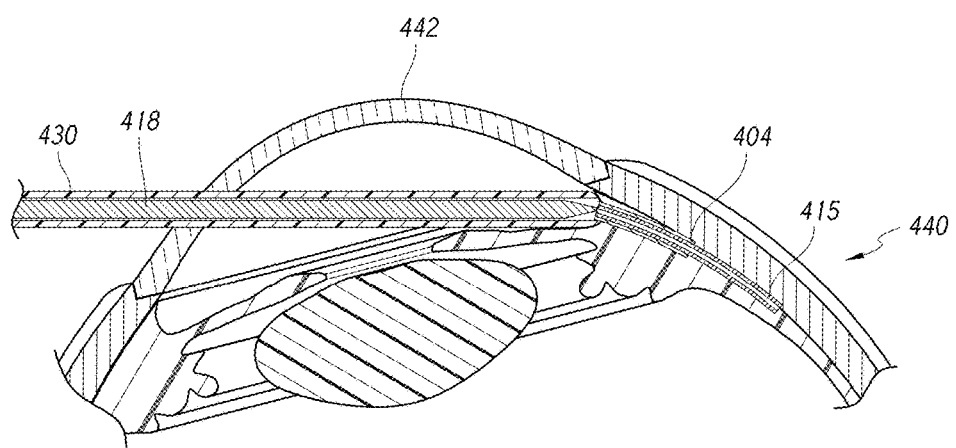

FIG. 36C is a magnified view of the sleeve of the device inserted into the eye, retraction of the shaft into the sleeve, and the shunt being deployed from the sleeve.

Figure 36D:
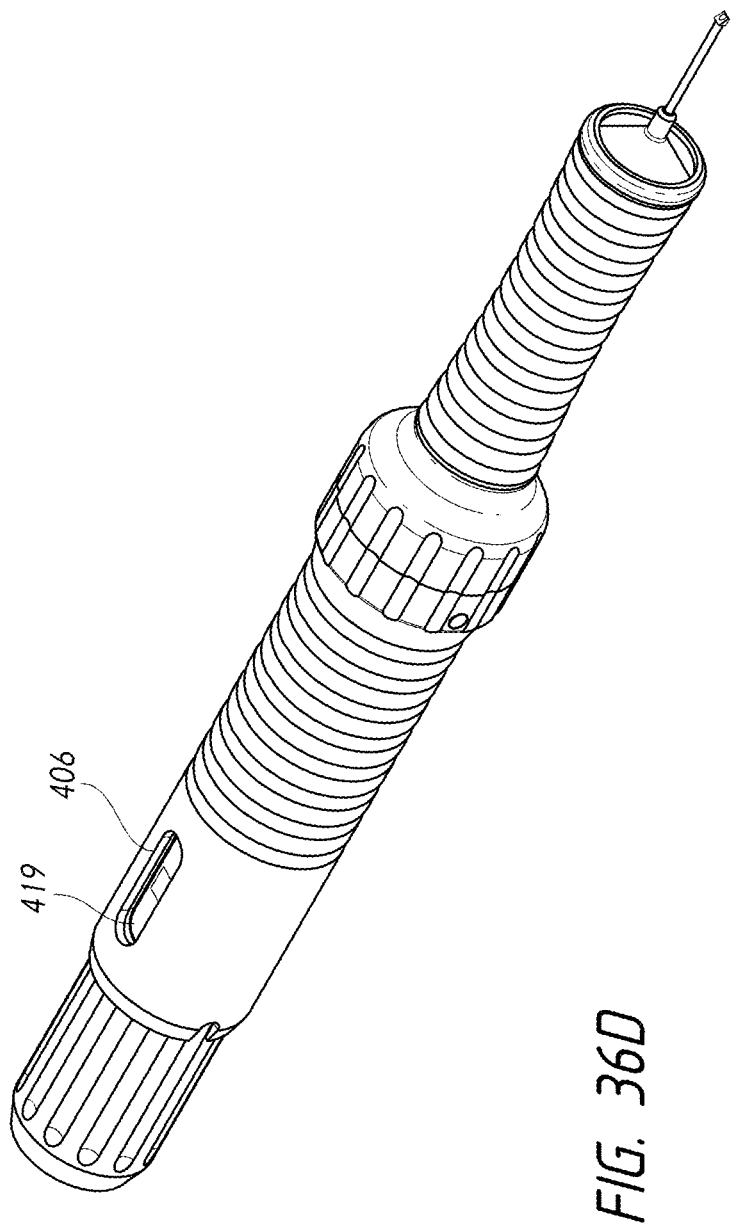

FIG. 36D shows another view of the deployment device at the end of the second stage of deployment.

Figure 37A:
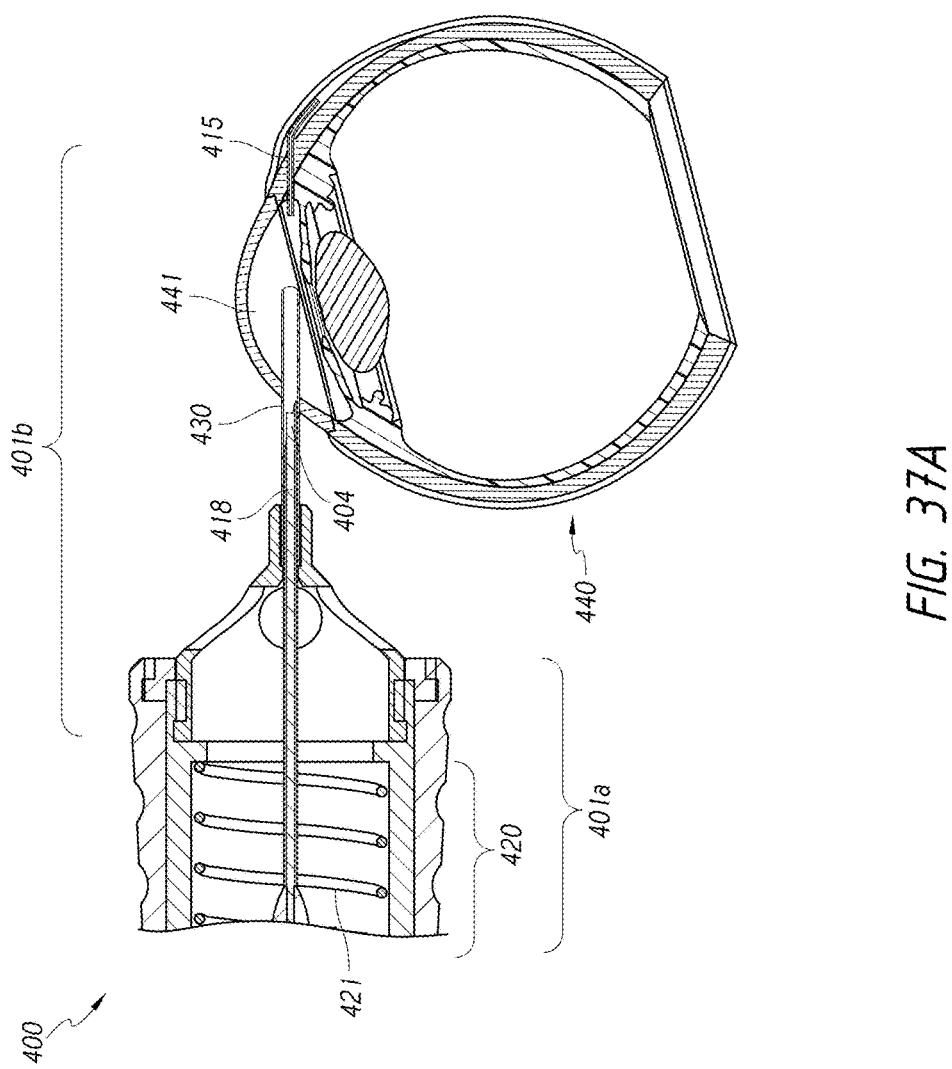

FIG. 37A is a schematic showing the deployment device after completion of deployment of the shunt from the device and in to the eye.

Figure 37B:
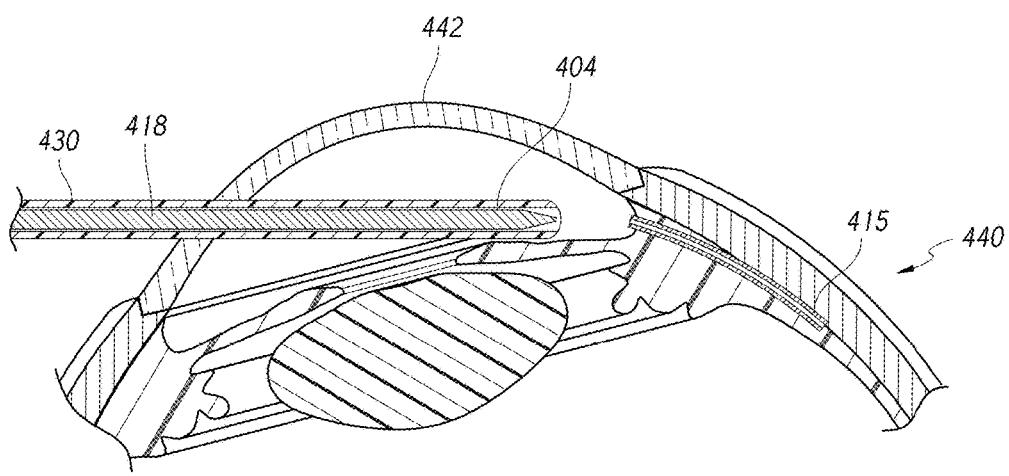
Figure 38A:
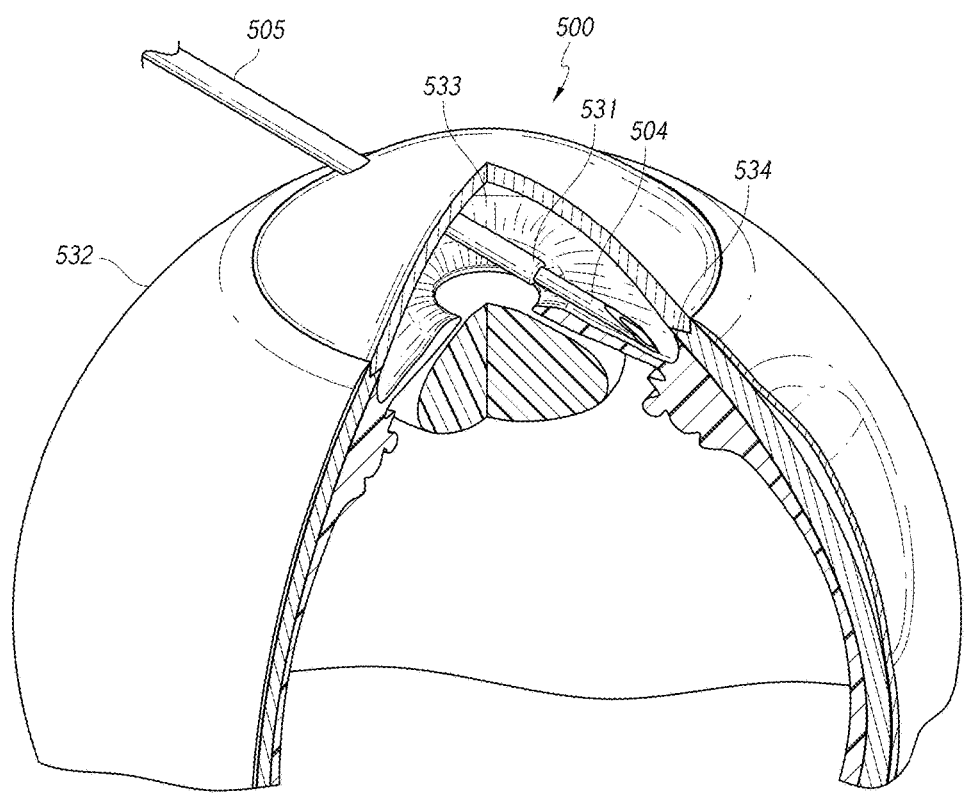
Figure 38B:
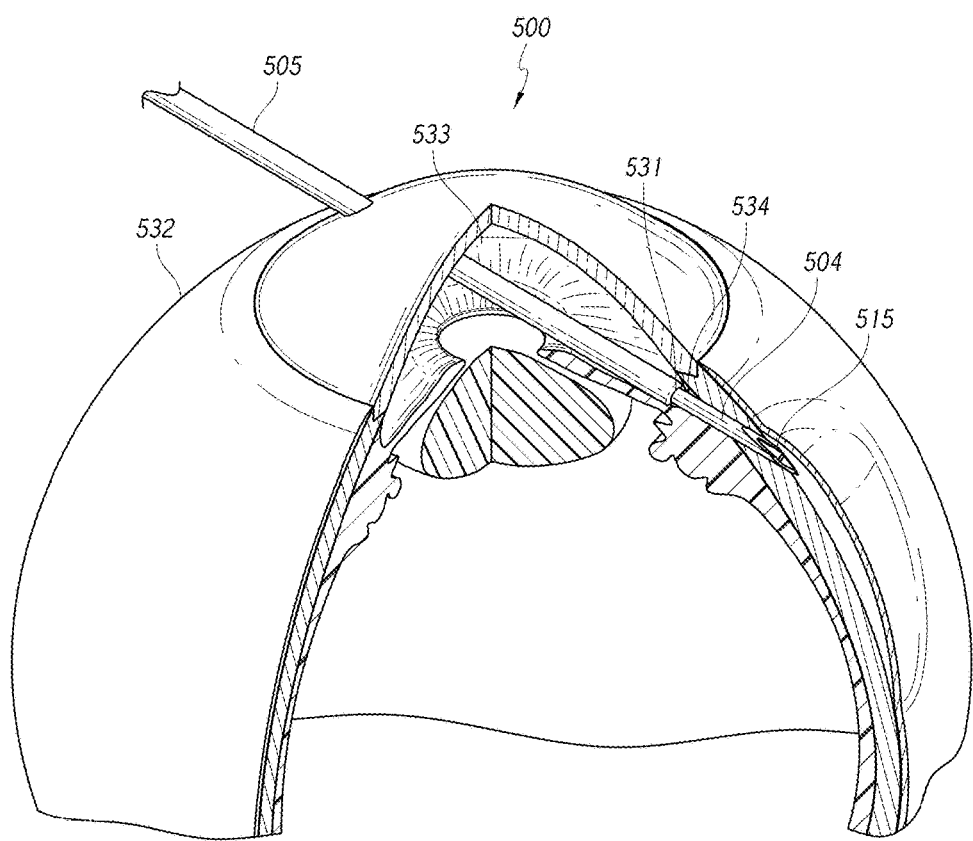
Figure 38C:
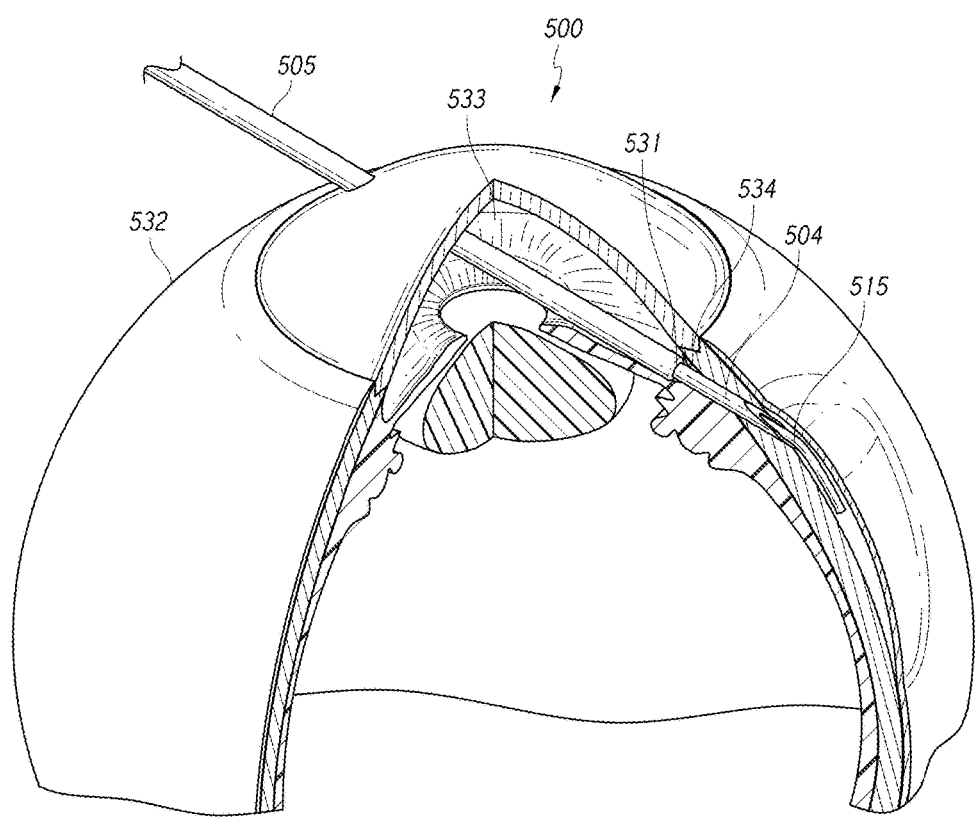
Figure 38D:
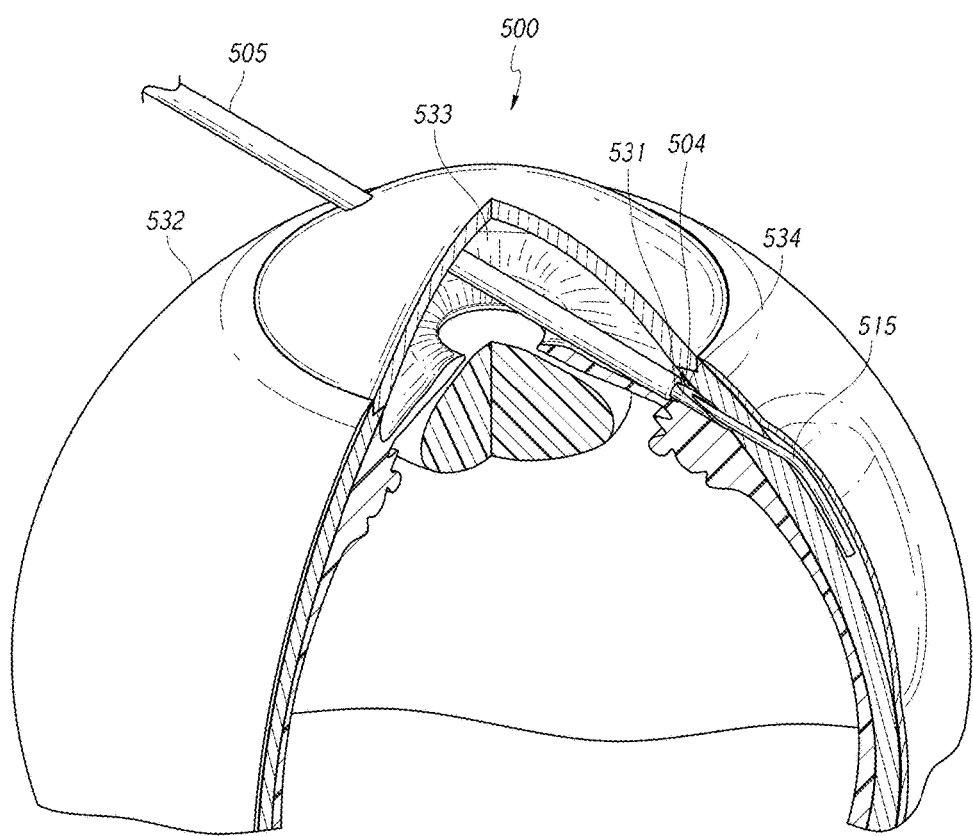
Figure 38E:
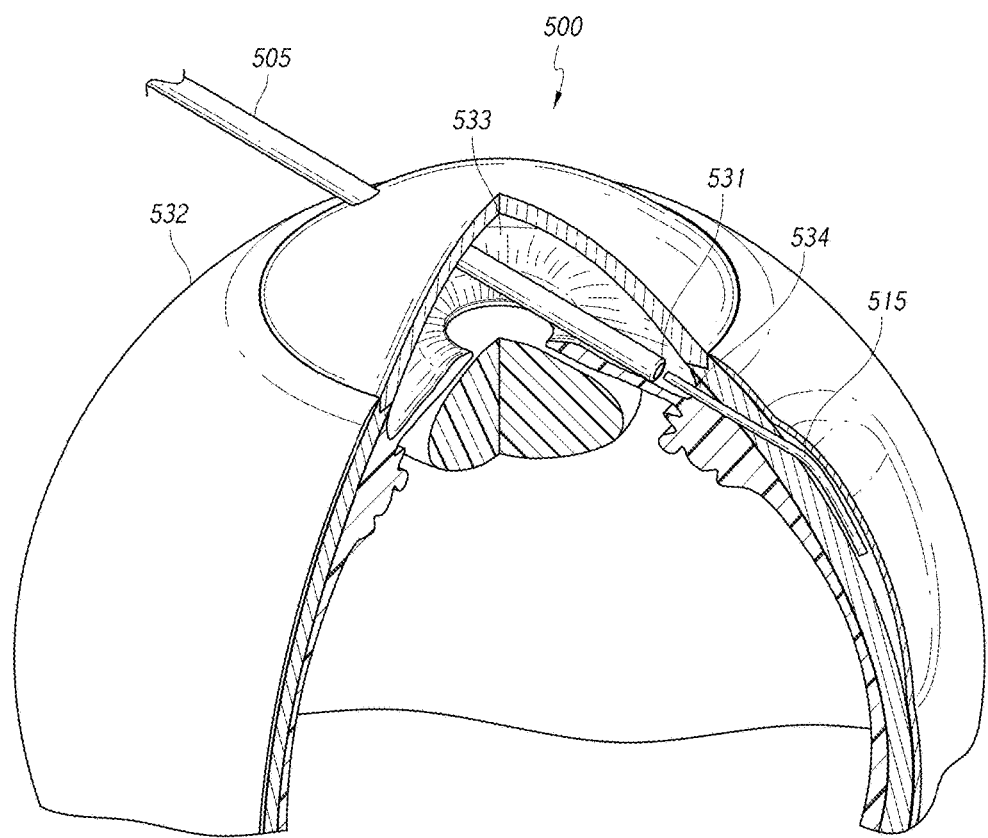

FIG. 37B is a magnified view of the sleeve of the device being removed from the eye.

FIGS. 38A-38E show an intraocular shunt being deployed within the eye, according to another embodiment.

DETAILED DESCRIPTION

The present inventions generally relate to methods for treating closed angle glaucoma that involve using a deployment device that is configured to both re-open a partially or completely closed anterior chamber angle and deploy an intraocular shunt. In certain aspects, some methods involve inserting into an eye a deployment device configured to hold an intraocular shunt, using the device to re-open an at least partially closed anterior chamber angle of an eye, and deploying the shunt from the device.

Figure 1:
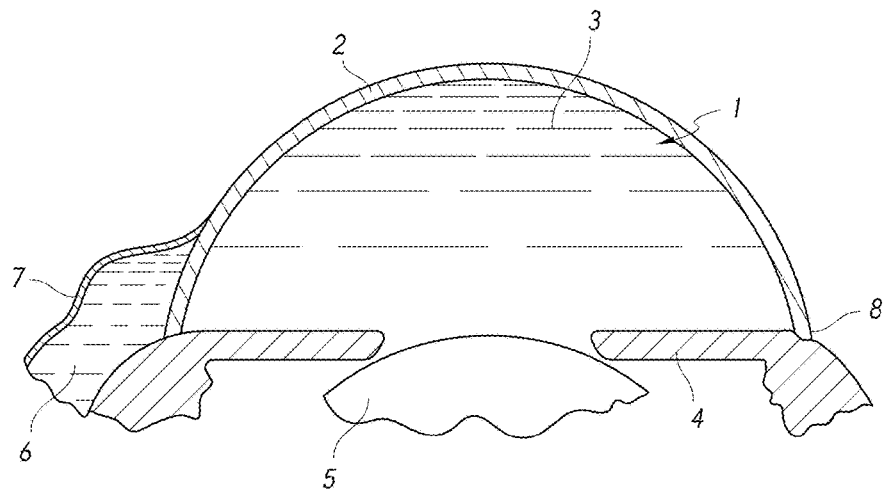
FIG. 1 provides a cross-sectional diagram of the general anatomy of the eye.

FIG. 1 provides a schematic diagram of the general anatomy of the eye. An anterior aspect of the anterior chamber 1 of the eye is the cornea 2, and a posterior aspect of the anterior chamber 1 of the eye is the iris 4. Beneath the iris 4 is the lens 5. The anterior chamber 1 is filled with aqueous humor 3. The aqueous humor 3 drains into a space(s) 6 below the conjunctiva 7 through the trabecular meshwork (not shown in detail) of the sclera 8. The aqueous humor is drained from the space(s) 6 below the conjunctiva 7 through a venous drainage system (not shown).

Figure 2:
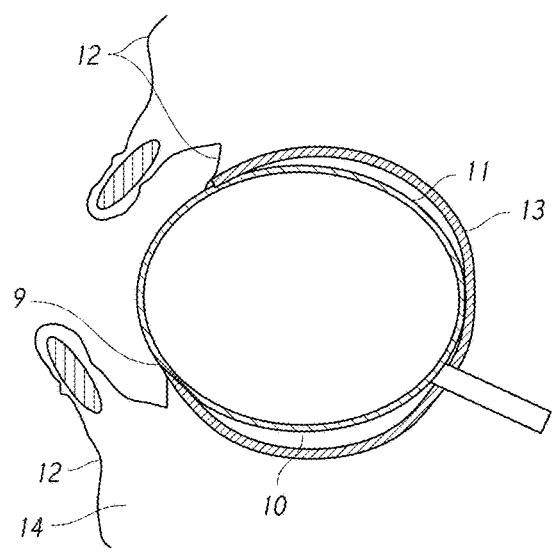
FIG. 2 provides another cross-sectional view the eye, and certain anatomical structures of the eye.

FIG. 2 provides a cross-sectional view of a portion of the eye, and provides greater detail regarding certain anatomical structures of the eye. In particular, FIG. 2 shows the relationship of the conjunctiva 12 and Tenon's capsule 13. Tenon's capsule 13 is a fascial layer of connective tissue surrounding the globe and extra-ocular muscles. As shown in FIG. 2, it is attached anteriorly to the limbus of the eye and extends posteriorly over the surface of the globe until it fuses with the dura surrounding the optic nerve. In FIG. 2, number 9 denotes the limbal fusion of the conjunctiva 12 and Tenon's capsule 13 to the sclera 11. The conjunctiva 12 and Tenon's capsule 13 are separate membranes that start at the limbal fusion 9 and connect to tissue at the posterior of the eye. The space formed below the conjunctiva 12 is referred to as the subconjunctival space, denoted as number 14. Below Tenon's capsule 13 there are Tenon's adhesions that connect the Tenon's capsule 13 to the sclera 11. The space between Tenon's capsule 13 and the sclera 11 where the Tenon's adhesions connect the Tenon's capsule 13 to the sclera 11 is referred to as the intra-Tenon's space, denoted as number 10.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.

Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a fluid-flow pathway between the anterior chamber of the eye and a region of lower pressure. Various structures and/or regions of the eye having lower pressure that have been targeted for aqueous humor drainage include Schlemm's canal, the subconjunctival space, the episcleral vein, the suprachoroidal space, or the subarachnoid space. Methods of implanting intraocular shunts are known in the art. Shunts may be implanted using an ab externo approach (entering through the conjunctiva and inwards through the sclera) or an ab interno approach (entering through the cornea, across the anterior chamber, and through the trabecular meshwork and sclera).

Ab interno approaches for implanting an intraocular shunts have been described and may vary depending on the structure targeted for aqueous humor drainage. For example, ab interno approaches for implanting an intraocular shunt into the subconjunctival space are shown in Yu et al. (U.S. Pat. No. 6,544,249 and U.S. Pat. Pub. No. 2008/0108933) and Prywes (U.S. Pat. No. 6,007,511), the contents of each of which are incorporated by reference herein in its entirety. Briefly and with reference to FIG. 3, a surgical intervention to implant the shunt involves inserting into the eye a portion of a deployment device 15 that holds an intraocular shunt, and deploying the shunt within the eye 16. The portion of the deployment device 15 holding the shunt enters the eye 16 through the cornea 17 (ab interno approach). The portion of the deployment device 15 is advanced across the anterior chamber 20 (as depicted by the broken line) in what is referred to as a transpupil implant insertion. The portion of the deployment device 15 is advanced through the sclera 21 until a distal portion of the device is in proximity to the subconjunctival space. The shunt is then deployed from the deployment device, producing a conduit between the anterior chamber and the subconjunctival space to allow aqueous humor to drain through the conjunctival lymphatic system.

Figure 3:
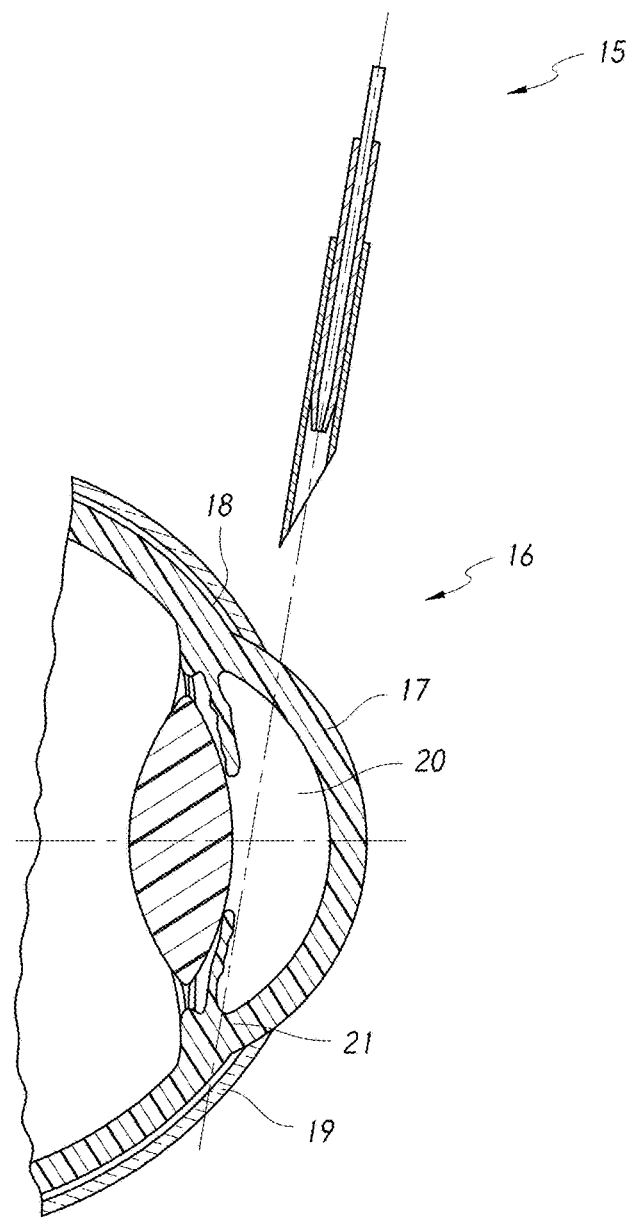
FIG. 3 depicts, implantation of an intraocular shunt with a distal end of a deployment device holding a shunt, shown in cross-section.
Figure 4A:
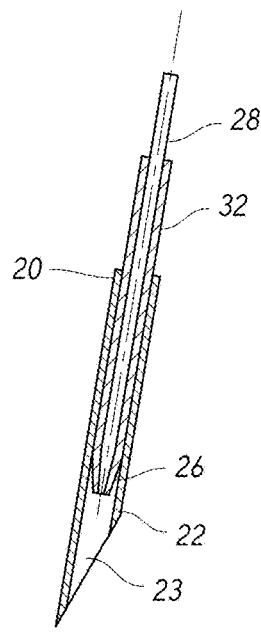
FIGS. 4A-4B depict a deployment device having a plunger type mechanism for deploying an intraocular shunt into the eye.
Figure 4B:
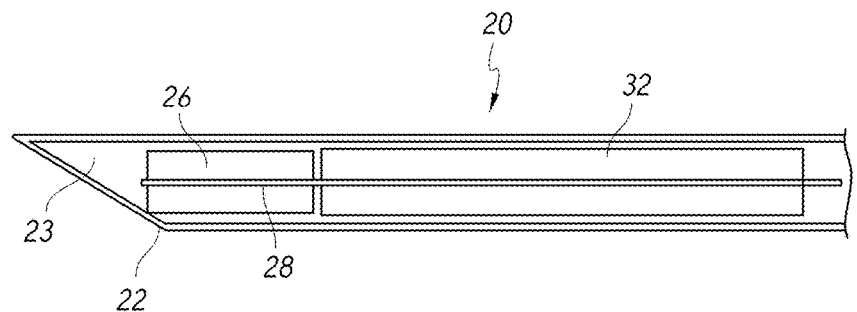

Previously proposed deployment devices for implanting an intraocular shunt into the eye, whether using an ab externo procedure or an ab interno procedure, typically include a plunger-type mechanism for deploying the shunt into the eye, such as the deployment device illustrated in FIG. 3. The deployment device in FIG. 3 is shown larger in FIG. 4A, and the distal portion of the deployment device is shown magnified in FIG. 4B. As shown in FIGS. 4A and 4B, the deployment device includes an assembly 20 that includes a hollow shaft 22 defining an inner chamber 24. Placed within the inner chamber 24 of the hollow shaft 22 is a cylindrical inner tube or plunger 32 that is coaxial with the shaft 22. In the loaded and ready to use condition, the intraocular shunt 26 is also placed or otherwise disposed within the hollow inner chamber 24 of the shaft 22 and is distally located relative to plunger 32. Both the intraocular shunt 26 and plunger 32 may be placed over and supported by optional guidewire 28. The intraocular shunt is deployed into the eye by advancing the plunger to push the intraocular shunt from the shaft into the eye. The shaft is then withdrawn from the eye.

However, complications can arise when using such deployment devices due to the frictional interaction between the deployment device and the surrounding eye tissue that results upon insertion of the deployment device into the eye and/or deployment of the intraocular shunt into the eye from the deployment device. Moderate to severe eye trauma can occur, beyond any trauma due to insertion of the deployment device, if the portion of the deployment device inserted into the eye is not loosened before or after deployment of the intraocular shunt from the device and prior to withdrawing the portion of the deployment device from the eye.

The present inventions provide improved methods for implanting an intraocular shunt into the eye while avoiding or at least minimizing the amount of trauma to the eye that is typically involved with shunt implantation procedures. According to some methods, any frictional resistance between the deployment device and surrounding eye tissue that is created upon insertion of a portion of a deployment device in the eye is resolved by loosening the portion of the deployment device from the surrounding eye tissue before or after deployment of the intraocular shunt from the device and prior to withdrawing the portion of the deployment device from the eye. The methods can be used in conjunction with any known shunt deployment device, and in particular, any deployment device that includes a portion for holding an intraocular shunt or is coupled to a hollow shaft which is configured to hold an intraocular shunt.

Preferably, at least a portion of the deployment device is rotated before the shunt is deployed into the eye from the deployment device, in order to loosen the portion of the device inserted into the eye from the surrounding eye tissue prior to withdrawing the deployment device from the eye. Rotation may be clockwise or counterclockwise, and may be performed manually or in an automated manner. Rotation of only a distal portion of the deployment device may be sufficient to loosen the portion of the deployment device in the eye from the surrounding eye tissue, depending on the configuration of the device. Alternatively, rotation of the entire deployment device serves to loosen the portion of the deployment device in the eye from the surrounding eye tissue. Rotation of the deployment device, or a portion thereof, causes the portion of the deployment device that is inserted into the eye to also rotate, thereby loosening the portion of the deployment device in the eye form the surrounding eye tissue. Examples of surrounding eye tissue include but are not limited to the scleral tissue and the trabecular meshwork.

The deployment device, or a portion thereof, is rotated clockwise or counterclockwise about the longitudinal axis of the deployment device itself. The rotation about the longitudinal axis is preferably between 1° and 360°, or any specific value within said range, e.g., 1°, 3°, 5°, 10°, 15°, 30°, 45°, 60°, 75°, 90°, 105°, 120°, 135°, 150° 165°, 180°, 195°, 210°, 225°, 240°, 255°, 270°, 285°, 300°, 315°, 330°, 345° or 360°.

Figure 5:
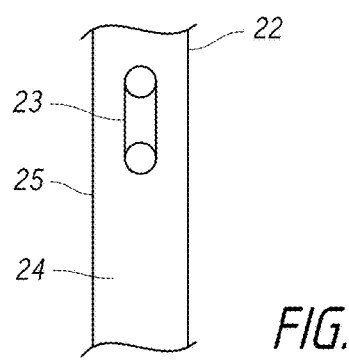
FIG. 5 depicts an example of a deployment device configured to hold an intraocular shunt.

As previously stated, some methods can be used in conjunction with any shunt deployment device. FIG. 5 provides an exemplary schematic of a hollow shaft for use in conjunction with a deployment device in accordance with some methods. This shows hollow shaft 22 that is configured to hold an intraocular shunt 23. The shaft may hold the shunt within the hollow interior 24 of the shaft 22. Alternatively, the hollow shaft may hold the shunt on an outer surface 25 of the shaft 22. In particular embodiments, the shunt is held within the hollow interior 24 of the shaft 22. Generally, in one embodiment, the intraocular shunts are of a cylindrical shape and have an outside cylindrical wall and a hollow interior. The shunt may have an inside diameter of approximately 10-250 microns, an outside diameter of approximately 190-300 microns, and a length of approximately 0.5 mm to 20 mm, such as, for example, 6 mm to 14 mm. The hollow shaft 22 is configured to at least hold a shunt of such shape and such dimensions. However, the hollow shaft 22 may be configured to hold shunts of different shapes and different dimensions than those described above, and some embodiments encompass a shaft 22 that may be configured to hold any shaped or dimensioned intraocular shunt.

Figure 6A:
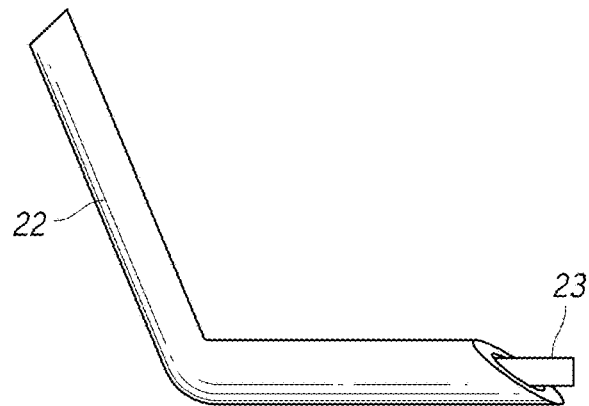
FIG. 6A depicts a hollow shaft having a bend in a distal portion of the shaft.
Figure 6B:
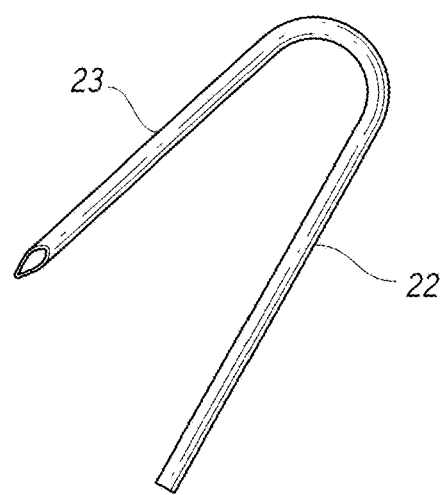
FIG. 6B depicts a hollow shaft having a U-shape.
Figure 6C:
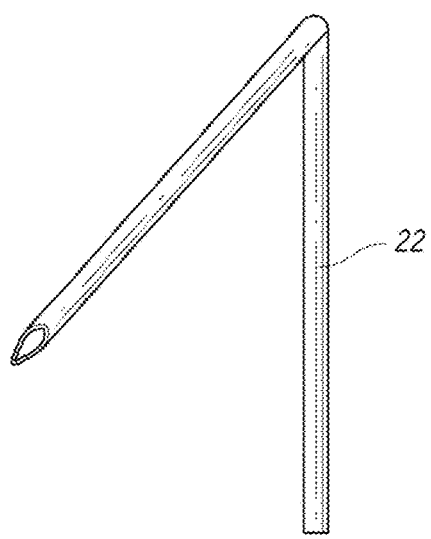
FIG. 6C depicts a hollow shaft having a V-shape.

In some embodiments, the hollow shaft for use in accordance with some methods is straight along the entire length of the shaft. Alternatively, a portion of the hollow shaft extends linearly along a longitudinal axis and at least one other portion of the shaft extends off the longitudinal axis. For example, the hollow shaft may have a bend in the distal portion of the shaft, a U-shape, or an arcuate or V-shape in at least a portion of the shaft. Examples of such hollow shafts suitable for use with some methods include but are not limited to the hollow shafts depicted in FIGS. 6A-6C.

Preferably, some methods are conducted by making an incision in the eye prior to insertion of the deployment device configured to hold the intraocular shunt. Although in particular embodiments, some methods may be conducted without making an incision in the eye prior to insertion of the deployment device configured to hold the intraocular shunt. In certain embodiments, the distal end of the deployment device (i.e. the portion that is inserted into the eye) has a sharpened point or tip. For example, the distal end of the deployment device includes or is coupled to a needle configured to hold an intraocular shunt. Needles that are configured to hold an intraocular shunt are commercially available from Terumo Medical Corp. (Elkington Md.). In a particular embodiment, the distal end of the deployment device is coupled to a needle having a hollow interior and a beveled tip, and the intraocular shunt is held within the hollow interior of the needle. In another particular embodiment, the distal end of the deployment device is coupled to a needle having a hollow interior and a triple ground point or tip.

Some methods are preferably conducted without needing to remove an anatomical portion or feature of the eye, including but not limited to the trabecular meshwork, the iris, the cornea, or aqueous humor. Some methods are also preferably conducting without inducing substantial ocular inflammation, such as subconjunctival blebbing or endophthalmitis. Such methods are preferably achieved using an ab interno approach by inserting the deployment device comprising the intraocular shunt through the cornea, across the anterior chamber, through the trabecular meshwork and sclera and into a drainage structure such as Schlemm's canal, the subconjunctival space, the episcleral vein, the suprachoroidal space, the intra-Tenon's space or the subarachnoid space. However, some methods may be conducted using an ab externo approach.

When some methods are conducted using an ab interno approach, the deployment device is preferably inserted into the eye at an angle above or below the corneal limbus, inserted in contrast with entering through the corneal limbus. Preferably, the deployment device is inserted above the corneal limbus. For example, the deployment device is inserted approximately 0.25 to 3.0 mm, preferably approximately 0.5 to 2.5 mm, more preferably approximately 1.0 mm to 2.0 mm above the corneal limbus, or any specific value within said ranges, e.g., approximately 1.0 mm, approximately 1.1 mm, approximately 1.2 mm, approximately 1.3 mm, approximately 1.4 mm, approximately 1.5 mm, approximately 1.6 mm, approximately 1.7 mm, approximately 1.8 mm, approximately 1.9 mm or approximately 2.0 mm above the corneal limbus.

Figure 7A:
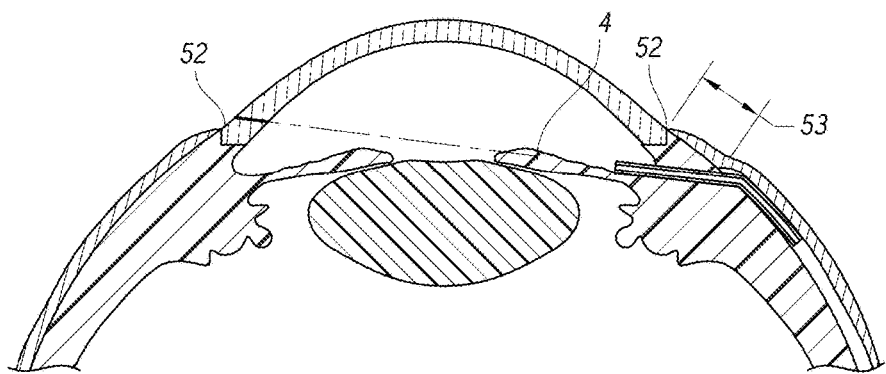
FIG. 7A depicts a simulation of the exit site distance from the limbus and height above the iris after needle entry at the limbus using an ab interno procedure.

Entering at an angle above or below the corneal limbus is advantageous for placing the shunt farther from the limbus at the exit site. It also adds more distance between the shunt and the iris. FIG. 7A demonstrates the change in location of the shunt sclera exit and the height above the iris in the chamber at different angles of entry using a hollow needle configured to hold an intraocular shunt.

Without intending to be bound by any theory, placement of the shunt farther from the limbus at the exit site, as provided by an angle of entry above the limbus, is believed to provide access to more lymphatic channels for drainage of aqueous humor, such as the episcleral lymphatic network, in addition to the conjunctival lymphatic system. A higher angle of entry also results in flatter placement in the intra-Tenon's space so that there is less bending of the shunt, less pressure on Tenon's capsule, and subsequently less erosion pressure on the conjunctiva via Tenon's capsule.

Figure 7B:
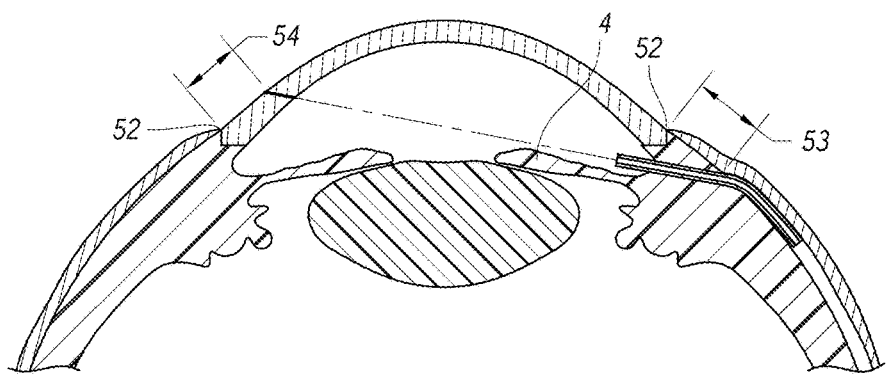
FIG. 7B depicts a simulation of the exit site distance from the limbus and height above the iris after needle entry above the limbus using an ab interno procedure.

For example, as shown in FIG. 7A, shaft entry at the limbus 52 results in exit site distance 53 of approximately 1.6 mm from the limbus, and very close proximity to the iris 4. Such placement results in a large degree of bending of the shunt, resulting in increased pressure on Tenon's capsule and subsequently on the conjunctiva. In contrast, a high angle of entry 54 above the limbus 52 (e.g., 2 mm above the limbus 52), results in an exit site distance 53 of approximately 2.1 mm from the limbus and a height well above the iris 4, as shown in FIG. 7B. Such placement results in flatter placement in the intra-Tenon's space so that there is less bending of the shunt, less pressure on Tenon's capsule, and subsequently less erosion pressure on the conjunctiva via Tenon's capsule.

Deployment of an intraocular shunt in the eye in accordance with some methods results in the formation of a passage that directs fluid flow from an area of high pressure in the eye, typically the anterior chamber, to an area of lower pressure within the eye or within the head, to relieve or reduce intraocular pressure. Areas of lower pressure within the eye that are suited for aqueous humor drainage include but are not limited to the intra-Tenon's space, the subconjunctival space, the episceleral vein, the suprachoroidal space and Schlemm's canal. Alternatively, the subarachnoid space may provide a drainage outlet for aqueous humor from the anterior chamber. Preferably, deployment of the shunt results in the formation of a passage for directing fluid flow between the anterior chamber and the intra-Tenon's space.

Deployment of an intraocular shunt such that the inlet (i.e., the portion of the shunt that receives fluid from an anterior chamber of the eye) terminates in the anterior chamber and the outlet (i.e., the portion of the shunt that directs fluid to the intra-Tenon's space) terminates in the intra-Tenon's space provides superior benefits over deployment generally in the subconjunctival space. Deployment of the shunt outlet in the intra-Tenon's space safeguards the integrity of the conjunctiva to allow subconjunctival drainage pathways to successfully form. See, for example, Yu et al., Progress in Retinal and Eye Research, 28: 303-328 (2009)). Additionally, drainage into the intra-Tenon's space provides access to more lymphatic channels than just the conjunctival lymphatic system, such as the episcleral lymphatic network. Moreover, deployment of an intraocular shunt such that the outlet terminates in the intra-Tenon's space avoids having to pierce Tenon's capsule which can otherwise cause complications during glaucoma filtration surgery due to its tough and fibrous nature.

Methods for Intra-Tenon's Shunt Placement

Some methods involve inserting into the eye a hollow shaft configured to hold an intraocular shunt. In certain embodiments, the hollow shaft is a component of a deployment device that may deploy the intraocular shunt. The shunt is then deployed from the shaft into the eye such that the shunt forms a passage from the anterior chamber to the intra-Tenon's space. The hollow shaft is then withdrawn from the eye.

Figure 8:
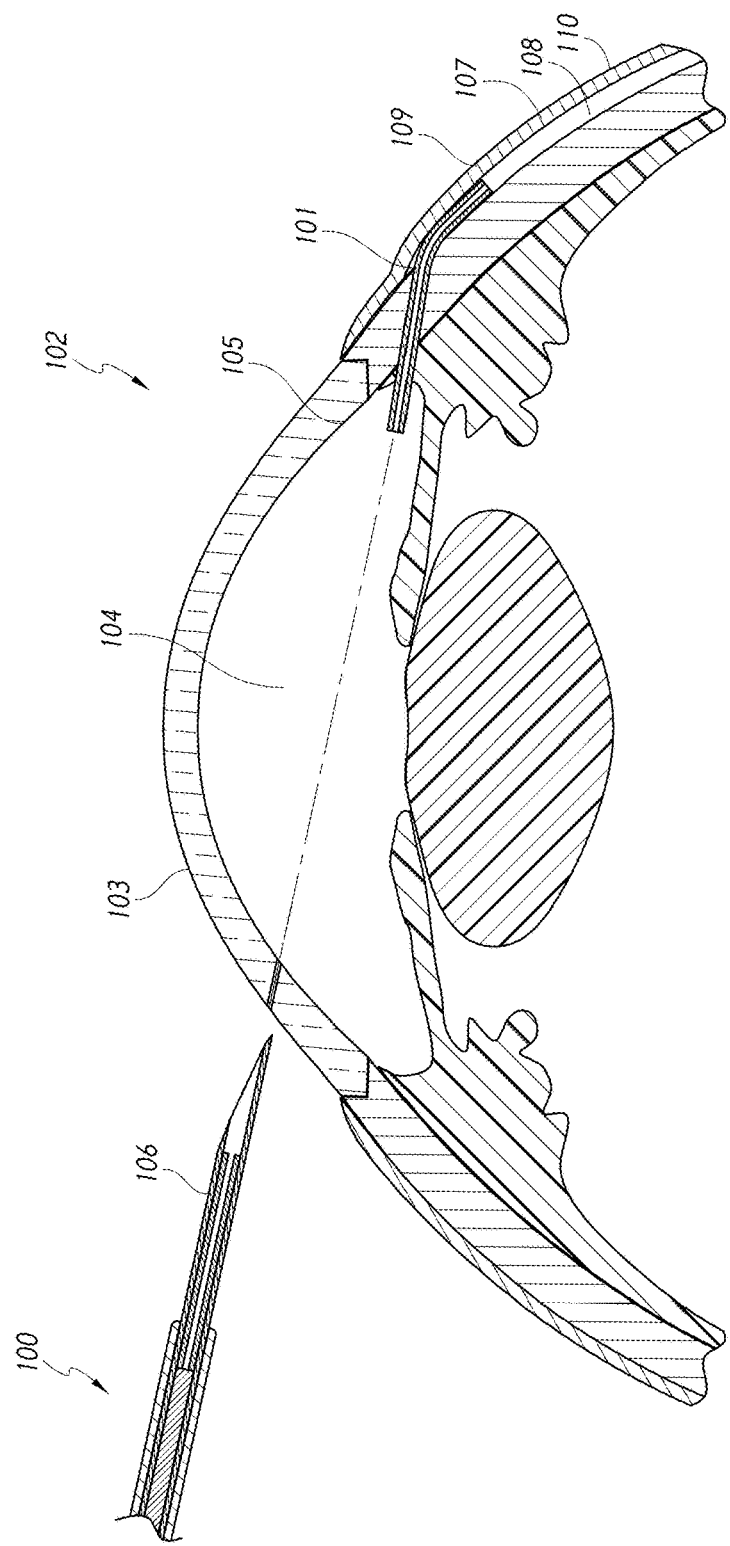
FIGS. 8 and 9 show an intraocular shunt deployed within the eye. A proximal portion of the shunt resides within the intra-Tenon's space. A middle portion of the shunt resides in the sclera.
Figure 9:
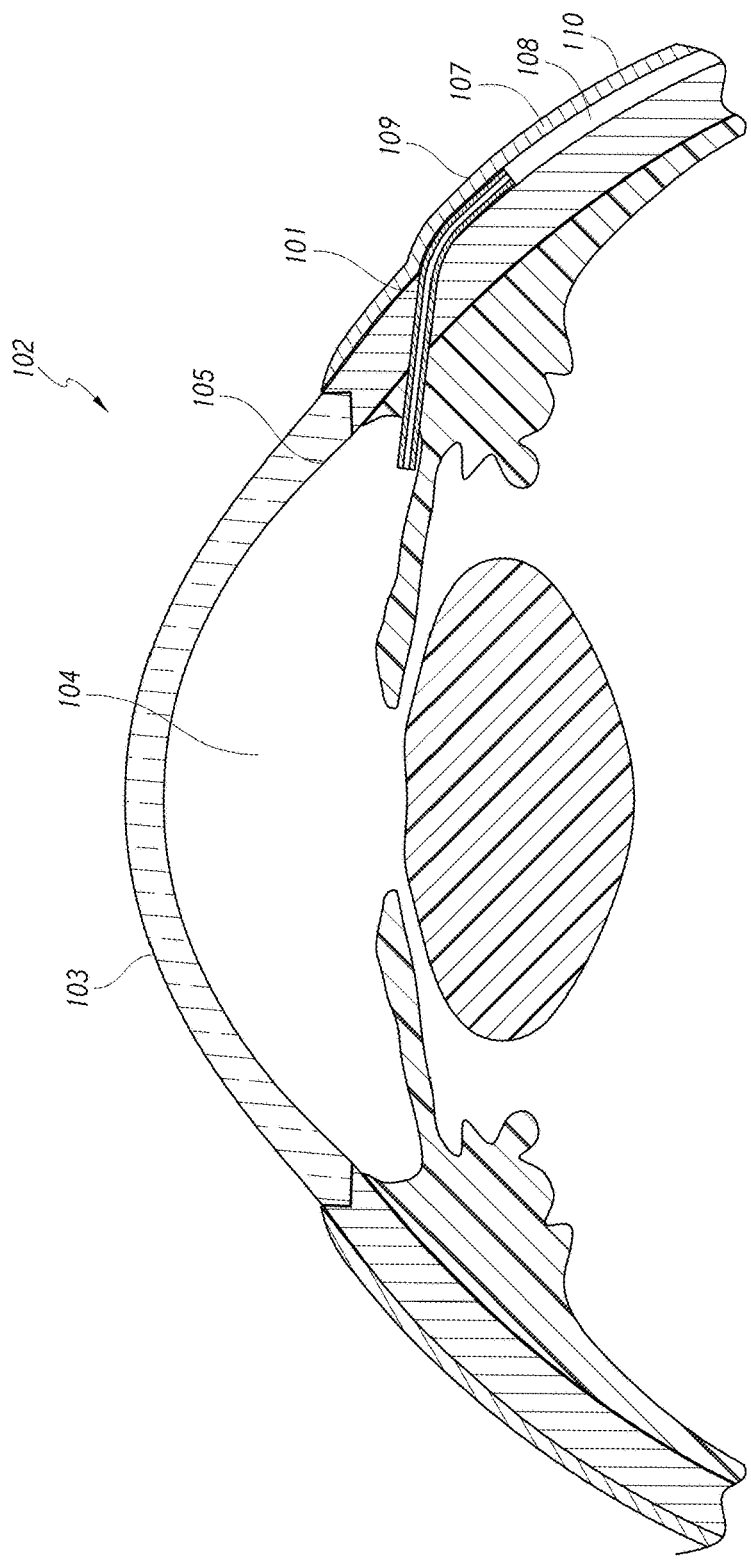

Referring to FIGS. 8 and 9, which show an intraocular shunt placed into the eye such that the shunt forms a passage for fluid drainage from the anterior chamber to the intra-Tenon's space. To place the shunt within the eye, a surgical intervention to implant the shunt is preformed that involves inserting into the eye 102 a deployment device 100 that holds an intraocular shunt 101, and deploying at least a portion of the shunt 101 within intra-Tenon's space 108, within subconjunctival space 109 beneath the conjunctiva 110. In certain embodiments, a hollow shaft 106 of a deployment device 100 holding the shunt 101 enters the eye 102 through the cornea 103 (ab interno approach). The shaft 106 is advanced across the anterior chamber 104 (as depicted by the broken line) in what is referred to as a transpupil implant insertion. The shaft 106 is advanced through the sclera 105 until a distal portion of the shaft 106 is in proximity to Tenon's capsule 107. After piercing the sclera 105 with the hollow shaft 106 of the deployment device 100, resistance to advancement of the shaft 106 encountered by an operator of the deployment device 100 informs the operator that the shaft 106 has contacted Tenon's capsule 107 and is thus in proximity to Tenon's capsule 107.

Numerous techniques may be employed to ensure that after piercing the sclera 105, the hollow shaft 106 does not pierce Tenon's capsule 107. In certain embodiments, some methods involve the use of a hollow shaft 106, in which a portion of the hollow shaft extends linearly along a longitudinal axis and at least one other portion of the shaft extends off the longitudinal axis. For example, the hollow shaft 106 may have a bend in the distal portion of the shaft, a U-shape, or an arcuate or V-shape in at least a portion of the shaft. Examples of such hollow shafts 106 suitable for use with some methods include but are not limited to the hollow shafts 106 depicted in FIGS. 6A-6C. In embodiments in which the hollow shaft 106 has a bend at a distal portion of the shaft, intra-Tenon's shunt placement can be achieved by using the bent distal portion of the shaft 106 to push Tenon's capsule 107 away from the sclera 105 without penetrating Tenon's capsule 107. In these embodiments, the tip of the distal end of the shaft 106 does not contact Tenon's capsule 107.

In other embodiments, a straight hollow shaft 106 having a beveled tip is employed. The angle of the beveled tip of the hollow shaft is configured such that after piercing the sclera 105, the hollow shaft 106 does not pierce Tenon's capsule 107. In these embodiments, the shaft 106 is inserted into the eye 102 and through the sclera 105 at an angle such that the bevel of the tip is parallel to Tenon's capsule 107, thereby pushing Tenon's capsule 107 away from the sclera 105, rather than penetrating Tenon's capsule 107, and allowing for deployment of a distal portion of the shunt 101 into the intra-Tenon's space 108.

Once a distal portion of the hollow shaft 106 is within the intra-Tenon's space 108, at least a portion of the device is rotated, thereby reducing the friction between the portion of the device that is in contact with the scleral tissue and the scleral tissue itself. Reduction in friction allows for deployment of the shunt from the device and then removal of the device from the eye without disturbing the tissue of the eye. After rotating the device, the shunt 101 is then deployed from the shaft 106 of the deployment device 100, producing a conduit between the anterior chamber 104 and the intra-Tenon's space 108 to allow aqueous humor to drain from the anterior chamber 104 (See FIGS. 8 and 9).

In another embodiment, some methods further involves injecting an aqueous solution into the eye below Tenon's capsule in order to balloon the capsule away from the sclera. The increase in intra-Tenon's space caused by the ballooning of Tenon's capsule is helpful for positioning of the outlet of the shunt in the intra-Tenon's space. The solution is injected prior to the shaft piercing the sclera and entering the intra-Tenon's space. Suitable aqueous solutions include but are not limited to Dulbecco's Phosphate Buffered Saline (DPBS), Hank's Balanced Salt Solution (HBSS), Phosphate-Buffered Saline (PBS), Earle's Balanced Salt Solution (EBSS), or other balanced salt solutions known in the art. In some embodiments, some methods involve injecting a viscoelastic fluid into the eye. Preferably, some methods are conducted without the use of a viscoelastic fluid. Some methods can be conducted using any shunt deployment device known in the art. Examples of deployment devices that are suitable for use with some methods include but are not limited to the devices described in U.S. Pat. No. 6,007,511, U.S. Pat. No. 6,544,249, and U.S. Pat. Pub. No. US2008/0108933, the contents of each of which are hereby incorporated by reference in their entireties.

Figure 10A:
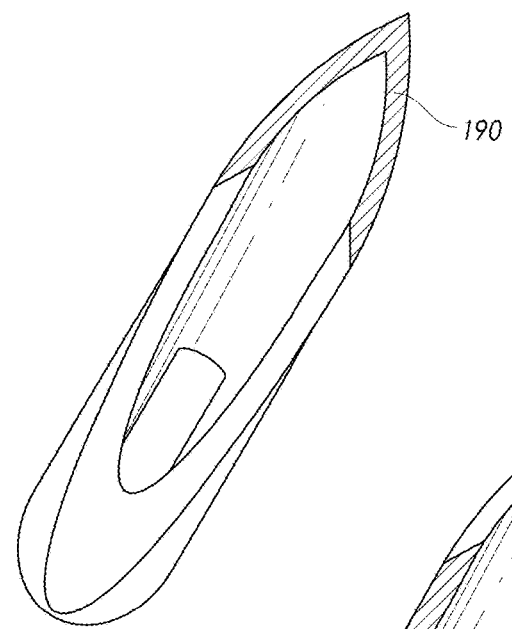
FIG. 10A depicts the tip bevel portion of a triple-ground needle tip.
Figure 10B:
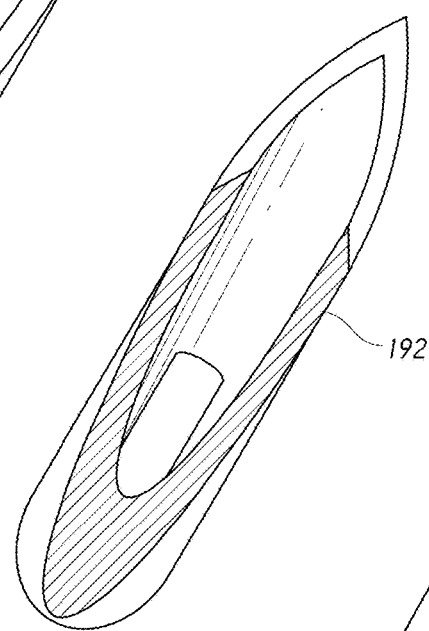
FIG. 10B depicts the flat bevel portion of a triple-ground needle tip.
Figure 10C:
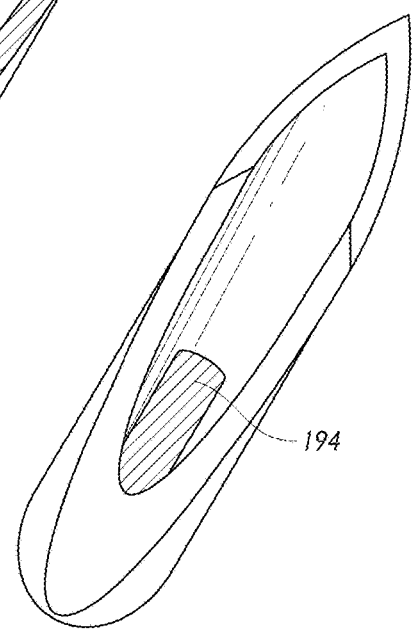
FIG. 10C depicts an intraocular shunt within a triple-ground needle tip.
Figure 10D:
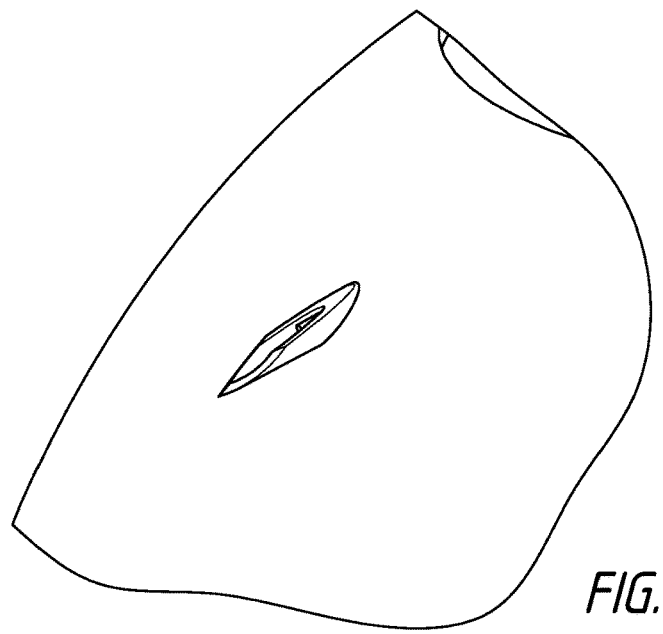
FIG. 10D depicts 100% penetration of the flat bevel portion of a triple-ground needle tip through the sclera of an eye.

In certain embodiments, to ensure proper positioning and functioning of the intraocular shunt, the depth of penetration through the sclera is important when conducting some methods. In one embodiment, the distal tip of the hollow shaft pierces the sclera without coring, removing or causing major tissue distortion of the surrounding eye tissue. The shunt is then deployed from the shaft. Preferably, a distal portion of the hollow shaft (as opposed to the distal tip) completely penetrates the sclera before the shunt is deployed from the hollow shaft. In certain embodiments, the hollow shaft is a flat bevel needle, such as a needle having a triple-ground point. The tip bevel first pierces through the sclera making a horizontal slit. In a preferred embodiment of some methods, the needle is advanced even further such that the entire flat bevel penetrates through the sclera, as shown in FIG. 10D, to spread and open the tissue to a full circular diameter. The tip bevel portion 190 and flat bevel portion 192 of a triple ground needle point, and the configuration of the shunt 194 disposed in the needle point, are exemplified as the gray shaded areas in FIGS. 10A-10C. Without intending to be bound by any theory, if the scleral channel is not completely forced open by the flat bevel portion of the needle, the material around the opening may not be sufficiently stretched and a pinching of the implant in that zone will likely occur, causing the shunt to fail. Full penetration of the flat bevel through the sclera causes minor distortion and trauma to the local area. However, this area ultimately surrounds and conforms to the shunt once the shunt is deployed in the eye.

Figure 11A:
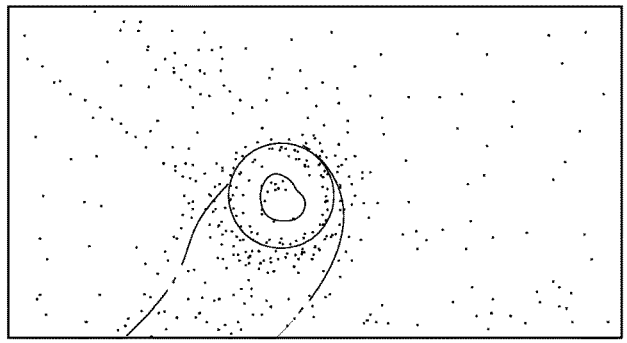
FIG. 11A depicts an intraocular shunt inserted into the scleral channel using a beveled needle tip to completely penetrate the scleral tissue prior to insertion of the shunt.
Figure 11B:
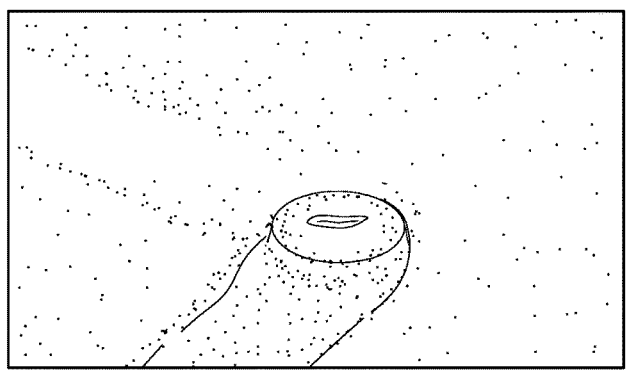
FIG. 11B depicts an intraocular shunt inserted into the scleral channel using a beveled needle tip to partially penetrate the scleral tissue prior to insertion of the shunt.

FIG. 11A depicts an example of an intraocular shunt implanted in an eye in accordance with some methods using a triple ground need point with 100% penetration of the flat bevel in the scleral channel. FIG. 11B depicts an example of a shunt implanted in an eye in accordance with some methods using a triple ground needle point with approximately 50% penetration of the flat bevel in the scleral channel. As shown in FIG. 11B, the shunt is almost completely pinched off as compared to the open shunt depicted in FIG. 11A.

Some methods may be conducted using any commercially available shunts, such as the Optonol Ex-PRESS mini Glaucoma shunt, and the Solx DeepLight Gold Micro-Shunt. However, some methods are preferably conducted using the intraocular shunts of some embodiments, as described herein.

Intraocular Shunts

The present inventions also provide intraocular shunts that are configured to form a drainage pathway from the anterior chamber of the eye to the intra-Tenon's space. In particular, the intraocular some embodiments of the shunt have a length that is sufficient to form a drainage pathway from the anterior chamber of the eye to the intra-Tenon's space. The length of the shunt is important in achieving placement specifically in the intra-Tenon's space. A shunt that is too long will extend beyond the intra-Tenon's space and irritate the conjunctiva, which can cause the filtration procedure to fail, as previously described. A shunt that is too short will not provide sufficient access to drainage pathways such as the episcleral lymphatic system or the conjunctival lymphatic system.

Some embodiments of the shunt may be any length that allows for drainage of aqueous humor from an anterior chamber of an eye to the intra-tenon's space. Exemplary shunts range in length from approximately 0.5 mm to approximately 20 mm or between approximately 4 mm to approximately 16 mm, or any specific value within said ranges. In certain embodiments, the length of the shunt is between approximately 6 to 8 mm, or any specific value within said range, e.g., 6.0 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm. 7.9 mm, or 8.0 mm.

The intraocular some embodiments of the shunt are particularly suitable for use in an ab interno glaucoma filtration procedure. Commercially available shunts that are currently used in ab interno filtration procedures are typically made of a hard, inflexible material such as gold, polymer, titanium, or stainless steel, and cause substantial irritation of the eye tissue, resulting in ocular inflammation such as subconjunctival blebbing or endophthalmitis. In contrast, the intraocular some embodiments of the shunt are flexible, and have an elasticity modulus that is substantially identical to the elasticity modulus of the surrounding tissue in the implant site. As such, the intraocular some embodiments of the shunt are easily bendable, do not erode or cause a tissue reaction, and do not migrate once implanted. Thus, when implanted in the eye using an ab interno procedure, such as the methods described herein, the intraocular some embodiments of the shunt do not induce substantial ocular inflammation such as subconjunctival blebbing or endophthalmitis. Additional exemplary features of the intraocular some embodiments of the shunt are discussed in further detail below.

Tissue Compatible Shunts

In certain aspects, some embodiments generally provide shunts composed of a material that has an elasticity modulus that is compatible with an elasticity modulus of tissue surrounding the shunt (e.g., tissue surrounding the suprachoroidal space). In this manner, some embodiments of the shunt are flexibility matched with the surrounding tissue, and thus will remain in place after implantation without the need for any type of anchor that interacts with the surrounding tissue. Consequently, some embodiments of the shunt will maintain fluid flow away for an anterior chamber of the eye after implantation without causing irritation or inflammation to the tissue surrounding the eye.

Elastic modulus, or modulus of elasticity, is a mathematical description of an object or substance's tendency to be deformed elastically when a force is applied to it. The elastic modulus of an object is defined as the slope of its stress-strain curve in the elastic deformation region:

$$\lambda \stackrel{def}{=} \frac{Stress}{Strain}$$

where lambda ($\lambda$) is the elastic modulus; stress is the force causing the deformation divided by the area to which the force is applied; and strain is the ratio of the change caused by the stress to the original state of the object. The elasticity modulus may also be known as Young's modulus (E), which describes tensile elasticity, or the tendency of an object to deform along an axis when opposing forces are applied along that axis. Young's modulus is defined as the ratio of tensile stress to tensile strain. For further description regarding elasticity modulus and Young's modulus, see for example Gere (Mechanics of Materials, 6th Edition, 2004, Thomson), the content of which is incorporated by reference herein in its entirety.

The elasticity modulus of any tissue can be determined by one of skill in the art. See for example Samani et al. (Phys. Med. Biol. 48:2183, 2003); Erkamp et al. (Measuring The Elastic Modulus Of Small Tissue Samples, Biomedical Engineering Department and Electrical Engineering and Computer Science Department University of Michigan Ann Arbor, Mich. 48109-2125; and Institute of Mathematical Problems in Biology Russian Academy of Sciences, Pushchino, Moscow Region 142292 Russia); Chen et al. (IEEE Trans. Ultrason. Ferroelec. Freq. Control 43:191-194, 1996); Hall, (In 1996 Ultrasonics Symposium Proc., pp. 1193-1196, IEEE Cat. No. 96CH35993, IEEE, New York, 1996); and Parker (Ultrasound Med. Biol. 16:241-246, 1990), each of which provides methods of determining the elasticity modulus of body tissues. The content of each of these is incorporated by reference herein in its entirety.

The elasticity modulus of tissues of different organs is known in the art. For example, Pierscionek et al. (Br J Ophthalmol, 91:801-803, 2007) and Friberg (Experimental Eye Research, 473:429-436, 1988) show the elasticity modulus of the cornea and the sclera of the eye. The content of each of these references is incorporated by reference herein in its entirety. Chen, Hall, and Parker show the elasticity modulus of different muscles and the liver. Erkamp shows the elasticity modulus of the kidney.

Some embodiments of the shunt are composed of a material that is compatible with an elasticity modulus of tissue surrounding the shunt. In certain embodiments, the material has an elasticity modulus that is substantially identical to the elasticity modulus of the tissue surrounding the shunt. In other embodiments, the material has an elasticity modulus that is greater than the elasticity modulus of the tissue surrounding the shunt. Exemplary materials includes biocompatible polymers, such as polycarbonate, polyethylene, polyethylene terephthalate, polyimide, polystyrene, polypropylene, poly(styrene-b-isobutylene-b-styrene), or silicone rubber.

In particular embodiments, some embodiments of the shunt are composed of a material that has an elasticity modulus that is compatible with the elasticity modulus of tissue in the eye, particularly scleral tissue. In certain embodiments, compatible materials are those materials that are softer than scleral tissue or marginally harder than scleral tissue, yet soft enough to prohibit shunt migration. The elasticity modulus for anterior scleral tissue is approximately $2.9\pm1.4\times10^6$ N/m2, and $1.8\pm1.1\times10^6$ N/m2 for posterior scleral tissue. See Friberg (Experimental Eye Research, 473:429-436, 1988). An exemplary material is cross linked gelatin derived from Bovine or Porcine Collagen.

Some embodiments encompasses shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 μm to approximately 250 μm, an outside diameter from diameter from approximately 100 μm to approximately 450 μm, such as approximately 190 μm to approximately 300 μm, and a length from approximately 0.5 mm to approximately 20 mm, such as from approximately 2 mm to approximately 10 mm.

Shunts Reactive to Pressure

Figure 12:
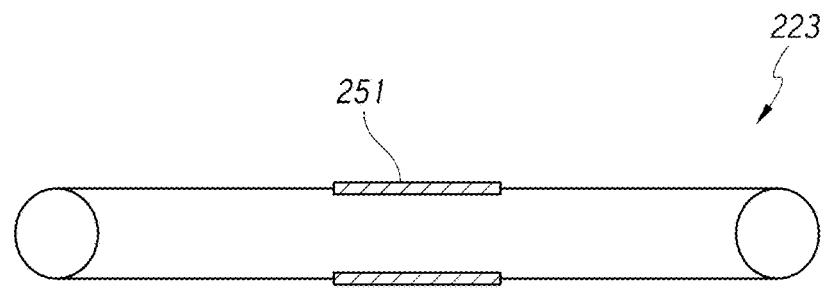
FIG. 12 provides a schematic of a shunt having a flexible portion.

In other aspects, some embodiments generally provide shunts in which a portion of the shunt is composed of a flexible material that is reactive to pressure, i.e., the diameter of the flexible portion of the shunt fluctuates depending upon the pressures exerted on that portion of the shunt. FIG. 12 provides a schematic of a shunt 223 having a flexible portion 251. In this figure, the flexible portion 251 is shown in the middle of the shunt 223. However, the flexible portion 251 may be located in any portion of the shunt, such as the proximal or distal portion of the shunt. In certain embodiments, the entire shunt is composed of the flexible material, and thus the entire shunt is flexible and reactive to pressure.

The flexible portion 251 of the shunt 223 acts as a valve that regulates fluid flow through the shunt. The human eye produces aqueous humor at a rate of about 2 μl/min for approximately 3 ml/day. The entire aqueous volume is about 0.25 ml. When the pressure in the anterior chamber falls after surgery to about 7-8 mmHg, it is assumed the majority of the aqueous humor is exiting the eye through the implant since venous backpressure prevents any significant outflow through normal drainage structures (e.g., the trabecular meshwork).

After implantation, intraocular shunts have pressure exerted upon them by tissues surrounding the shunt (e.g., scleral tissue such as the sclera channel and the sclera exit) and pressure exerted upon them by aqueous humor flowing through the shunt. The flow through the shunt, and thus the pressure exerted by the fluid on the shunt, is calculated by the equation:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

where $\Phi$ is the volumetric flow rate; V is a volume of the liquid poured (cubic meters); t is the time (seconds); v is mean fluid velocity along the length of the tube (meters/second); x is a distance in direction of flow (meters); R is the internal radius of the tube (meters); $\Delta P$ is the pressure difference between the two ends (pascals); 11 is the dynamic fluid viscosity (pascal-second (Pa·s)); and L is the total length of the tube in the x direction (meters).

Figure 13A:
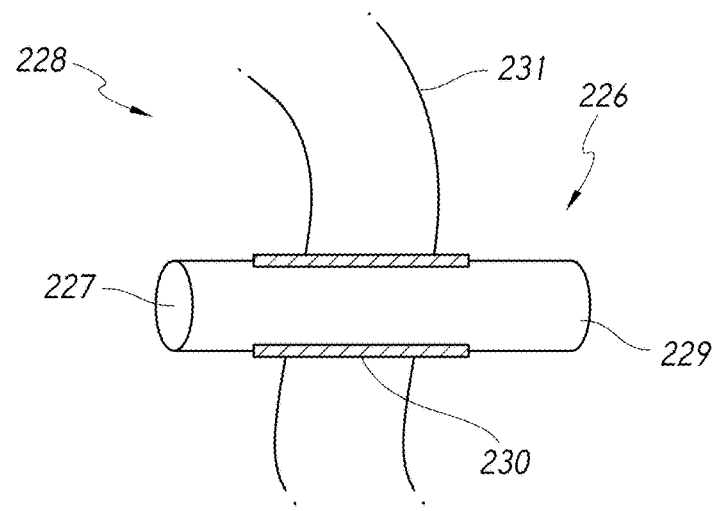
FIGS. 13A-13C provide schematics of a shunt implanted into an eye for regulation of fluid flow from the anterior chamber of the eye to a drainage structure of the eye.

FIG. 13A provides a schematic of a shunt 226 implanted into an eye for regulation of fluid flow from the anterior chamber of the eye to an area of lower pressure (e.g., the intra-Tenon's space, the subconjunctival space, the episcleral vein, the suprachoroidal space, or Schlemm's canal). In certain embodiments, the area of lower pressure is the subarachnoid space. The shunt is implanted such that a proximal end 227 of the shunt 226 resides in the anterior chamber 228 of the eye, and a distal end 229 of the shunt 226 resides outside of the anterior chamber to conduct aqueous humor from the anterior chamber to an area of lower pressure. A flexible portion 230 of the shunt 226 spans at least a portion of the sclera of the eye. As shown in FIG. 13A, the flexible portion spans an entire length of the sclera 221.

Figure 13B:
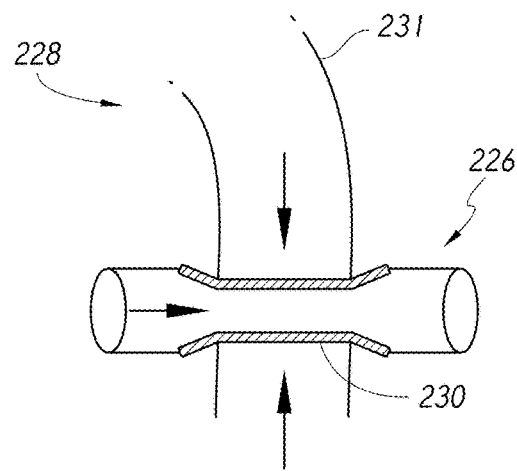

When the pressure exerted on the flexible portion 230 of the shunt 226 by sclera 231 (vertical arrows) is greater than the pressure exerted on the flexible portion 230 of the shunt 226 by the fluid flowing through the shunt (horizontal arrow), the flexible portion 230 decreases in diameter, restricting flow through the shunt 226 (FIG. 13B). The restricted flow results in aqueous humor leaving the anterior chamber 228 at a reduced rate.

Figure 13C:
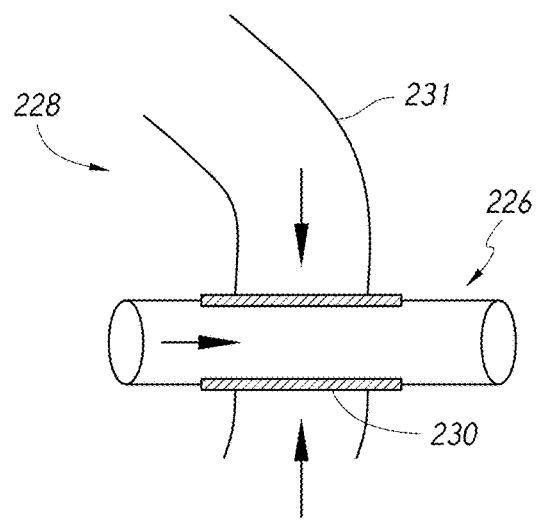

When the pressure exerted on the flexible portion 230 of the shunt 226 by the fluid flowing through the shunt (horizontal arrow) is greater than the pressure exerted on the flexible portion 230 of the shunt 226 by the sclera 231 (vertical arrows), the flexible portion 230 increases in diameter, increasing flow through the shunt 226 (FIG. 13C). The increased flow results in aqueous humor leaving the anterior chamber 228 at an increased rate.

Some embodiments encompasses shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 μm to approximately 250 μm, an outside diameter from diameter from approximately 100 μm to approximately 450 μm, such as approximately 190 μm to approximately 300 μm, and a length from approximately 0.5 mm to approximately 20 mm, such as from approximately 2 mm to approximately 10 mm.

In a particular embodiments, the shunt has a length of about 6 mm and an inner diameter of about 64 μm. With these dimensions, the pressure difference between the proximal end of the shunt that resides in the anterior chamber and the distal end of the shunt that resides outside the anterior chamber is about 4.3 mmHg. Such dimensions thus allow the implant to act as a controlled valve and protect the integrity of the anterior chamber.

It will be appreciated that different dimensioned implants may be used. For example, shunts that range in length from about 0.5 mm to about 20 mm, such as from about 2 mm to about 10 mm, and have a range in inner diameter from about 10 μm to about 100 μm allow for pressure control from approximately 0.5 mmHg to approximately 20 mmHg.

The material of the flexible portion and the thickness of the wall of the flexible portion will determine how reactive the flexible portion is to the pressures exerted upon it by the surrounding tissue and the fluid flowing through the shunt. Generally, with a certain material, the thicker the flexible portion, the less responsive the portion will be to pressure. In certain embodiments, the flexible portion is a gelatin or other similar material, and the thickness of the gelatin material forming the wall of the flexible portion ranges from about 10 μm thick to about 100 μm thick.

In a certain embodiment, the gelatin used for making the flexible portion is known as gelatin Type B from bovine skin. An exemplary gelatin is PB Leiner gelatin from bovine skin, Type B, 225 Bloom, USP. Another material that may be used in the making of the flexible portion is a gelatin Type A from porcine skin, also available from Sigma Chemical. Such gelatin is available from Sigma Chemical Company of St. Louis, Mo. under Code G-9382. Still other suitable gelatins include bovine bone gelatin, porcine bone gelatin and human-derived gelatins. In addition to gelatins, the flexible portion may be made of hydroxypropyl methylcellulose (HPMC), collagen, polylactic acid, polylglycolic acid, hyaluronic acid and glycosaminoglycans.

In certain embodiments, the gelatin is cross-linked. Cross-linking increases the inter- and intramolecular binding of the gelatin substrate. Any method for cross-linking the gelatin may be used. In a particular embodiment, the formed gelatin is treated with a solution of a cross-linking agent such as, but not limited to, glutaraldehyde. Other suitable compounds for cross-linking include 1-ethyl-3(3-dimethylaminopropyl)carbodiimide (EDC). Cross-linking by radiation, such as gamma or electron beam (e-beam) may be alternatively employed.

In one embodiment, the gelatin is contacted with a solution of approximately 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should be in the range of 7 to 7.8 and, more particularly, 7.35-7.44 and typically approximately 7.4+/−0.01. If necessary, the pH may be adjusted by adding a suitable amount of a base such as sodium hydroxide as needed.

Methods for forming the flexible portion of the shunt are shown for example in Yu et al. (U.S. Pat. Pub. No. 2008/0108933), the content of which is incorporated by reference herein in its entirety. In an exemplary protocol, the flexible portion may be made by dipping a core or substrate such as a wire of a suitable diameter in a solution of gelatin. The gelatin solution is typically prepared by dissolving a gelatin powder in de-ionized water or sterile water for injection and placing the dissolved gelatin in a water bath at a temperature of approximately 55° C. with thorough mixing to ensure complete dissolution of the gelatin. In one embodiment, the ratio of solid gelatin to water is approximately 10% to 50% gelatin by weight to 50% to 90% by weight of water. In an embodiment, the gelatin solution includes approximately 40% by weight, gelatin dissolved in water. The resulting gelatin solution should be devoid of air bubbles and has a viscosity that is between approximately 200-500 cp and more particularly between approximately 260 and 410 cp (centipoise).

Once the gelatin solution has been prepared, in accordance with the method described above, supporting structures such as wires having a selected diameter are dipped into the solution to form the flexible portion. Stainless steel wires coated with a biocompatible, lubricious material such as polytetrafluoroethylene (Teflon) are preferred.

Typically, the wires are gently lowered into a container of the gelatin solution and then slowly withdrawn. The rate of movement is selected to control the thickness of the coat. In addition, it is preferred that the tube be removed at a constant rate in order to provide the desired coating. To ensure that the gelatin is spread evenly over the surface of the wire, in one embodiment, the wires may be rotated in a stream of cool air which helps to set the gelatin solution and affix film onto the wire. Dipping and withdrawing the wire supports may be repeated several times to further ensure even coating of the gelatin. Once the wires have been sufficiently coated with gelatin, the resulting gelatin films on the wire may be dried at room temperature for at least 1 hour, and more preferably, approximately 10 to 24 hours. Apparatus for forming gelatin tubes are described in Yu et al. (U.S. Pat. Pub. No. 2008/0108933).

Once dried, the formed flexible portions may be treated with a cross-linking agent. In one embodiment, the formed flexible portion may be cross-linked by dipping the wire (with film thereon) into the 25% glutaraldehyde solution, at pH of approximately 7.0-7.8 and more preferably approximately 7.35-7.44 at room temperature for at least 4 hours and preferably between approximately 10 to 36 hours, depending on the degree of cross-linking desired. In one embodiment, the formed flexible portion is contacted with a cross-linking agent such as gluteraldehyde for at least approximately 16 hours. Cross-linking can also be accelerated when it is performed a high temperatures. It is believed that the degree of cross-linking is proportional to the bio-absorption time of the shunt once implanted. In general, the more cross-linking, the longer the survival of the shunt in the body.

The residual glutaraldehyde or other cross-linking agent is removed from the formed flexible portion by soaking the tubes in a volume of sterile water for injection. The water may optionally be replaced at regular intervals, circulated or re-circulated to accelerate diffusion of the unbound glutaraldehyde from the tube. The tubes are washed for a period of a few hours to a period of a few months with the ideal time being 3-14 days. The now cross-linked gelatin tubes may then be dried (cured) at ambient temperature for a selected period of time. It has been observed that a drying period of approximately 48-96 hours and more typically 3 days (i.e., 72 hours) may be preferred for the formation of the cross-linked gelatin tubes.

Where a cross-linking agent is used, it may be desirable to include a quenching agent in the method of making the flexible portion. Quenching agents remove unbound molecules of the cross-linking agent from the formed flexible portion. In certain cases, removing the cross-linking agent may reduce the potential toxicity to a patient if too much of the cross-linking agent is released from the flexible portion. In certain embodiments, the formed flexible portion is contacted with the quenching agent after the cross-linking treatment and, may be included with the washing/rinsing solution. Examples of quenching agents include glycine or sodium borohydride.

The formed flexible portion may be further coated or impregnated with biologics and/or pharmaceuticals, as discussed herein.

After the requisite drying period, the formed and cross-linked flexible portion is removed from the underlying supports or wires. In one embodiment, wire tubes may be cut at two ends and the formed gelatin flexible portion slowly removed from the wire support. In another embodiment, wires with gelatin film thereon, may be pushed off using a plunger or tube to remove the formed gelatin flexible portion.

Multi-Port Shunts

Other aspects of some embodiments generally provide multi-port shunts. Such shunts reduce probability of the shunt clogging after implantation because fluid can enter or exit the shunt even if one or more ports of the shunt become clogged with particulate. In certain embodiments, the shunt includes a hollow body defining a flow path and more than two ports, in which the body is configured such that a proximal portion receives fluid from the anterior chamber of an eye and a distal portion directs the fluid to a location of lower pressure with respect to the anterior chamber. Exemplary areas of lower pressure include intra-Tenon's space, the subconjunctival space, the episcleral vein, the suprachoroidal space, Schlemm's canal, or drainage structures associated with the intra-scleral space. Another exemplary area of lower pressure to which fluid may be drained is the subarachnoid space.

Figure 14A:
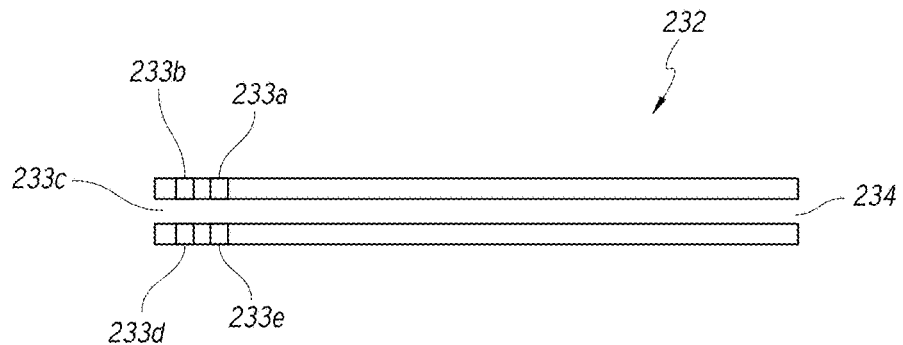
FIGS. 14A-14C show different embodiments of multi-port shunts.
Figure 14B:
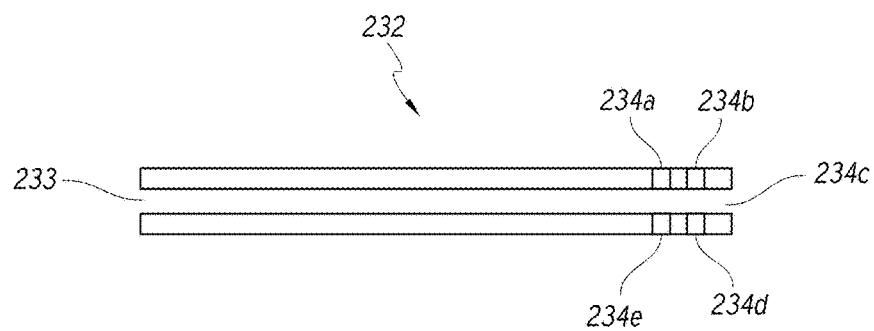
Figure 14C:
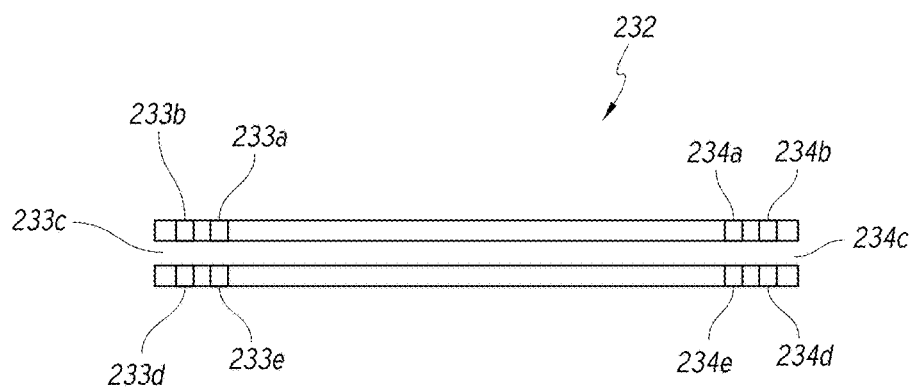

The shunt may have many different configurations. FIG. 14A shows an embodiment of a shunt 232 in which the proximal portion of the shunt (i.e., the portion disposed within the anterior chamber of the eye) includes more than one port (designated as numbers 233a to 233e) and the distal portion of the shunt (i.e., the portion that is located in the intra-Tenon's space) includes a single port 234. FIG. 14B shows another embodiment of a shunt 232 in which the proximal portion includes a single port 233 and the distal portion includes more than one port (designated as numbers 234a to 234e). FIG. 14C shows another embodiment of a shunt 232 in which the proximal portions include more than one port (designated as numbers 233a to 233e) and the distal portions include more than one port (designated as numbers 234a to 234e). While FIGS. 14A-14C show shunts that have five ports at the proximal portion, distal portion, or both, those shunts are only exemplary embodiments. The ports may be located along any portion of the shunt, and some embodiments of the shunt include all shunts having more than two ports. For example, some embodiments of the shunt may include at least three ports, at least four ports, at least five ports, at least 10 ports, at least 15 ports, or at least 20 ports.

The ports may be positioned in various different orientations and along various different portions of the shunt. In certain embodiments, at least one of the ports is oriented at an angle to the length of the body. In certain embodiments, at least one of the ports is oriented 90° to the length of the body. See for example FIG. 14A, which depicts ports 233a, 233b, 233d, and 233e as being oriented at a 90° angle to port 233c.

Figure 15A:
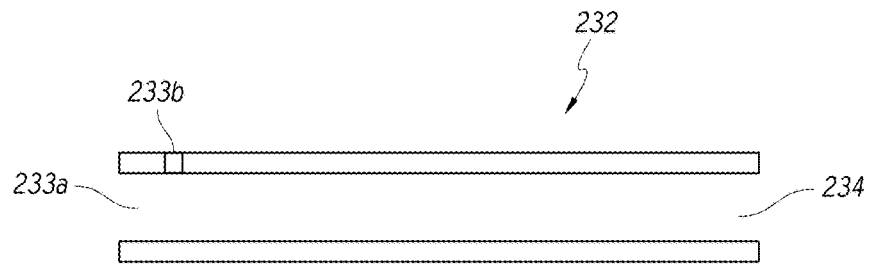
FIGS. 15A-15B show different embodiments of multi-port shunts having different diameter ports.
Figure 15B:
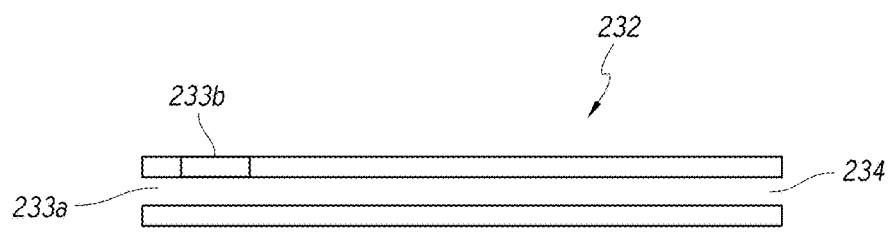

The ports may have the same or different inner diameters. In certain embodiments, at least one of the ports has an inner diameter that is different from the inner diameters of the other ports. FIGS. 15A-15B show embodiments of a shunt 232 having multiple ports (233a and 233b) at a proximal end and a single port 234 at a distal end. FIG. 15A shows that port 233b has an inner diameter that is different from the inner diameters of ports 233a and 234. In this figure, the inner diameter of port 233b is less than the inner diameter of ports 233a and 234. An exemplary inner diameter of port 233b is from about 20 µm to about 40 µm, particularly about 30 µm. In other embodiments, the inner diameter of port 33b is greater than the inner diameter of ports 233a and 234. See for example FIG. 15B.

Some embodiments encompasses shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 190 µm to approximately 300 µm, and a length from approximately 0.5 mm to approximately 20 mm. Some embodiments of the shunt may be made from any biocompatible material. An exemplary material is gelatin. Methods of making shunts composed of gelatin are described above.

Shunts with Overflow Ports

Other aspects of some embodiments generally provide shunts with overflow ports. Those shunts are configured such that the overflow port remains partially or completely closed until there is a pressure build-up within the shunt sufficient to force open the overflow port. Such pressure build-up typically results from particulate partially or fully clogging an entry or an exit port of the shunt. Such shunts reduce probability of the shunt clogging after implantation because fluid can enter or exit the shunt by the overflow port even if one port of the shunt becomes clogged with particulate.

Figure 16A:
FIGS. 16A, 16B and 16C provide schematics of shunts having a slit located along a portion of the length of the shunt.
Figure 16B:
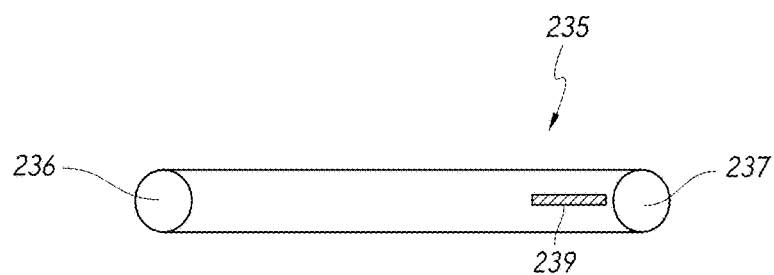
Figure 16C:
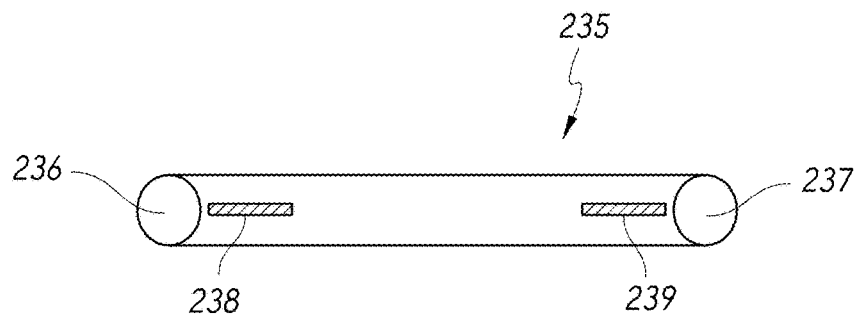

In certain embodiments, the shunt includes a hollow body defining an inlet configured to receive fluid from an anterior chamber of an eye and an outlet configured to direct the fluid to the intra-Tenon's or intrascleral space, or other areas of lower pressure disclosed herein, the body further including at least one slit. The slit may be located at any place along the body of the shunt. FIG. 16A shows a shunt 235 having an inlet 236, an outlet 237, and a slit 238 located in proximity to the inlet 236. FIG. 16B shows a shunt 235 having an inlet 236, an outlet 237, and a slit 239 located in proximity to the outlet 237. FIG. 16C shows a shunt 235 having an inlet 236, an outlet 237, a slit 238 located in proximity to the inlet 236, and a slit 239 located in proximity to the outlet 237.

Figure 17:
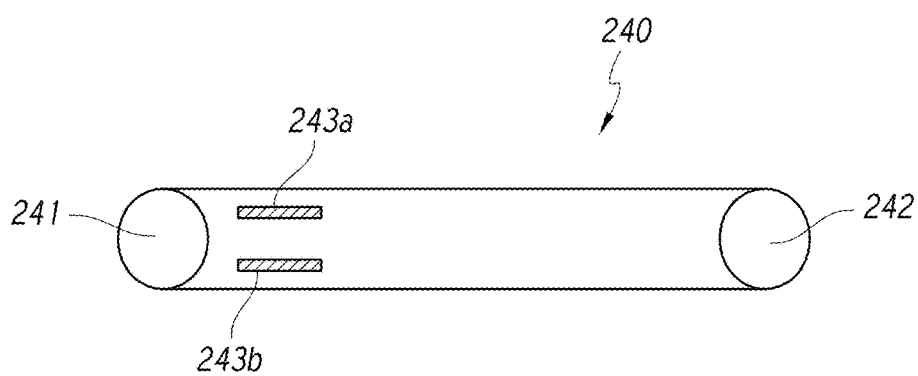
FIG. 17 depicts a shunt having multiple slits along a length of the shunt.

While FIGS. 16A-16B show shunts have only a single overflow port at the proximal portion, the distal portion, or both the proximal and distal portions, those shunts are only exemplary embodiments. The overflow port(s) may be located along any portion of the shunt, and some embodiments of the shunt include shunts having more than one overflow port. In certain embodiments, some embodiments of the shunt include more than one overflow port at the proximal portion, the distal portion, or both. For example, FIG. 17 shows a shunt 240 having an inlet 241, an outlet 242, and slits 243a and 243b located in proximity to the inlet 241. Some embodiments of the shunt may include at least two overflow ports, at least three overflow ports, at least four overflow ports, at least five overflow ports, at least 10 overflow ports, at least 15 overflow ports, or at least 20 overflow ports. In certain embodiments, some embodiments of the shunt include two slits that overlap and are oriented at 90° to each other, thereby forming a cross.

Figure 18:
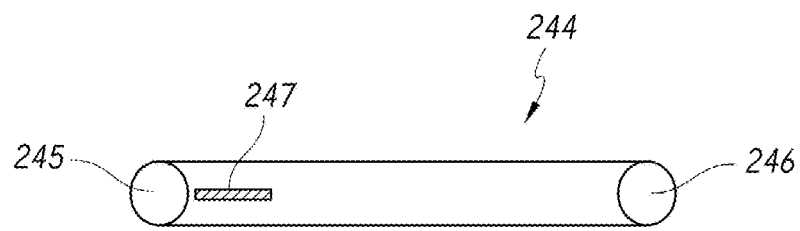
FIG. 18 depicts a shunt having a slit at a proximal end of the shunt.

In certain embodiments, the slit may be at the proximal or the distal end of the shunt, producing a split in the proximal or the distal end of the implant. FIG. 18 shows an embodiment of a shunt 244 having an inlet 245, outlet 246, and a slit 247 that is located at the proximal end of the shunt, producing a split in the inlet 245 of the shunt.

In certain embodiments, the slit has a width that is substantially the same or less than an inner diameter of the inlet. In other embodiments, the slit has a width that is substantially the same or less than an inner diameter of the outlet. In certain embodiments, the slit has a length that ranges from about 0.05 mm to about 2 mm, and a width that ranges from about 10 µm to about 200 µm. Generally, the slit does not direct the fluid unless the outlet is obstructed. However, the shunt may be configured such that the slit does direct at least some of the fluid even if the inlet or outlet is not obstructed.

Some embodiments encompasses shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from diameter from approximately 100 µm to approximately 450 µm, such as approximately 190 µm to approximately 300 µm, and a length from approximately 0.5 mm to approximately 20 mm, such as from approximately 2 mm to approximately 10 mm. Some embodiments of the shunt may be made from any biocompatible material. An exemplary material is gelatin. Methods of making shunts composed of gelatin are described above.

Shunts Having a Variable Inner Diameter

In other aspects, some embodiments generally provide a shunt having a variable inner diameter. In particular embodiments, the diameter increases from inlet to outlet of the shunt. By having a variable inner diameter that increases from inlet to outlet, a pressure gradient is produced and particulate that may otherwise clog the inlet of the shunt is forced through the inlet due to the pressure gradient. Further, the particulate will flow out of the shunt because the diameter only increases after the inlet.

Figure 19A:
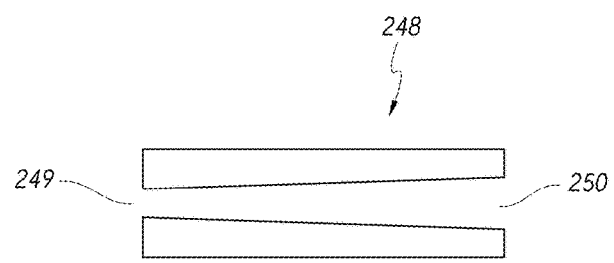
FIGS. 19A-19B show schematics of shunt that have a variable inner diameter.
Figure 19B:
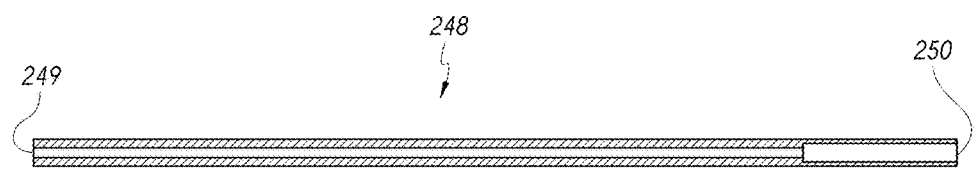

FIGS. 19A-19B show embodiments of a shunt 248 having an inlet 249 configured to receive fluid from an anterior chamber of an eye and an outlet 250 configured to direct the fluid to a location of lower pressure with respect to the anterior chamber, in which the body further includes a variable inner diameter that increases along the length of the body from the inlet 249 to the outlet 250. In certain embodiments, the inner diameter continuously increases along the length of the body, for example as shown in FIG. 19A. In other embodiments, the inner diameter remains constant along portions of the length of the body, as shown in FIG. 19B.

In exemplary embodiments, the inner diameter may range in size from about 10 µm to about 200 µm, and the inner diameter at the outlet may range in size from about 15 µm to about 300 µm. Some embodiments encompasses shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from diameter from approximately 100 µm to approximately 450 µm, such as approximately 190 µm to approximately 300 µm, and a length from approximately 0.5 mm to approximately 20 mm, such as from approximately 2 mm to approximately 10 mm. Some embodiments of the shunt may be made from any biocompatible material. An exemplary material is gelatin. Methods of making shunts composed of gelatin are described above.

Shunts Having Pronged Ends

In other aspects, some embodiments generally provide shunts for facilitating conduction of fluid flow away from an organ, the shunt including a body, in which at least one end of the shunt is shaped to have a plurality of prongs. Such shunts reduce probability of the shunt clogging after implantation because fluid can enter or exit the shunt by any space between the prongs even if one portion of the shunt becomes clogged with particulate.

FIGS. 20A-20D show embodiments of a shunt 252 in which at least one end of the shunt 252 includes a plurality of prongs 253a-d. FIGS. 20A-20D show embodiments in which both a proximal end and a distal end of the shunt are shaped to have the plurality of prongs. However, numerous different configurations are envisioned. For example, in certain embodiments, only the proximal end of the shunt is shaped to have the plurality of prongs. In other embodiments, only the distal end of the shunt is shaped to have the plurality of prongs.

Figure 20A:
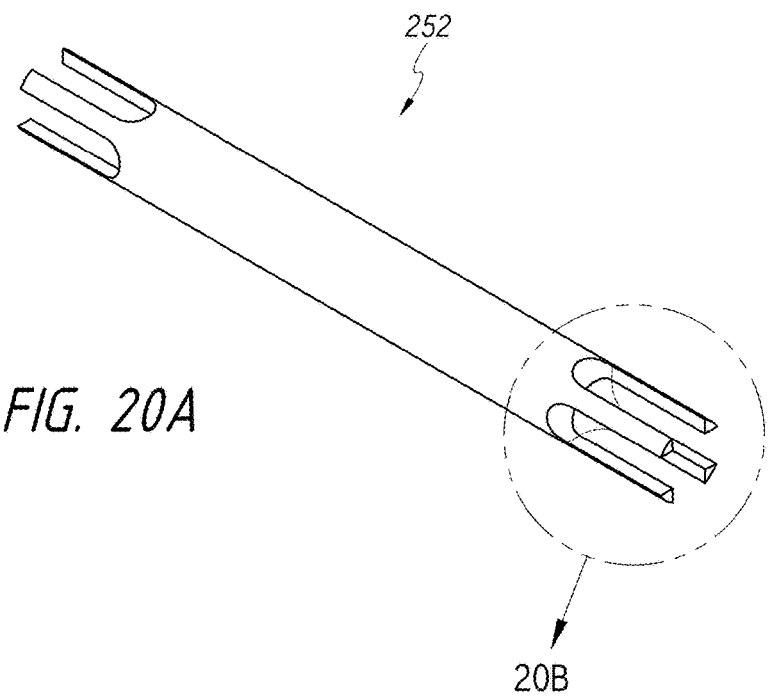
FIGS. 20A-20D depict a shunt having multiple prongs at a distal and/or proximal end.
Figure 20B:
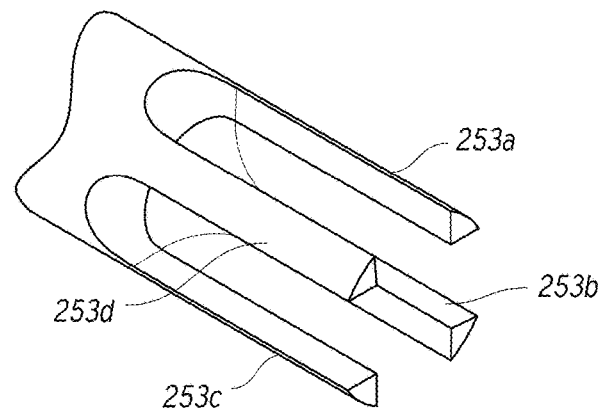
Figure 20C:
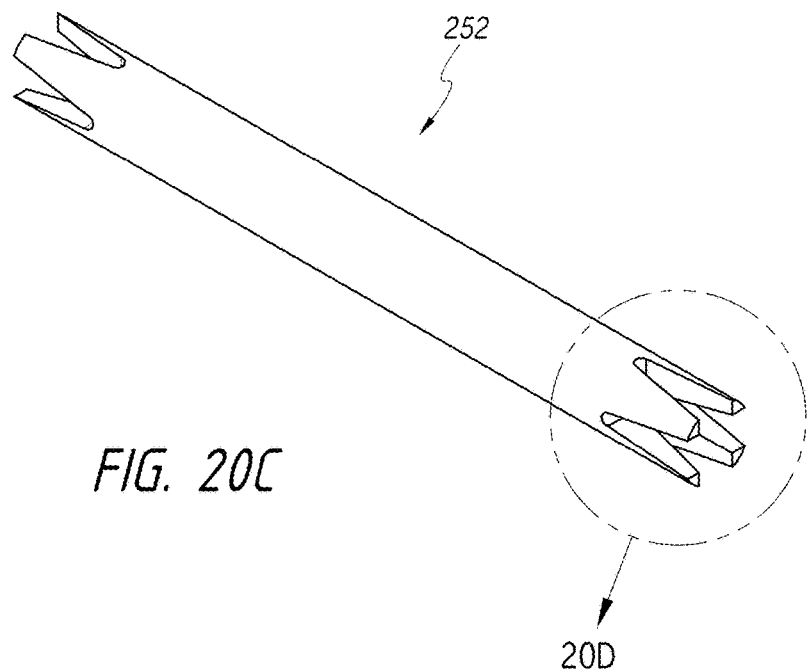
Figure 20D:
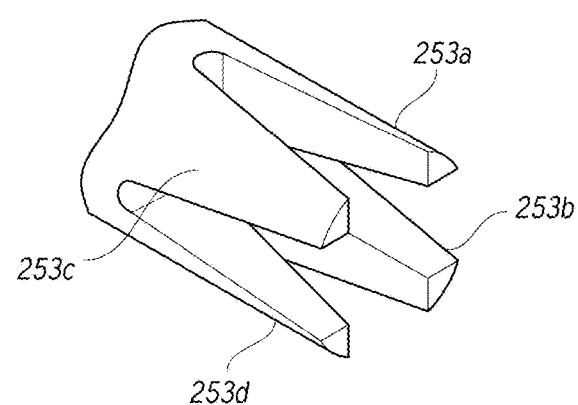

Prongs 253a-d can have any shape (i.e., width, length, height). FIGS. 20A-20B show prongs 253a-d as straight prongs. In this embodiment, the spacing between the prongs 253a-d is the same. In another embodiment shown in FIGS. 20C-20D, prongs 253a-d are tapered. In this embodiment, the spacing between the prongs increases toward a proximal and/or distal end of the shunt 252.

FIGS. 20A-20D show embodiments that include four prongs. However, some embodiments of the shunt may accommodate any number of prongs, such as two prongs, three prongs, four prongs, five prongs, six prongs, seven prongs, eight prongs, nine prongs, ten prongs, etc. The number of prongs chosen will depend on the desired flow characteristics of the shunt.

Some embodiments encompass shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Some embodiments of the shunt may be made from any biocompatible material. An exemplary material is gelatin. Methods of making shunts composed of gelatin are described above.

Shunts Having a Longitudinal Slit

In other aspects, some embodiments generally provide a shunt for draining fluid from an anterior chamber of an eye that includes a hollow body defining an inlet configured to receive fluid from an anterior chamber of the eye and an outlet configured to direct the fluid to a location of lower pressure with respect to the anterior chamber; the shunt being configured such that at least one end of the shunt includes a longitudinal slit. Such shunts reduce probability of the shunt clogging after implantation because the end(s) of the shunt can more easily pass particulate which would generally clog a shunt lacking the slits.

FIGS. 21A-21D show embodiments of a shunt 254 in which at least one end of the shunt 254 includes a longitudinal slit 255 that produces a top portion 256a and a bottom portion 256b in a proximal and/or distal end of the shunt 254. FIGS. 21A-21D show an embodiment in which both a proximal end and a distal end include a longitudinal slit 255 that produces a top portion 256a and a bottom portion 256b in both ends of the shunt 254. However, numerous different configurations are envisioned. For example, in certain embodiments, only the proximal end of the shunt includes longitudinal slit 255. In other embodiments, only the distal end of the shunt includes longitudinal slit 255.

Figure 21A:
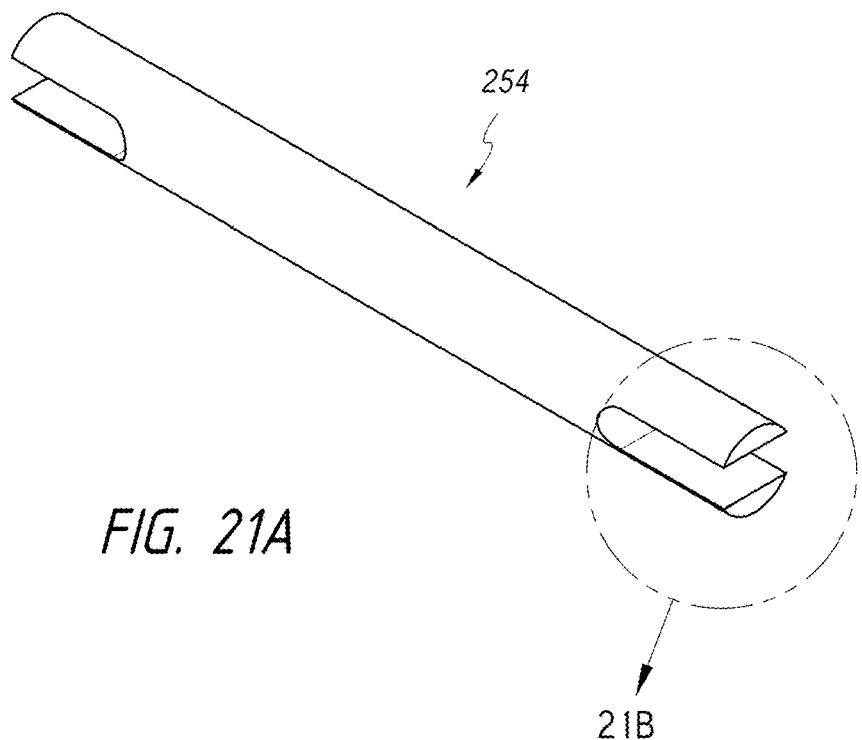
FIGS. 21A-21D depict a shunt having a longitudinal slit at a distal and/or proximal end.
Figure 21B:
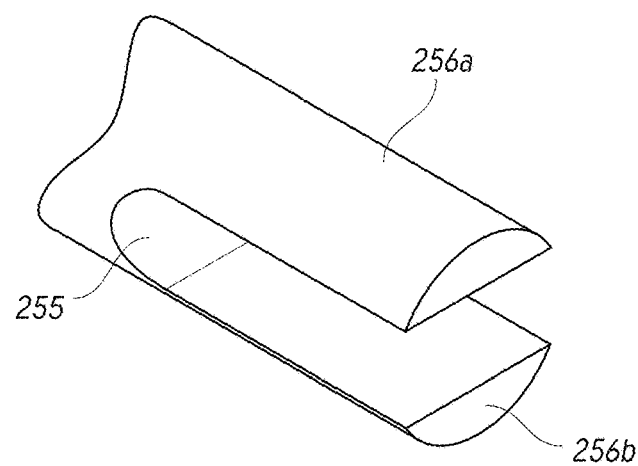
Figure 21C:
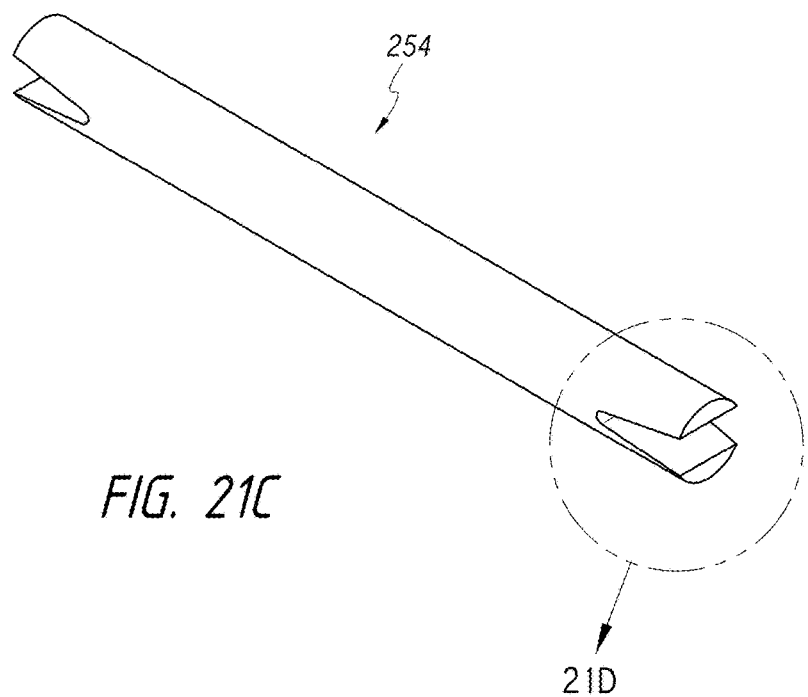
Figure 21D:
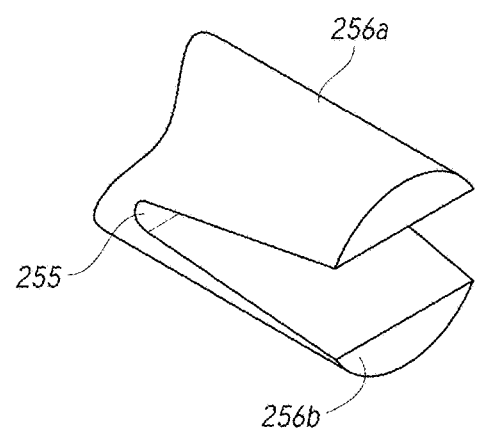

Longitudinal slit 255 can have any shape (i.e., width, length, height). FIGS. 21A-21B show a longitudinal slit 255 that is straight such that the space between the top portion 256a and the bottom portion 256b remains the same along the length of the slit 255. In another embodiment shown in FIGS. 21C-21D, longitudinal slit 255 is tapered. In this embodiment, the space between the top portion 245a and the bottom portion 256b increases toward a proximal and/or distal end of the shunt 254.

Some embodiments encompass shunts of different shapes and different dimensions, and some embodiments of the shunt may be any shape or any dimension that may be accommodated by the eye. In certain embodiments, the intraocular shunt is of a cylindrical shape and has an outside cylindrical wall and a hollow interior. The shunt may have an inside diameter from approximately 10 µm to approximately 250 µm, an outside diameter from approximately 100 µm to approximately 450 µm, and a length from approximately 2 mm to approximately 10 mm. Some embodiments of the shunt may be made from any biocompatible material. An exemplary material is gelatin. Methods of making shunts composed of gelatin are described above.

Pharmaceutical Agents

In certain embodiments, some embodiments of the shunt may be coated or impregnated with at least one pharmaceutical and/or biological agent or a combination thereof. The pharmaceutical and/or biological agent may coat or impregnate an entire exterior of the shunt, an entire interior of the shunt, or both. Alternatively, the pharmaceutical or biological agent may coat and/or impregnate a portion of an exterior of the shunt, a portion of an interior of the shunt, or both. Methods of coating and/or impregnating an intraocular shunt with a pharmaceutical and/or biological agent are known in the art. See for example, Darouiche (U.S. Pat. Nos. 7,790, 183; 6,719,991; 6,558,686; 6,162,487; 5,902,283; 5,853, 745; and 5,624,704) and Yu et al. (U.S. Pat. Pub. No. 2008/0108933). The content of each of these references is incorporated by reference herein its entirety.

In certain embodiments, the exterior portion of the shunt that resides in the anterior chamber after implantation (e.g., about 1 mm of the proximal end of the shunt) is coated and/or impregnated with the pharmaceutical or biological agent. In other embodiments, the exterior of the shunt that resides in the scleral tissue after implantation of the shunt is coated and/or impregnated with the pharmaceutical or biological agent. In other embodiments, the exterior portion of the shunt that resides in the area of lower pressure, such as the intrascleral space, the intra-Tenon's space, or the subconjunctival space, after implantation is coated and/or impregnated with the pharmaceutical or biological agent. In embodiments in which the pharmaceutical or biological agent coats and/or impregnates the interior of the shunt, the agent may be flushed through the shunt and into the area of lower pressure (e.g., the intra-Tenon's space or the subconjunctival space).

Any pharmaceutical and/or biological agent or combination thereof may be used with some embodiments of the shunt. The pharmaceutical and/or biological agent may be released over a short period of time (e.g., seconds) or may be released over longer periods of time (e.g., days, weeks, months, or even years). Exemplary agents include antimitotic pharmaceuticals such as Mitomycin-C or 5-Fluorouracil, anti-VEGF (such as Lucintes, Macugen, Avastin, VEGF or steroids).

Figure 22A:
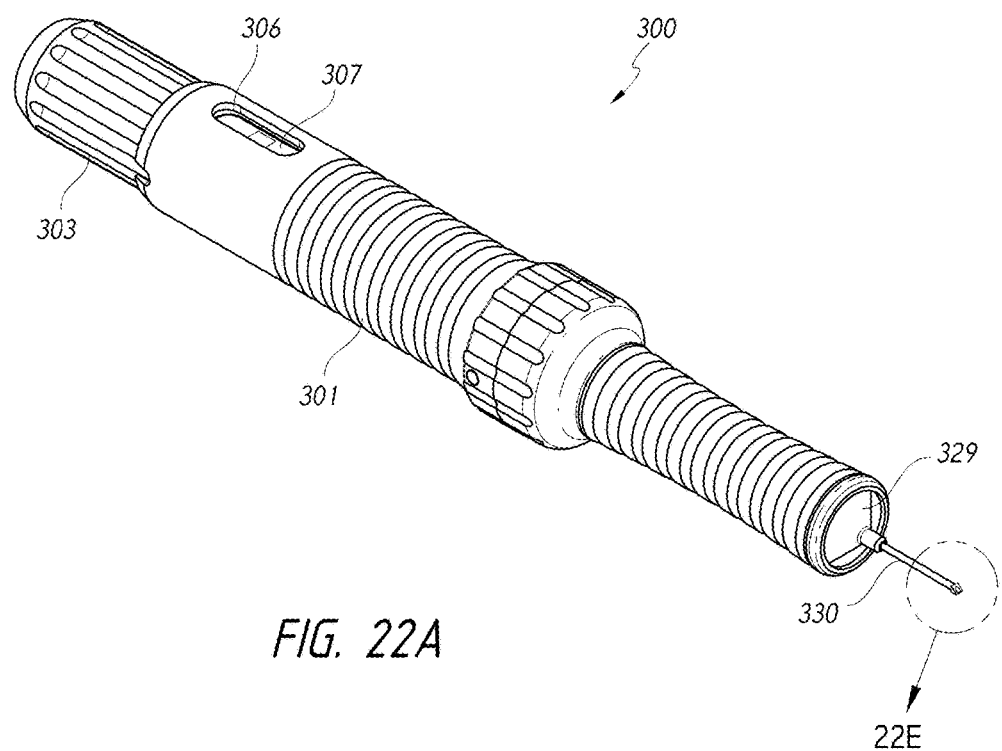
FIG. 22A is a schematic showing an embodiment of a shunt deployment device according to some embodiments.

Reference is now made to FIG. 22A which shows an embodiment of a shunt deployment device 300 according to some embodiments. In some embodiments, the device 300 may be used to re-open a partially or completely closed anterior chamber angle and deploy an intraocular shunt. While FIG. 22A shows a handheld manually operated shunt deployment device, it will be appreciated that some embodiments of the device may be coupled with robotic systems and may be completely or partially automated. As shown in FIG. 22A deployment device 300 includes a generally cylindrical body or housing 301, however, the body shape of housing 301 could be other than cylindrical. Housing 301 may have an ergonomical shape, allowing for comfortable grasping by an operator. Housing 301 is shown with optional grooves 302 to allow for easier gripping by a surgeon.

Figure 22E:
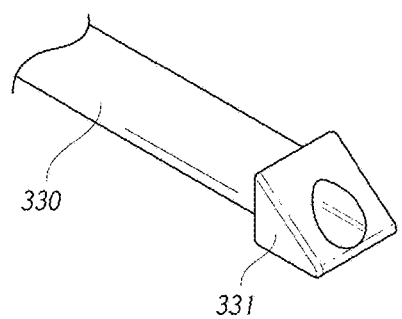
FIG. 22E is a schematic showing an enlarged view of a protrusion on a distal end of a distal portion of a housing of the device of FIG. 22A. In this figure, a bottom portion of the protrusion is flat and a top portion of the protrusion is angled.
Figure 22B:
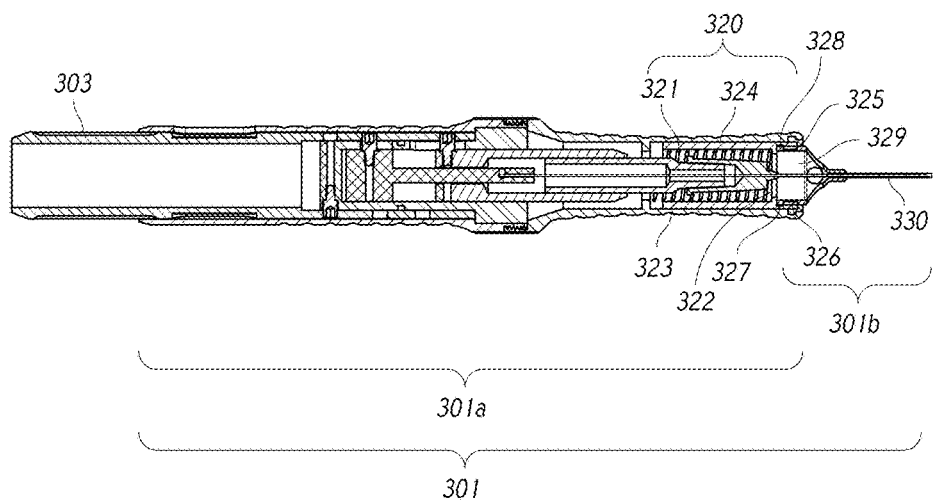
FIG. 22B shows a cross sectional view of the device of FIG. 22A. In this figure, the distal portion of the housing is extended from the proximal portion of the housing.

FIG. 22B shows a cross sectional view of device 300. This figure shows that housing 301 includes a proximal portion 301a and a distal portion 301b. The distal portion 301b is movable within proximal portion 301a. In this figure, spring mechanism 320 includes a spring 321 that controls movement of distal portion 301b. Spring mechanism 320 further includes a member 322 that acts as a stopper and limits axial retraction of distal portion 301b within proximal portion 301a. Spring mechanism 320 further includes members 323 and 324 that run the length of spring 321. The ends of members 323 and 324 include flanges 325 and 326 that project inward from members 323 and 324. An end of distal portion 301b includes flanges 327 and 328 that project outward from distal portion 301b. Flanges 325 and 326 interact with flanges 327 and 328 to prevent release of distal portion 301b from proximal portion 301a. The flanges 325 and 326 and 327 and 328 hold the distal portion 301b in an extended position until a compressive force acts upon distal portion 301b, thereby causing distal portion 301b to partially retract within proximal portion 301a.

Figure 22C:
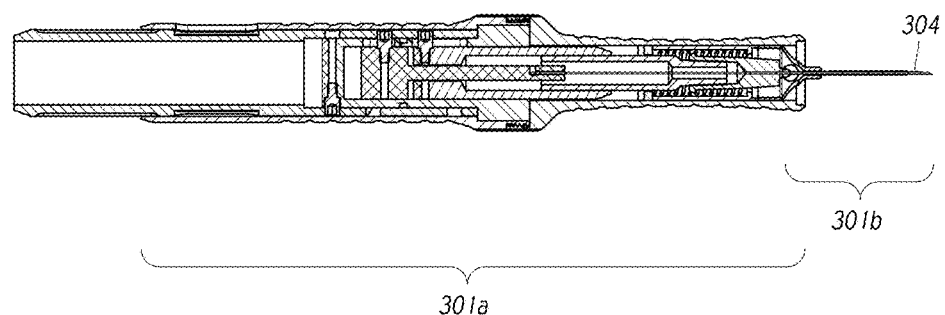
FIG. 22C shows a cross sectional view of the device of FIG. 22A. In this figure, the distal portion of the housing is retracted within the proximal portion of the housing.

Distal portion 301b includes a capsule 329 and a hollow sleeve 330. Capsule 329 and sleeve 330 may be formed integrally or may be separate components that are coupled or connected to each other. The hollow sleeve 330 is configured for insertion into an eye and to extend into an anterior chamber of an eye. FIG. 22B shows distal portion 301b of housing 301 extended from proximal portion 301a of housing 301. In this configuration, hollow shaft 304 (not shown in this figure) is completely disposed within sleeve 330. FIG. 22C shows distal portion 301b of housing 301 retracted within proximal portion 301a of housing 301. Retraction of distal portion 301b of housing 301 within proximal portion 301a of housing 301 exposes hollow shaft 304, which is discussed in greater detail below.

Figure 22D:
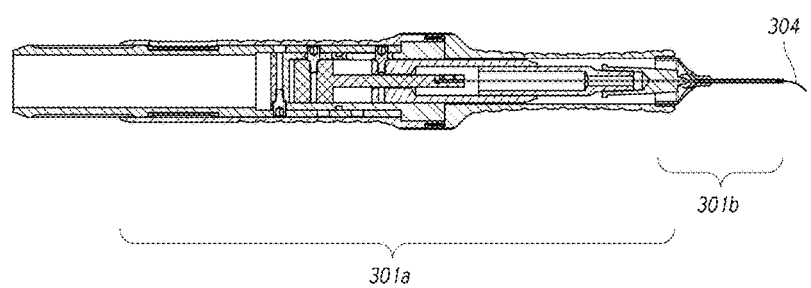
FIG. 22D shows another cross sectional view of an embodiment of the device of FIG. 22A.

The hollow shaft 304 may include a sharpened distal end. With reference to FIG. 22D, the hollow shaft 304 may be flexible and pre-bent to follow the scleral spur down along the sclera upon extension of the hollow shaft 304 from the sleeve 330, which is discussed in greater detail below. The material used for the hollow shaft 304 may be any memory shape material, such as spring steel, such that the hollow shaft 304 can easily transform from its bent position to a straight cannula when housed within the sleeve 330.

A distal end of sleeve 330 may optionally include a protrusion 331 (FIG. 22D). Protrusion 331 provides resistance feedback to an operator as the operator is advancing the sleeve 330 through an anterior chamber of an eye. Further, protrusion 331 can be of a shape and size that it is capable of re-opening a partially or completely closed anterior chamber angle of an eye as an operator is advancing the device 300 through an anterior chamber of an eye. In a standard ab interno approach (see, for example, Yu et al. U.S. Pat. No. 6,544,249 and U.S. Pat. Pub. No. 2008/0108933) a deployment device holding a shunt enters an eye through a cornea. The deployment device is advanced across the anterior chamber in what is referred to as a transpupil implant insertion. The deployment device is advanced to the sclera on the opposite side of the eye from which the device entered the eye. With some embodiments of the device, upon advancement of the device 300 across an anterior chamber of the eye, the protrusion 331 at the distal end of the hollow sleeve 330 will contact the sclera, providing resistance feedback to an operator that no further advancement of the device 300 is necessary (see FIGS. 38A-38E). This feedback also informs the operator that the device 300 is in proper position for exposure of the hollow shaft 304, which will advance through the sclera for deployment of an intraocular shunt. The protrusion 331, provides adequate surface area at the distal end of sleeve 330, thus preventing sleeve 330 from entering the sclera.

Further, in some embodiments, the deployment device can be advanced into the anterior chamber angle on the opposite side of the eye from which the device entered the eye. With some embodiments of the device, upon advancement of the device 300 across an anterior chamber of the eye, the protrusion 331 at the distal end of the hollow sleeve 330 will contact a partially or completely closed anterior chamber angle, and continued advancement of the device 300 will result in the protrusion 331 re-opening the partially or completely closed anterior chamber angle. Once re-opened by the protrusion 131, the device 300 can be moved into proper position for exposure of the hollow shaft 304, which will advance through the sclera for deployment of an intraocular shunt. The protrusion 331, provides adequate surface area at the distal end of sleeve 330, thus preventing sleeve 330 from entering the tissue of the eye that is blocking access the trabecular meshwork (e.g., the iris).

Figure 23A:
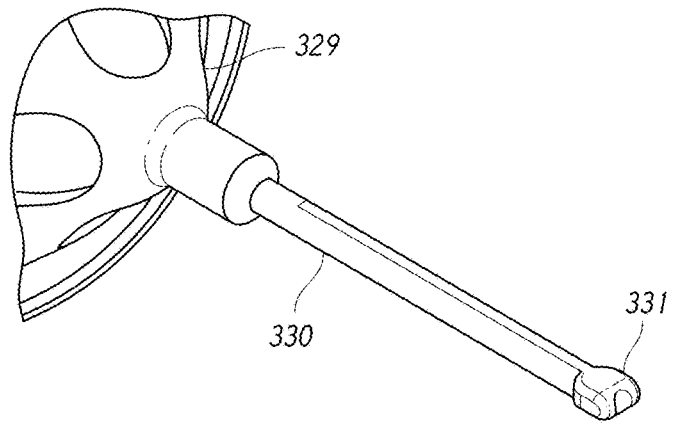
FIGS. 23A-23C are schematics showing an enlarged view of a protrusion on a distal end of a distal portion of a housing of some embodiments of the device.
Figure 23B:
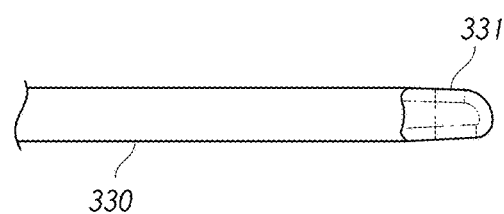
Figure 23C:
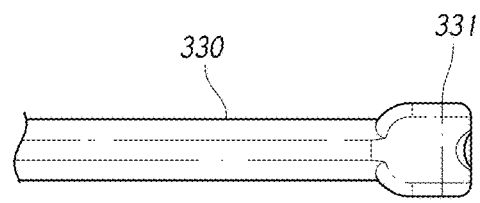

In certain embodiments, protrusion 331 has a substantially flat bottom portion and an angled top portion (FIG. 22E). In other embodiments, protrusion 331 has a slightly tapered top and a slightly tapered bottom with a rounded distal portion (FIGS. 23A-23C).

Figure 24A:
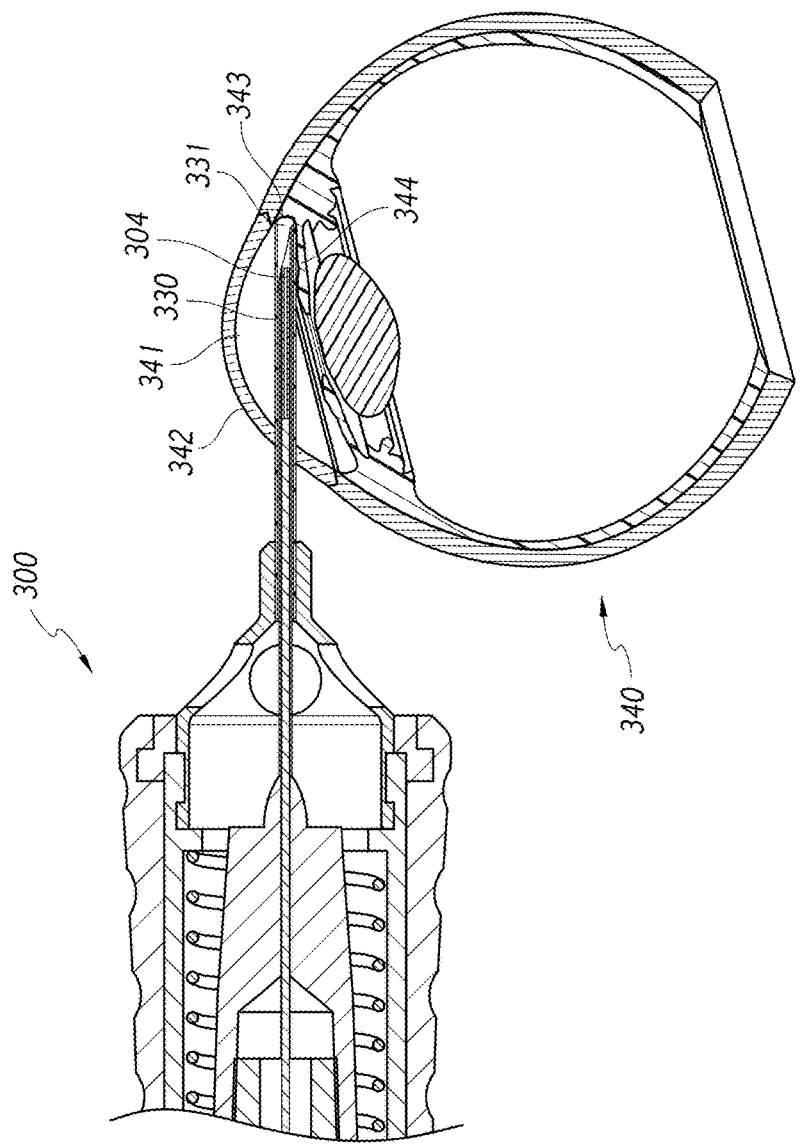
FIG. 24A shows a deployment device in an insertion configuration and fit into an anterior chamber of an eye.
Figure 24B:
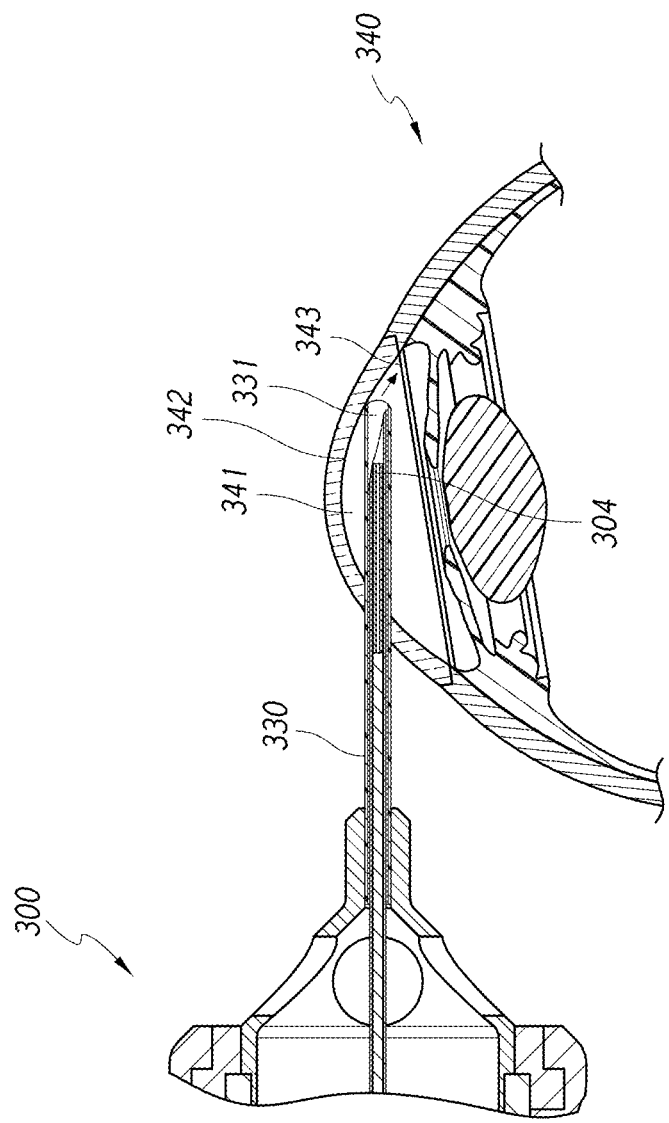
FIG. 24B shows a deployment device in an insertion configuration and inserted at too shallow an angled, thus abutting the sclera above the anterior chamber angle.
Figure 24C:
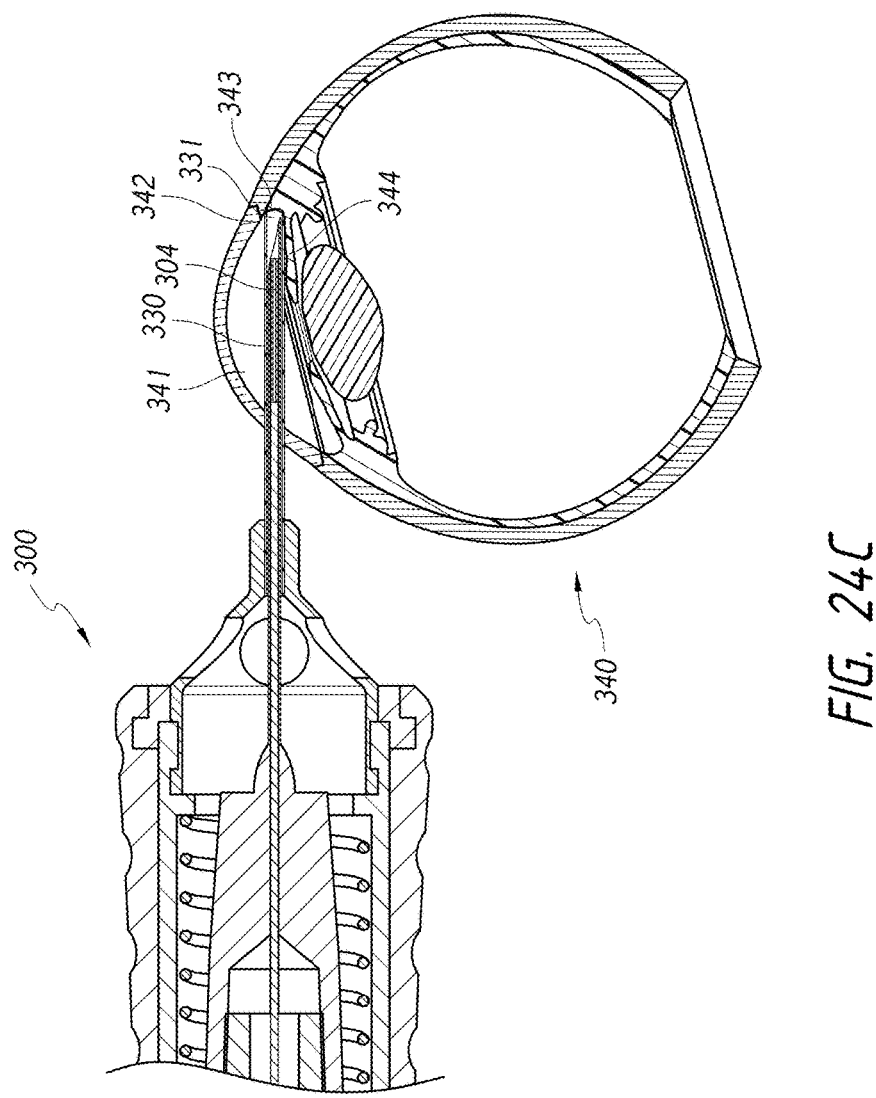
FIG. 24C shows a deployment device in an insertion configuration after the protrusion has caused the device to slide down the sclera and be fit into an anterior chamber of an eye.

Referring back to FIG. 22E, the angle of the top portion is substantially identical to an anterior chamber angle of an eye. Such a shape of the protrusion ensures that some embodiments of the device will also finds its way to fit, such as by conforming and sliding, into the anterior chamber angle of the eye, the place for proper deployment of an intraocular shunt. This is explained with reference to FIGS. 24A to 24E. FIG. 24A shows device 300 in an insertion configuration and inserted into an eye 340. In this figure, protrusion 331 at the distal end of the sleeve 330 has been advanced across the anterior chamber 341 to the sclera 342 on the opposite side of the eye 340 from which the device entered the eye 340. FIG. 24A shows protrusion 331 fitted within the anterior chamber angle 343 of the eye 340. If sleeve 330 enters the anterior chamber 341 at too shallow an angle, i.e., the protrusion 331 hit the sclera 342 above the anterior chamber angle 343, the angled top portion of the protrusion 331 causes the sleeve 330 to slide down the sclera 342 (direction of arrow) until the protrusion 331 is fit within the anterior chamber angle 343 of the eye 340 (FIGS. 24B and 24C). The sleeve 330 will slide down the sclera 342 instead of entering the sclera 342 at the contact point because the shaft 304 is completely disposed within the sleeve 330 and the protrusion 331 provides adequate surface area at the distal end of sleeve 330 to prevent enough force from being generated at the distal end of sleeve 330 that would result in sleeve 330 entering the sclera 342.

Figure 24D:
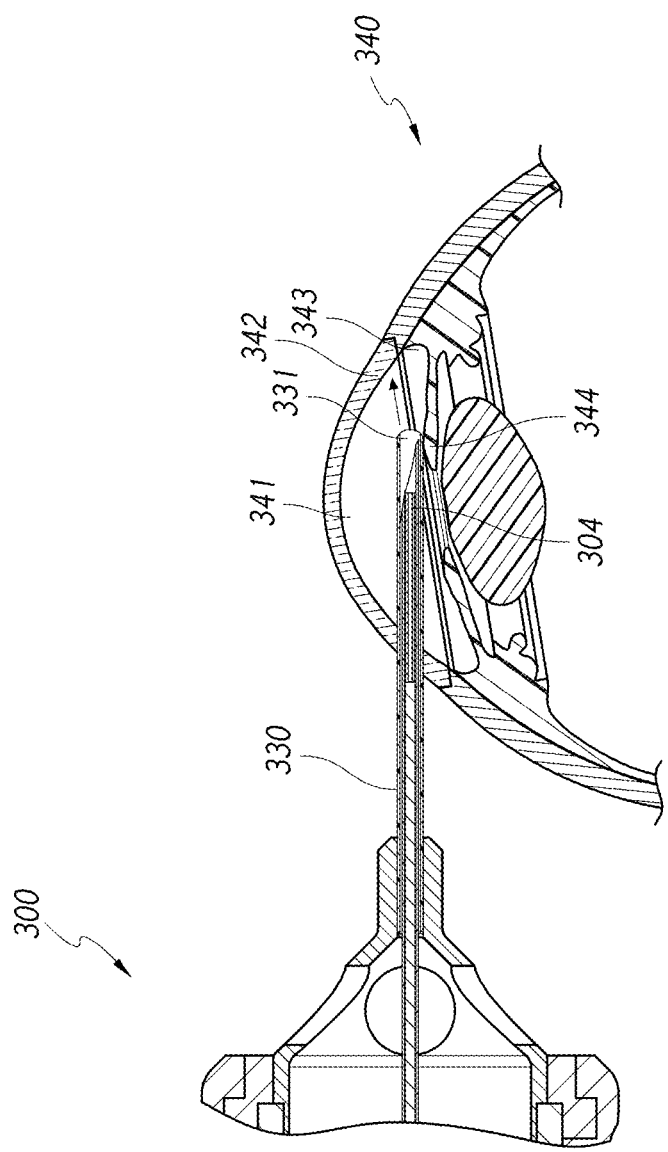
FIG. 24D shows a deployment device in an insertion configuration and inserted at too steep an angled, thus abutting the iris below the anterior chamber angle.
Figure 24E:
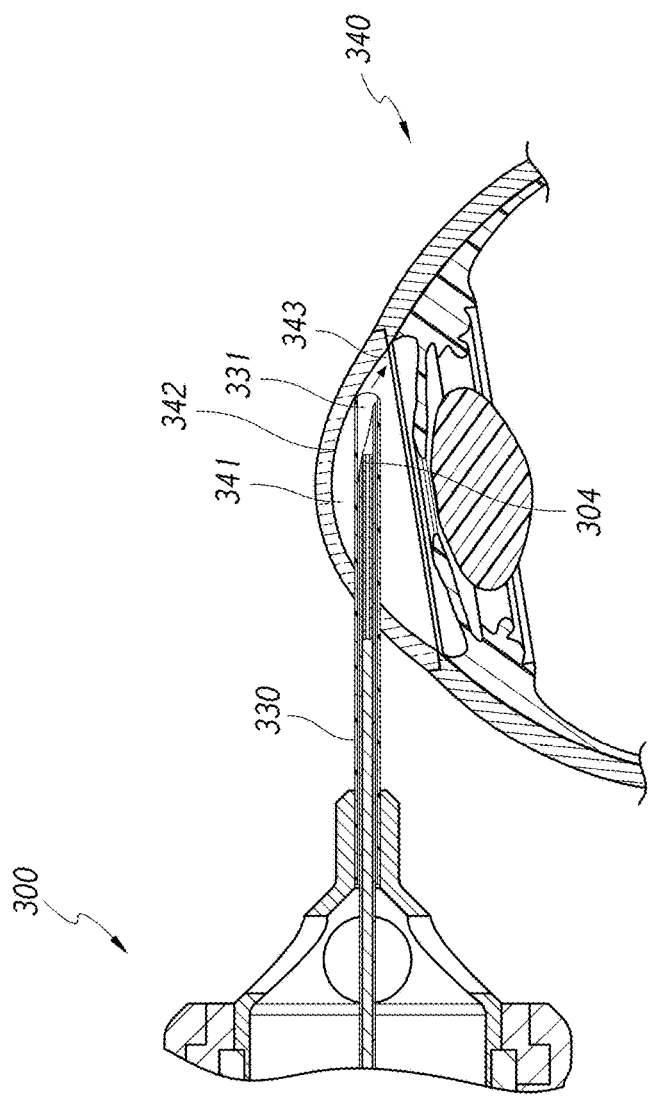
FIG. 24E shows a deployment device in an insertion configuration after the protrusion has caused the device to deflect off of the iris and slide along the iris and be fit into an anterior chamber of an eye.

Conversely, if sleeve 330 enters the anterior chamber 341 at too steep an angle, i.e., the protrusion 331 hit the iris 344 below the anterior chamber angle 343, the substantially flat bottom portion of the protrusion 331 causes the sleeve 330 to deflect off the iris 344 and proceed is a direction parallel to the iris 344 until the protrusion 331 is fit within the anterior chamber angle 343 of the eye 340 (FIGS. 24D and 24E). The sleeve 330 will deflect off the iris 344 instead of entering the iris 344 at the contact point because the shaft 304 is completely disposed within the sleeve 330 and the protrusion 331 provides adequate surface area at the distal end of sleeve 330 to prevent enough force from being generated at the distal end of sleeve 330 that would result in sleeve 330 entering the iris 344.

In certain embodiments, protrusion 331 is not required. In these embodiments, the sleeve 330 is of a sufficient outer diameter such that the sleeve itself may serve the function of the protrusion as described above. In these embodiments, a distal end of the sleeve is shaped to have a flat bottom portion and an angled top portion. In other embodiments, a goniolens can be used to visualize advancement of the device within the eye, and thus the configuration of the distal end of the sleeve 330 is not important for proper shunt deployment using some embodiments of the device.

Referring back to FIG. 22A, the proximal portion 301a of the housing 301 is open at its proximal end, such that a portion of a deployment mechanism 303 may extend from the proximal end of the proximal portion 301a of the housing 301. The sleeve 330 of the distal portion 301b of the housing 301 is also open such that at least a portion of a hollow shaft 304 may extend inside the housing, into sleeve 330 of the distal portion 301b of the housing 301, and extend beyond the distal end of the sleeve 330 in certain configurations (such as the deployment configuration). Housing 301 further includes a slot 306 through which an operator, such as a surgeon, using the device 300 may view an indicator 307 on the deployment mechanism 303.

Housing 301 and protrusion 331 may be made of any material that is suitable for use in medical devices. For example, housing 301 and protrusion 331 may be made of a lightweight aluminum or a biocompatible plastic material. Examples of such suitable plastic materials include polycarbonate and other polymeric resins such as DELRIN and ULTEM. In certain embodiments, housing 301 and protrusion 331 are made of a material that may be autoclaved, and thus allow for housing 301 and protrusion 331 to be re-usable. Alternatively, device 300, may be sold as a one-time-use device, and thus the material of the housing and the protrusion does not need to be a material that is autoclavable.

Deployment into the eye of an intraocular shunt, such as the shunts described herein, in accordance with some methods can be achieved using a hollow shaft configured to hold the shunt, as described herein. The hollow shaft can be coupled to a deployment device or part of the deployment device itself. Deployment devices that are suitable for use with some methods include but are not limited to the deployment devices described in U.S. Pat. Nos. 6,007,511, 6,544,249, and U.S. Pat. Pub. No. US2008/0108933, the contents of each of which are hereby incorporated by reference in their entireties. In other embodiments, the deployment devices are devices as described in co-pending and co-owned U.S. patent application Ser. No. 12/946,222 filed on Nov. 15, 2010, the entire content of which is incorporated by reference herein.

Figure 25:
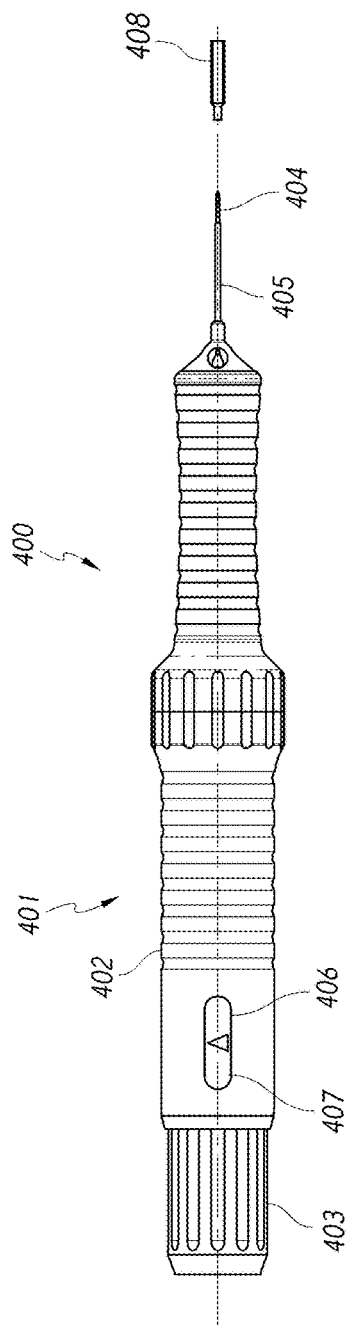
FIG. 25 is a schematic showing an embodiment of a shunt deployment device according to some embodiments.

In still other embodiments, some methods are conducted using the deployment device 400 depicted in FIG. 25. While FIG. 25 shows a handheld manually operated shunt deployment device, it will be appreciated that some embodiments of the device may be coupled with robotic systems and may be completely or partially automated. As shown in FIG. 25, deployment device 400 includes a generally cylindrical body or housing 401, however, the body shape of housing 401 could be other than cylindrical. Housing 401 may have an ergonomical shape, allowing for comfortable grasping by an operator. Housing 401 is shown with optional grooves 402 to allow for easier gripping by a surgeon.

Housing 401 is shown having a larger proximal portion that tapers to a distal portion. The distal portion includes a hollow sleeve 405. The hollow sleeve 405 is configured for insertion into an eye and to extend into an anterior chamber of an eye. The hollow sleeve is visible within an anterior chamber of an eye. The sleeve may include an edge at a distal end that provides resistance feedback to an operator upon insertion of the deployment device 400 within an eye of a person. Upon advancement of the device 400 across an anterior chamber of the eye, the hollow sleeve 405 will eventually contact the sclera, providing resistance feedback to an operator that no further advancement of the device 400 is necessary. The edge of the sleeve 405, prevents the shaft 404 from accidentally being pushed too far through the sclera. A temporary guard 408 is configured to fit around sleeve 405 and extend beyond an end of sleeve 405. The guard is used during shipping of the device and protects an operator from a distal end of a hollow shaft 404 that extends beyond the end of the sleeve 405. The guard is removed prior to use of the device.

Housing 401 is open at its proximal end, such that a portion of a deployment mechanism 403 may extend from the proximal end of the housing 401. A distal end of housing 401 is also open such that at least a portion of a hollow shaft 404 may extend through and beyond the distal end of the housing 401. Housing 401 further includes a slot 406 through which an operator, such as a surgeon, using the device 400 may view an indicator 407 on the deployment mechanism 403.

Housing 401 may be made of any material that is suitable for use in medical devices. For example, housing 401 may be made of a lightweight aluminum or a biocompatible plastic material. Examples of such suitable plastic materials include polycarbonate and other polymeric resins such as DELRIN and ULTEM. In certain embodiments, housing 401 is made of a material that may be autoclaved, and thus allow for housing 401 to be re-usable. Alternatively, device 400, may be sold as a one-time-use device, and thus the material of the housing does not need to be a material that is autoclavable.

Figure 26:
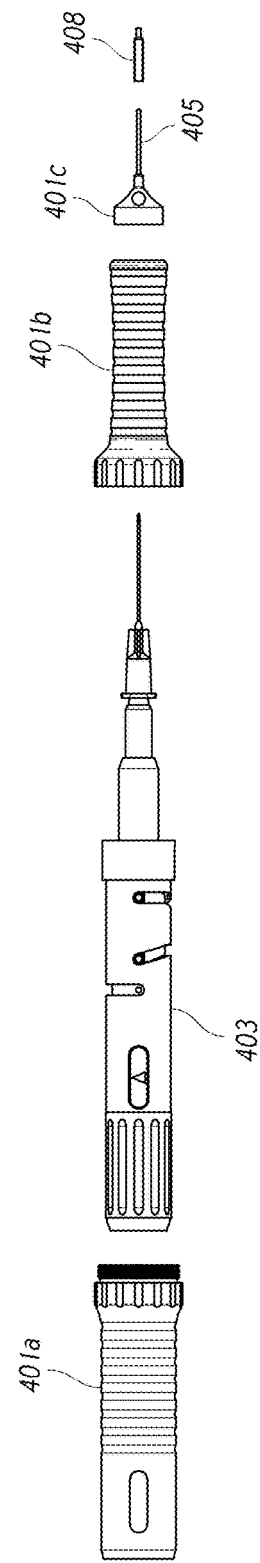
FIG. 26 shows an exploded view of the device shown in FIG. 25.
Figure 27A:
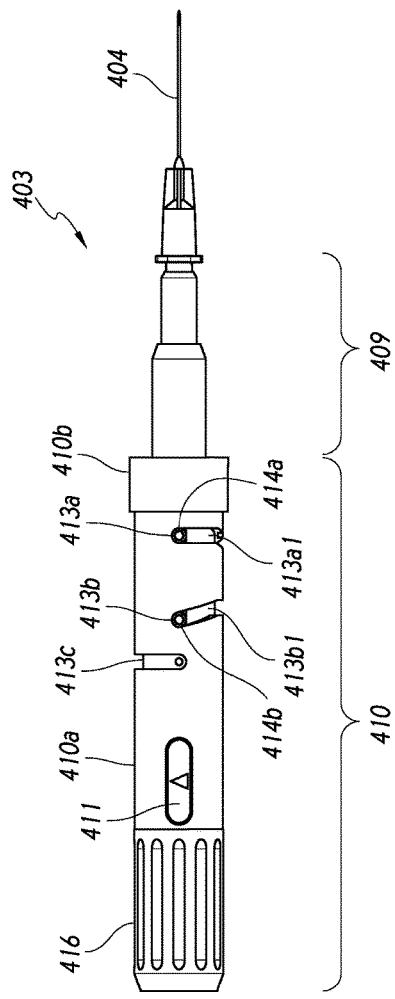
Figure 27B:
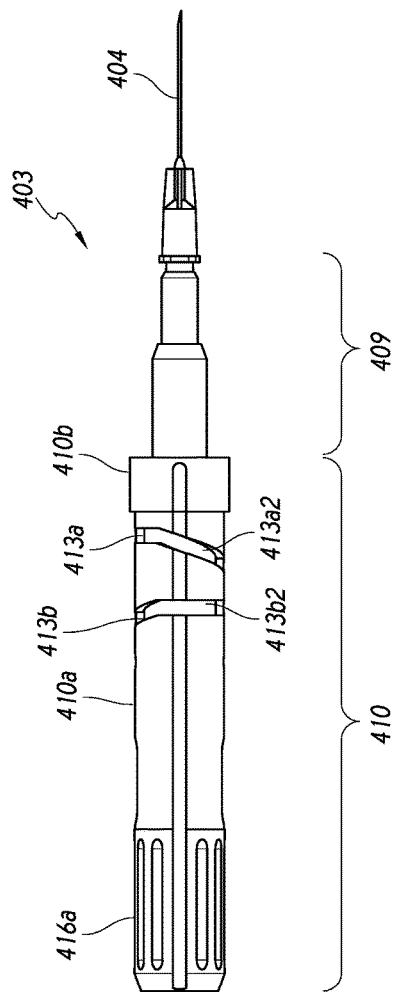

Housing 401 may be made of multiple components that connect together to form the housing. FIG. 26 shows an exploded view of deployment device 400. In this figure, housing 401, is shown having three components 401a, 401b, and 401c. The components are designed to screw together to form housing 401. FIG. 26 also shows deployment mechanism 403. The housing 401 is designed such that deployment mechanism 403 fits within assembled housing 401. Housing 401 is designed such that components of deployment mechanism 403 are movable within housing 401.

FIGS. 27A-27D also show deployment mechanism 403. The housing 401 is designed such that deployment mechanism 403 fits within assembled housing 401. Housing 401 is designed such that components of deployment mechanism 403 are movable within housing 401.

FIGS. 27A-27D show different enlarged views of the deployment mechanism 403. Deployment mechanism 403 may be made of any material that is suitable for use in medical devices. For example, deployment mechanism 403 may be made of a lightweight aluminum or a biocompatible plastic material. Examples of such suitable plastic materials include polycarbonate and other polymeric resins such as DELRIN and ULTEM. In certain embodiments, deployment mechanism 403 is made of a material that may be autoclaved, and thus allow for deployment mechanism 403 to be re-usable. Alternatively, device 400 may be sold as a one-time-use device, and thus the material of the deployment mechanism does not need to be a material that is autoclavable.

Deployment mechanism 403 includes a distal portion 409 and a proximal portion 410. The deployment mechanism 403 is configured such that distal portion 409 is movable within proximal portion 410. More particularly, distal portion 409 is capable of partially retracting to within proximal portion 410.

In this embodiment, the portion 409 is shown to taper to a connection with a hollow shaft 404. This embodiment is illustrated such that the connection between the hollow shaft 404 and the distal portion 409 of the deployment mechanism 403 occurs inside the housing 401. Hollow shaft 404 may be removable from the distal portion 409 of the deployment mechanism 403. Alternatively, the hollow shaft 404 may be permanently coupled to the distal portion 409 of the deployment mechanism 403.

Figure 29:
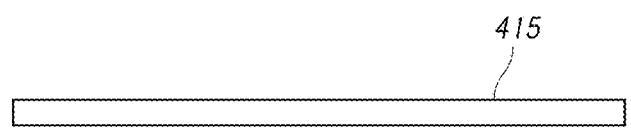
FIG. 29 depicts a schematic of an exemplary intraocular shunt.

Generally, hollow shaft 404 is configured to hold an intraocular shunt 415. An exemplary intraocular shunt 415 in shown in FIG. 29. Other exemplary intraocular shunts are shown in Yu et al. (U.S. Pat. Pub. No. 2008/0108933). Generally, in one embodiment, intraocular shunts are of a cylindrical shape and have an outside cylindrical wall and a hollow interior. The shunt may have an inner diameter of approximately 50 µm to approximately 250 µm, an outside diameter of approximately 190 µm to approximately 300 µm, and a length of approximately 0.5 mm to about 20 mm. Thus, hollow shaft 404 is configured to at least hold a shunt of such shape and such dimensions. However, hollow shaft 404 may be configured to hold shunts of different shapes and different dimensions than those described above, and some embodiments encompass a shaft 404 that may be configured to hold any shaped or dimensioned intraocular shunt. In particular embodiments, the shaft has an inner diameter of approximately 200 µm to approximately 400 µm. In certain embodiments, the shunt is a soft gel shunt, e.g., a gelatin shunt. If a gelatin shunt is used, the shunt is generally wetted inside the hollow shaft 404 with a balanced salt solution (e.g., Dulbecco's Phosphate Buffered Saline) or a steroid or other drug prior to implantation. Such priming ensures that the shunt remains flexible before implantation.

The shaft 404 may be any length. A usable length of the shaft may be anywhere from about 5 mm to about 40 mm, and is 15 mm in certain embodiments. In certain embodiments, the shaft is straight. In other embodiments, shaft 404 is of a shape other than straight, for example a shaft having a bend along its length or a shaft having an arcuate portion. Exemplary shaped shafts are shown for example in Yu et al. (U.S. Pat. Pub. No. 2008/0108933). In particular embodiments, the shaft includes a bend at a distal portion of the shaft. In other embodiments, a distal end of the shaft is beveled or is sharpened to a point.

The shaft 404 may hold the shunt at least partially within the hollow interior of the shaft 404. In other embodiments, the shunt is held completely within the hollow interior of the shaft 404. Alternatively, the hollow shaft may hold the shunt on an outer surface of the shaft 404. In particular embodiments, the shunt is held within the hollow interior of the shaft 404. In certain embodiments, the hollow shaft is a needle having a hollow interior. Needles that are configured to hold an intraocular shunt are commercially available from Terumo Medical Corp. (Elkington, Md.).

A proximal portion of the deployment mechanism 403 includes optional grooves 416 to allow for easier gripping by an operator for easier rotation of the deployment mechanism, which will be discussed in more detail below. The proximal portion 410 of the deployment mechanism also includes at least one indicator that provides feedback to an operator as to the state of the deployment mechanism. The indicator may be any type of indicator known in the art, for example a visual indicator, an audio indicator, or a tactile indicator. FIGS. 27A-27D show a deployment mechanism having two indicators, a ready indicator 411 and a deployed indicator 419. Ready indicator 411 provides feedback to an operator that the deployment mechanism is in a configuration for deployment of an intraocular shunt from the deployment device 400. The ready indicator 411 is shown in this embodiment as a green oval having a triangle within the oval. Deployed indicator 419 provides feedback to the operator that the deployment mechanism has been fully engaged and has deployed the shunt from the deployment device 400. The deployed indicator 419 is shown in this embodiment as a yellow oval having a black square within the oval. The indicators are located on the deployment mechanism such that when assembled, the indicators 411 and 419 may be seen through slot 406 in housing 401.

Figure 28A:
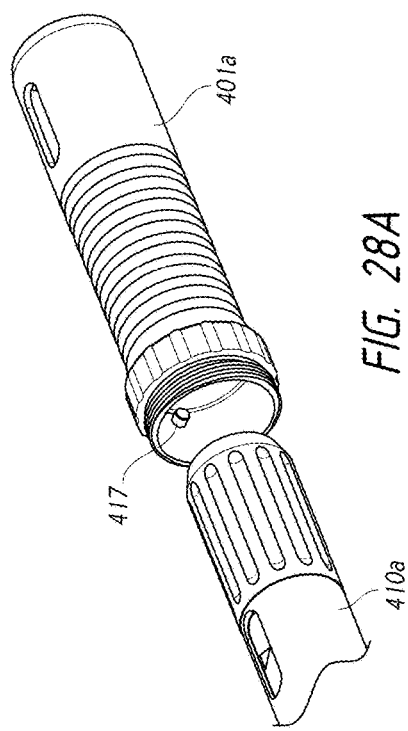
FIGS. 28A to 28C are schematics showing interaction of the deployment mechanism with a portion of the housing of the deployment device.
Figure 28B:
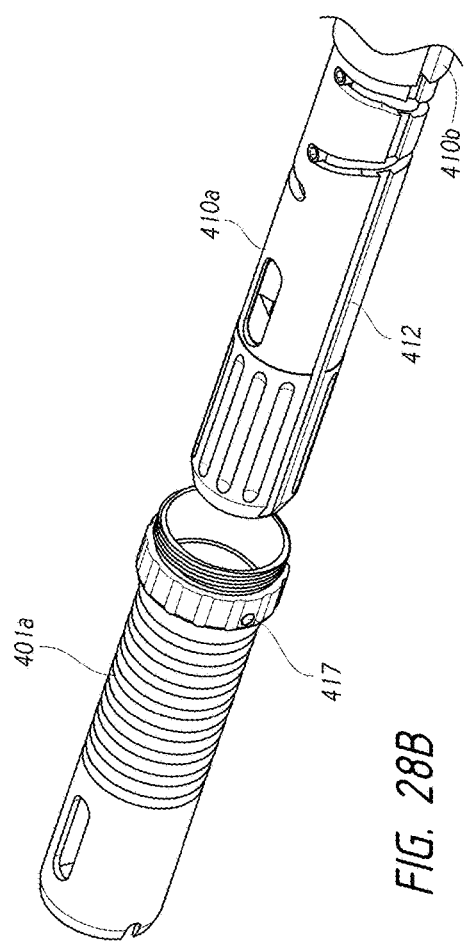
Figure 28C:
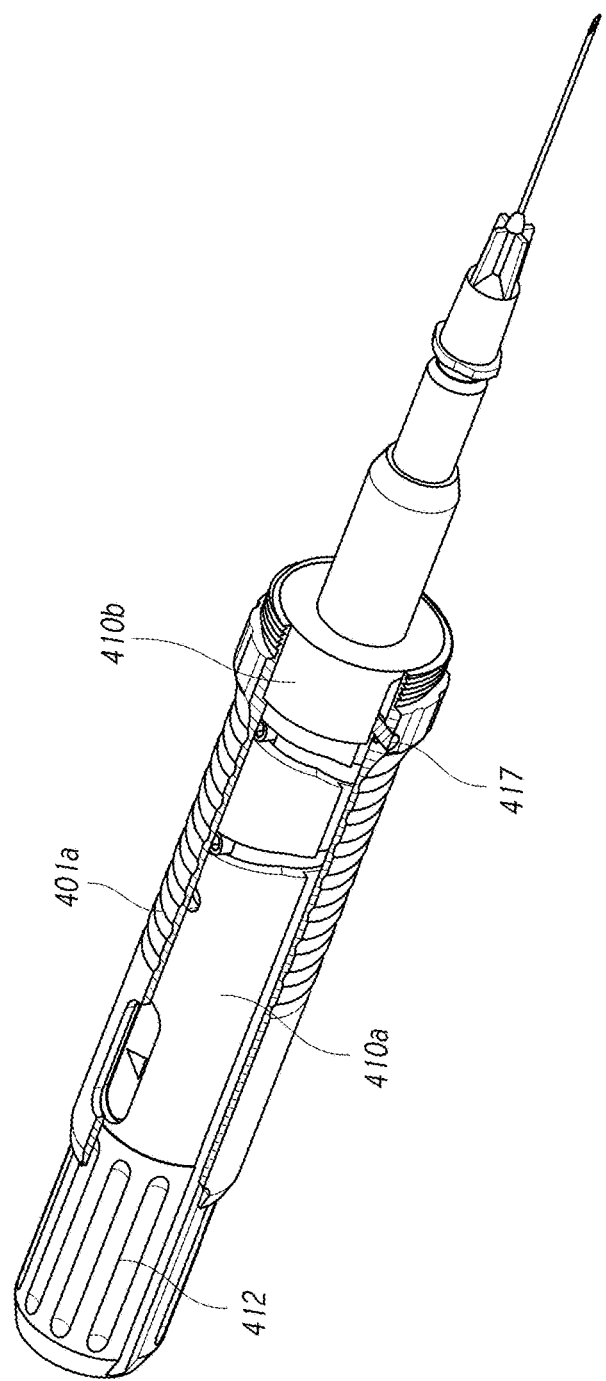

The proximal portion 410 includes a stationary portion 410b and a rotating portion 410a. The proximal portion 410 includes a channel 412 that runs part of the length of stationary portion 410b and the entire length of rotating portion 410a. The channel 412 is configured to interact with a protrusion 417 on an interior portion of housing component 401a (FIGS. 28A and 28B). During assembly, the protrusion 417 on housing component 401a is aligned with channel 412 on the stationary portion 410b and rotating portion 410a of the deployment mechanism 403. The proximal portion 410 of deployment mechanism 403 is slid within housing component 401a until the protrusion 417 sits within stationary portion 410b (FIG. 28C). Assembled, the protrusion 417 interacts with the stationary portion 410b of the deployment mechanism 403 and prevents rotation of stationary portion 410b. In this configuration, rotating portion 410a is free to rotate within housing component 401a.

Referring back to FIGS. 27A-27D, the rotating portion 410a of proximal portion 410 of deployment mechanism 403 also includes channels 413a, 413b, and 413c. Channel 413a includes a first portion 413a1 that is straight and runs perpendicular to the length of the rotating portion 410a, and a second portion 413a2 that runs diagonally along the length of rotating portion 410a, downwardly toward a proximal end of the deployment mechanism 403. Channel 413b includes a first portion 413b1 that runs diagonally along the length of the rotating portion 410a, downwardly toward a distal end of the deployment mechanism 403, and a second portion that is straight and runs perpendicular to the length of the rotating portion 410a. The point at which first portion 413a1 transitions to second portion 413a2 along channel 413a, is the same as the point at which first portion 413b1 transitions to second portion 413b2 along channel 413b. Channel 413c is straight and runs perpendicular to the length of the rotating portion 410a. Within each of channels 413a, 413b, and 413c, sit members 414a, 414b, and 414c respectively. Members 414a, 414b, and 414c are movable within channels 413a, 413b, and 413c. Members 414a, 414b, and 414c also act as stoppers that limit movement of rotating portion 410a, which thereby limits axial movement of the shaft 404.

Figure 30:
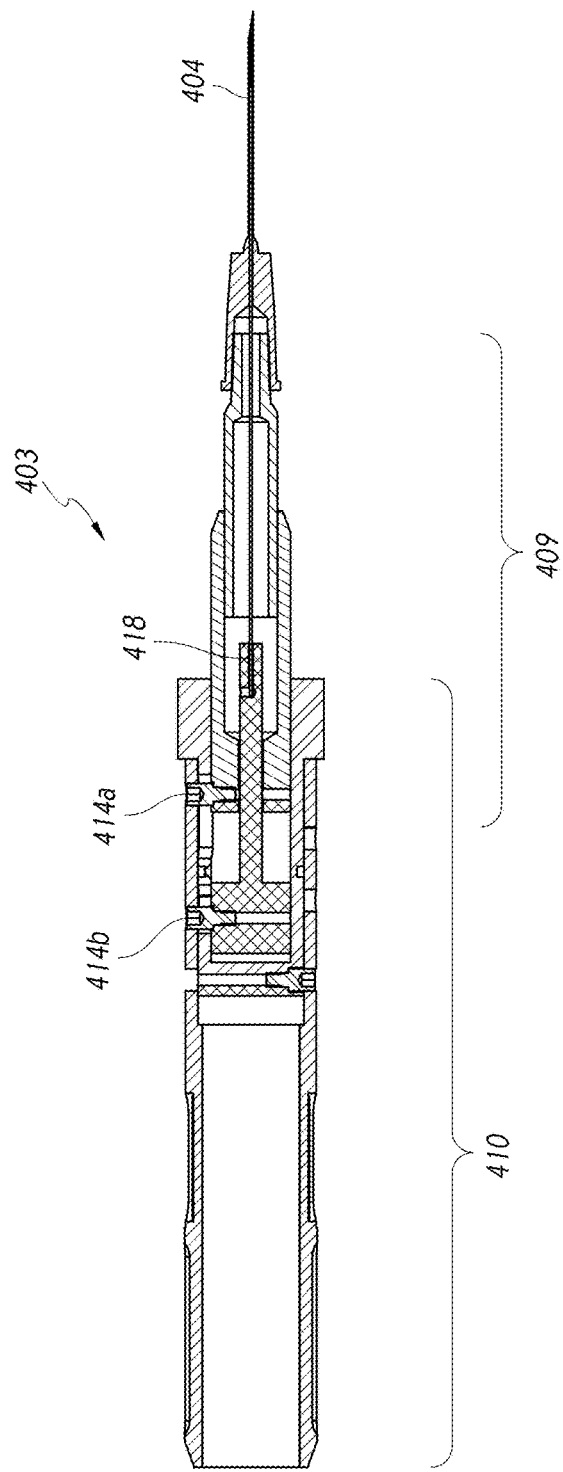
FIG. 30 shows a cross sectional view of the deployment mechanism of the deployment device with the shaft in a straight configuration, as if the shaft is within the stiff outer sleeve.

FIG. 30 shows a cross-sectional view of deployment mechanism 403. Member 414a is connected to the distal portion 409 of the deployment mechanism 403. Movement of member 414a results in retraction of the distal portion 409 of the deployment mechanism 403 to within the proximal portion 410 of the deployment mechanism 403. Member 414b is connected to a pusher component 418. The pusher component 418 extends through the distal portion 409 of the deployment mechanism 403 and extends into a portion of hollow shaft 404. The pusher component is involved in deployment of a shunt from the hollow shaft 404. An exemplary pusher component is a plunger. Movement of member 414b engages pusher 418 and results in pusher 418 advancing within hollow shaft 404.

Figure 31A:
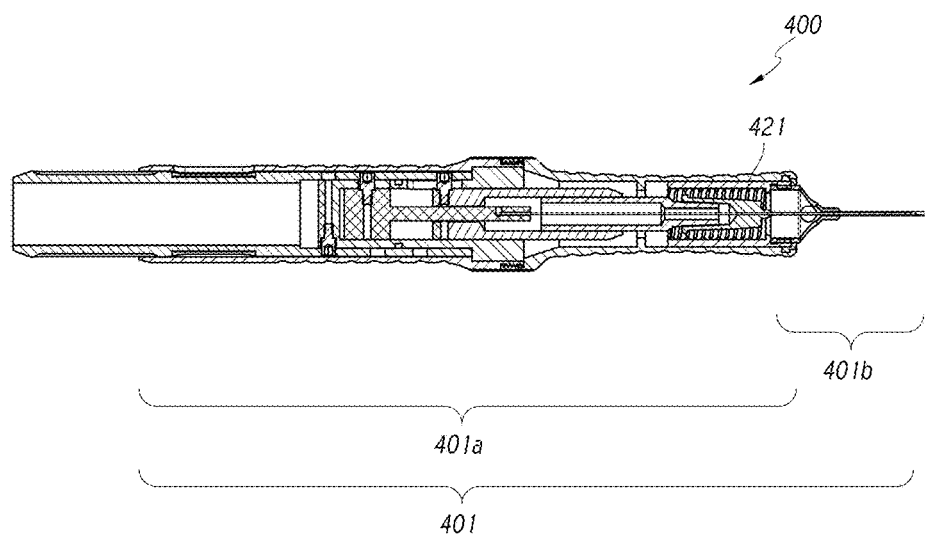
FIG. 31A is a schematic showing deployment some embodiments of the device in a pre-deployment or insertion configuration.
Figure 31B:
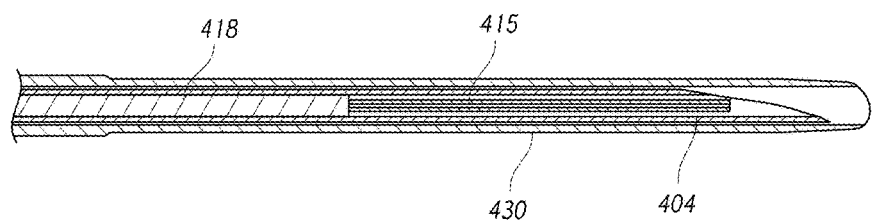
FIG. 31B shows an enlarged view of the distal portion of the deployment device of FIG. 31A. This figure shows an intraocular shunt loaded within a hollow shaft of the deployment device and that the shaft is completely disposed within the sleeve of the housing. In this configuration, the hollow shaft is straight.

Reference is now made to FIGS. 31A-31B, which accompany the following discussion regarding deployment of a shunt 415 from deployment device 400. FIG. 31A shows deployment device 400 in a pre-deployment or insertion configuration. In this configuration, shunt 415 is loaded within hollow shaft 404 (FIG. 31B). As shown in FIG. 31B, shunt 415 is only partially within shaft 404, such that a portion of the shunt is exposed. However, the shunt 415 does not extend beyond the end of the shaft 404. In other embodiments, the shunt 415 is completely disposed within hollow shaft 404. The shunt 415 is loaded into hollow shaft 404 such that the shunt abuts pusher component 418 within hollow shaft 404.

In the pre-deployment or insertion configuration, the distal portion 401b of the housing 401 is in an extended position, with spring 421 in a relaxed state (FIG. 31A). Additionally, in the pre-deployment configuration, the shaft 404 is fully disposed within the sleeve 430 of the distal portion 401b of the housing 401 (FIG. 31B). Pusher 418 abuts shunt 415 (FIG. 31B).

The deployment mechanism 403 is configured such that member 414a abuts a distal end of the first portion 413a1 of channel 413a, and member 414b abut a proximal end of the first portion 413b1 of channel 413b (FIG. 31C). In this configuration, the ready indicator 411 is visible through slot 406 of the housing 401, providing feedback to an operator that the deployment mechanism is in a configuration for deployment of an intraocular shunt from the deployment device 400 (FIG. 31D). In this configuration, the device 400 is ready for insertion into an eye (insertion configuration or pre-deployment configuration).

Figure 32A:
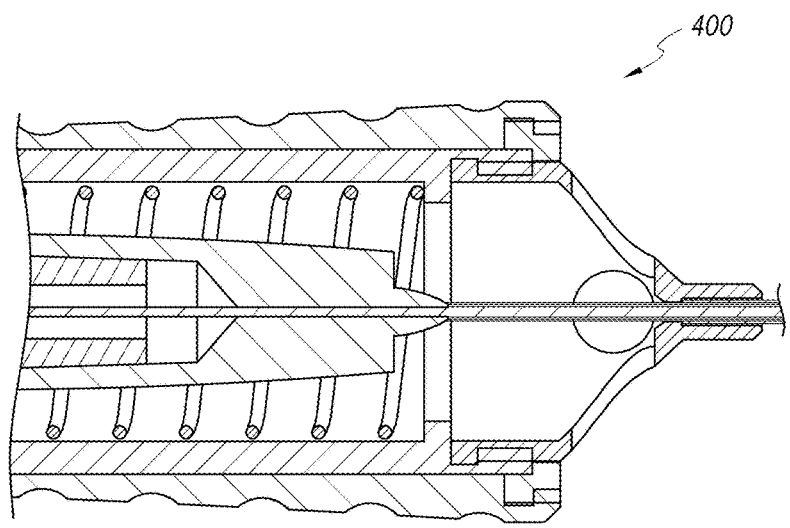
FIGS. 32A-32B are schematics showing insertion of a device into an anterior chamber of the eye, according to some embodiments.
Figure 32B:
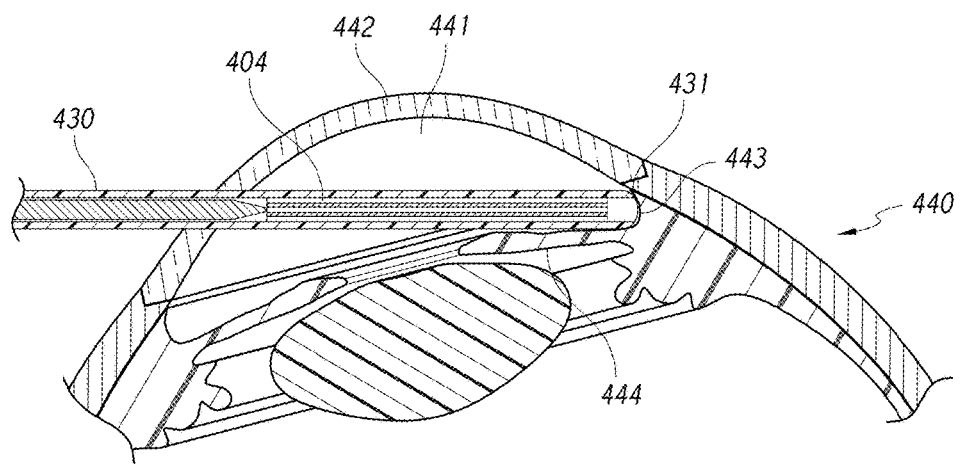

FIGS. 32A-32B show device 400 in the insertion configuration and inserted into an eye 440. FIG. 32A is a magnified view of the position of the distal portion 401b relative to the proximal portion 401a in the insertion configuration. FIG. 32B is a magnified view of the sleeve 430 of device 400 inserted into the eye. Any of a variety of methods known in the art may be used to insert some embodiments of the device into an eye. In certain embodiments, some embodiments of the device may be inserted into the eye using an ab externo approach (entering through the conjunctiva) or an ab interno approach (entering through the cornea). In particular embodiment, the approach is an ab interno approach as shown Yu et al. (U.S. Pat. No. 6,544,249 and U.S. Pat. Pub. No. 2008/0108933) and Prywes (U.S. Pat. No. 6,007,511), the content of each of which is incorporated by reference herein in its entirety.

FIGS. 32A-32B shows an ab interno approach for insertion of device 400 into the eye 440. In FIG. 32B, protrusion 431 at the distal end of the sleeve 430 has been advanced across the anterior chamber 441 to the anterior chamber angle 443 on the opposite side of the eye 440 from which the device entered the eye 440. FIG. 32B shows protrusion 431 and sleeve 430 fitted within the anterior chamber angle 443 of the eye 440, thus re-opening the partially or completely closed anterior chamber angle 443. Further, FIG. 32B illustrates that the protrusion 431 at the distal end of the sleeve 430 has been advanced across the anterior chamber 441 to the sclera 442 on the opposite side of the eye 440 from which the device entered the eye 440. FIG. 32B shows protrusion 431 and sleeve 430 fitted within the anterior chamber angle 443 of the eye 440. Such insertion and placement is accomplished without the use of an optical apparatus that contacts the eye, such as a goniolens. In certain embodiments this insertion is accomplished without the use of any optical apparatus.

Insertion without the use of an optical apparatus that contacts the eye, or any optical apparatus, is possible because of various features of the device described above and reviewed here briefly. The shape of the protrusion 431 is such that it corrects for an insertion angle that is too steep or too shallow, ensuring that the sleeve 430 is fitted into the anterior chamber angle of the eye, the place for proper deployment of an intraocular shunt. Further, the shape of the protrusion provides adequate surface area at the distal end of sleeve 430 to prevent enough force from being generated at the distal end of sleeve 430 that would result in sleeve 430 entering an improper portion of the sclera 442 (if the insertion angle is too shallow) or entering an improper portion of the iris 444 (if the insertion angle is too steep). Additionally, since the hollow shaft 404 is fully disposed within the sleeve 430, it cannot pierce tissue of the eye until it is extended from the sleeve 430. Thus, if the insertion angle is too shallow or too steep, the protrusion 431 can cause movement and repositioning of the sleeve 430 so that the sleeve 430 is properly positioned to fit in the anterior chamber angle of the eye for proper deployment of the shunt. Due to these features of device 400, some embodiments of the device provide for deploying intraocular shunts without use of an optical apparatus that contacts the eye, preferably without use of any optical apparatus.

Figure 33A:
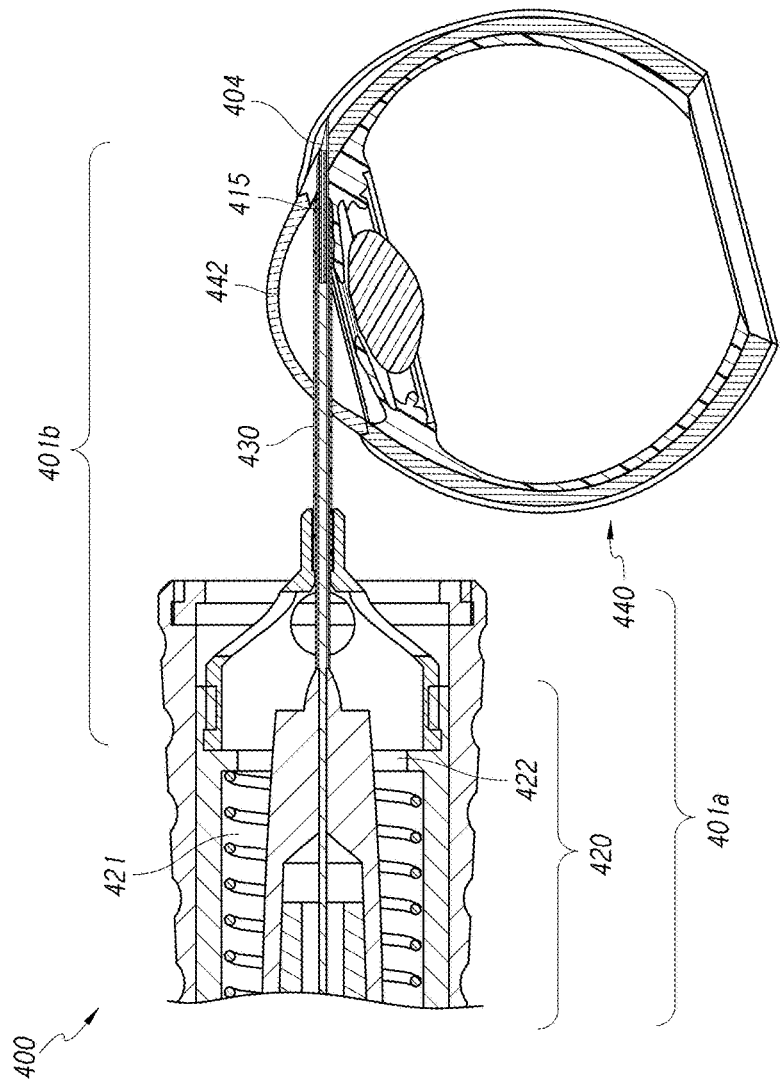
FIG. 33A is a schematic showing extension of the shaft from within the sleeve, which is accomplished by partial retraction of the distal portion of housing to within the proximal portion of housing.

Once the device has been inserted into the eye and the protrusion 431 and the sleeve 430 are fitted within the anterior chamber angle of the eye, the hollow shaft 404 may be extended from within the sleeve 430. Referring now to FIG. 33A which show extension of the hollow shaft 404 from within the sleeve 430, which is accomplished by partial retraction of distal portion 401b of housing 401 to within proximal portion 401a of housing 401 (FIG. 33A).

Refraction of the distal portion 401b of housing 401 to within proximal portion 401a of housing 401 is accomplished by an operator continuing to apply force to advance device 400 after the protrusion 431 and the sleeve 430 are fitted within the anterior chamber angle of the eye. The surface area of protrusion 431 prevents the application of the additional force by the operator from advancing sleeve 430 into the sclera 434. Rather, the additional force applied by the operator results in engagement of spring mechanism 420 and compression of spring 421 within spring mechanism 420. Compression of spring 420 results in retraction of distal portion 401b of housing 401 to within proximal portion 401a of housing 401. The amount of retraction of distal portion 401b of housing 401 to within proximal portion 401a of housing 401 is limited by member 422 that acts as a stopper and limits axial retraction of distal portion 401b within proximal portion 401a.

Figure 33B:
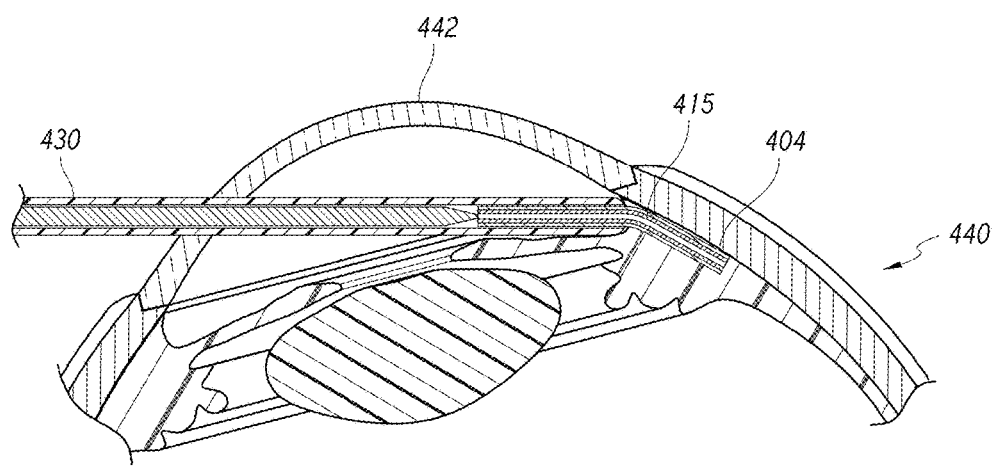
FIG. 33B is a magnified view of the sleeve of the device inserted into the eye, following a procedure as shown in FIG. 33A.

Refraction of distal portion 401b of housing 401 to within proximal portion 401a of housing 401 results in extension of hollow shaft 404, which now extends beyond the distal end of sleeve 430 and advances through the sclera 442 to an area of lower pressure than the anterior chamber (see e.g., FIG. 33B).

In FIG. 33A, a distal end of the shaft is shown to be located within the intra-Tenon's space. Within an eye, there is a membrane known as the conjunctiva, and the region below the conjunctiva is known as the subconjunctival space. Within the subconjunctival space is a membrane known as Tenon's capsule. Below Tenon's capsule there are Tenon's adhesions that connect the Tenon's capsule to the sclera. The space between Tenon's capsule and the sclera where the Tenon's adhesions connect the Tenon's capsule to the sclera is known as the intra-Tenon's space. This figure is exemplary and depicts only one embodiment for a location of lower pressure. It will be appreciated that some embodiments of the device may deploy shunts to various different locations of the eye and are not limited to deploying shunts to the intra-Tenon's space is shown by way of example in this figure. In this configuration, the shunt 415 is still completely disposed within the shaft 404.

The distal end of shaft 404 may be beveled to assist in piercing the sclera and advancing the distal end of the shaft 404 through the sclera. In this figure, the distal end of the shaft 404 is shown to have a double bevel (See also FIG. 31B). The double bevel provides an angle at the distal end of the shaft 404 such that upon entry of the shaft into intra-Tenon's space, the distal end of shaft 404 will by parallel with Tenon's capsule and will thus not pierce Tenon's capsule and enter the subconjunctival space. This ensures proper deployment of the shunt such that a distal end of the shunt 415 is deployed within the intra-Tenon's space, rather than deployment of the distal end of the shunt 415 within the subconjunctival space. Changing the angle of the bevel allows for placement of shunt 415 within other areas of lower pressure than the anterior chamber, such as the subconjunctival space. It will be understood that FIG. 33A-33B is merely one embodiment of where shunt 415 may be placed within the eye, and that some embodiments of the device are not limited to placing shunts within intra-Tenon's space and may be used to place shunts into many other areas of the eye, such as Schlemm's canal, the subconjunctival space, the episcleral vein, or the suprachoroidal space.

Referring to FIG. 33B, as noted above, retraction of distal portion 401b of housing 401 to within proximal portion 401a of housing 401 results in extension of hollow shaft 404, which now extends beyond the distal end of sleeve 430 and advances through the sclera 442. In accordance with some embodiments, the rigidity of the sleeve 430 holds hollow shaft 404 in a straight configuration. Upon its exposure from the sleeve 430, hollow shaft 404 reverts to its pre-bent configuration, which bend minors the angle or arc of the sclera. Such a pre-bend allows the hollow shaft 404 to follow the scleral spur down along the sclera in a self-guided manner to the suprachoroidal space. Generally, the bend in the hollow shaft 404 will be from about 5° degrees to about 70° degrees.

Additionally, the flexibility of the hollow shaft 404 allows it to continually bend and flex in response to the anatomy as the hollow shaft 404 advances from the sleeve 430. The hollow shaft 404 is advanced until a distal portion of the hollow shaft 404 is within the suprachoroidal space. In this configuration, the shunt 415 is still completely disposed within the shaft 404. The distal end of hollow shaft 404 may be beveled to assist in piercing the sclera and advancing the distal end of the hollow shaft 404 through the sclera.

At this point, an amount of BSS/steroid or other drug can be optionally injected through the hollow shaft and implant into a lower end of the target space to create a primed space for outflow and to deliver antifibrotic or other drugs to that new drainage space.

Reference is now made to FIGS. 34A to 34D. After extension of hollow shaft 404 from sleeve 430, the shunt 415 may be deployed from the device 400. The deployment mechanism 403 is a two-stage system. The first stage is engagement of the pusher component 418 and the second stage is retraction of the distal portion 409 of deployment mechanism 403 to within the proximal portion 410 of the deployment mechanism 403. Rotation of the rotating portion 410a of the proximal portion 410 of the deployment mechanism 403 sequentially engages the pusher component and then the retraction component.

In the first stage of shunt deployment, the pusher component is engaged and the pusher partially deploys the shunt from the deployment device. During the first stage, rotating portion 410a of the proximal portion 410 of the deployment mechanism 403 is rotated, resulting in movement of members 414a and 414b along first portions 413a1 and 413b1 in channels 413a and 413b. Since the first portion 413a1 of channel 413a is straight and runs perpendicular to the length of the rotating portion 410a, rotation of rotating portion 410a does not cause axial movement of member 414a. Without axial movement of member 414a, there is no retraction of the distal portion 409 to within the proximal portion 410 of the deployment mechanism 403. Since the first portion 413b1 of channel 413b runs diagonally along the length of the rotating portion 410a, upwardly toward a distal end of the deployment mechanism 403, rotation of rotating portion 410a causes axial movement of member 414b toward a distal end of the device. Axial movement of member 414b toward a distal end of the device results in forward advancement of the pusher component 418 within the hollow shaft 404. Such movement of pusher component 418 results in partially deployment of the shunt 415 from the shaft 404.

Figure 34C:
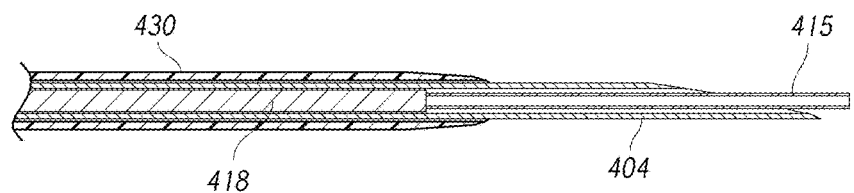
FIG. 34C shows an enlarged view of the distal portion of the deployment device of FIG. 34A. This figure shows an intraocular shunt partially deployed from within a hollow shaft of the deployment device.
Figure 34D:
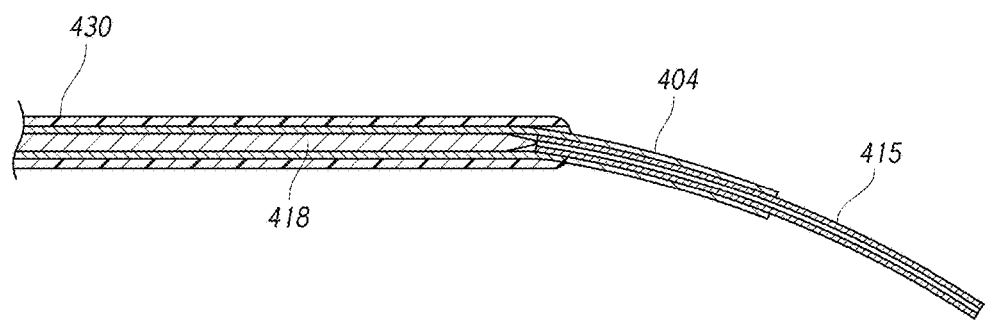
FIG. 34D shows an enlarged view of the distal portion of the deployment device of FIG. 34A, in which the shaft is shown exposed from the sleeve and is in a bent configuration. This figure shows an intraocular shunt partially deployed from within a hollow shaft of the deployment device.

FIGS. 34A-34C show schematics of the deployment mechanism at the end of the first stage of deployment of the shunt from the deployment device. FIGS. 34A-34B show the shaft in a straight configuration, as if it is within the stiff outer sleeve. As is shown FIG. 34A, members 414a and 414b have finished traversing along first portions 413a1 and 413b1 of channels 413a and 413b. Additionally, pusher component 418 has advanced within hollow shaft 404 (FIG. 34B), and shunt 415 has been partially deployed from the hollow shaft 404 (FIG. 34C). As is shown in FIG. 34D, a portion of the shunt 415 extends beyond an end of the shaft 404.

Figure 35A:
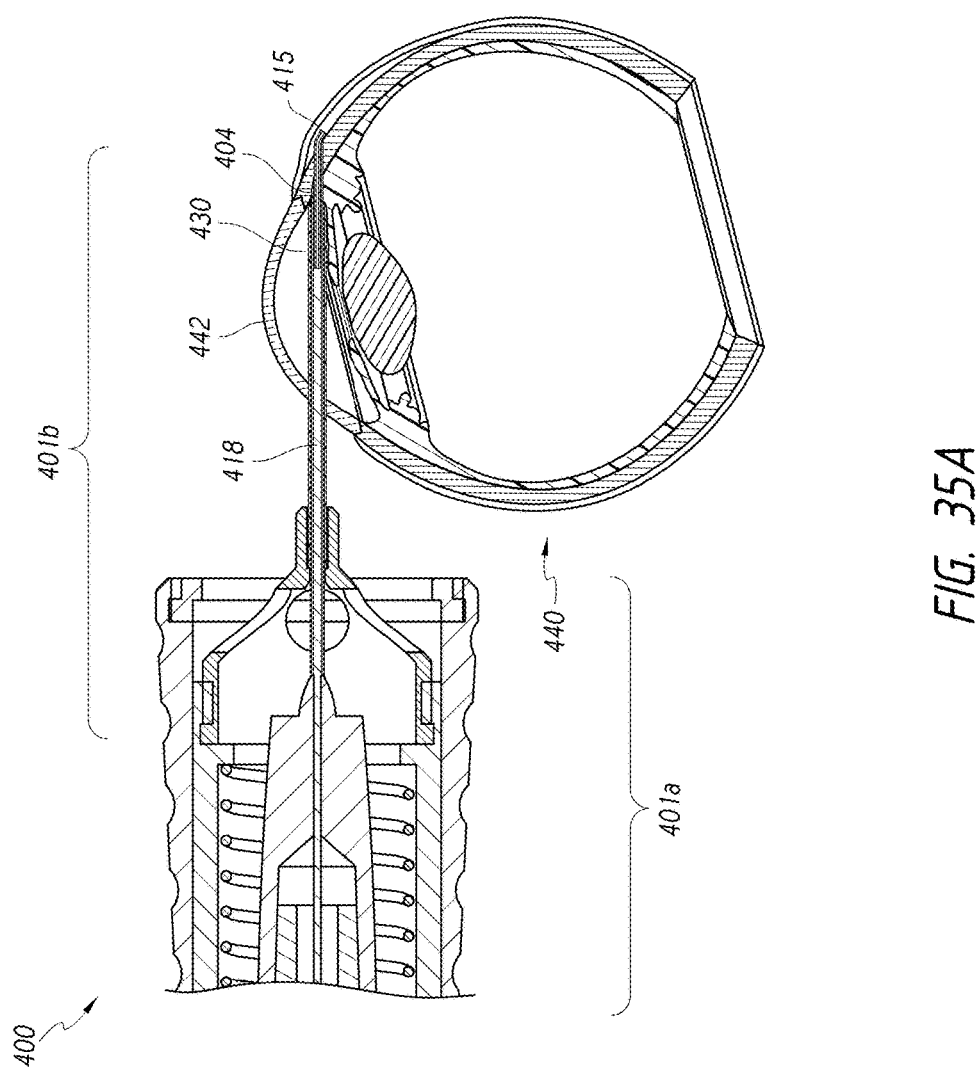
FIG. 35A-35B are schematics showing the deployment device after completion of the first stage of deployment of the shunt from the device and in to the eye.
Figure 35B:
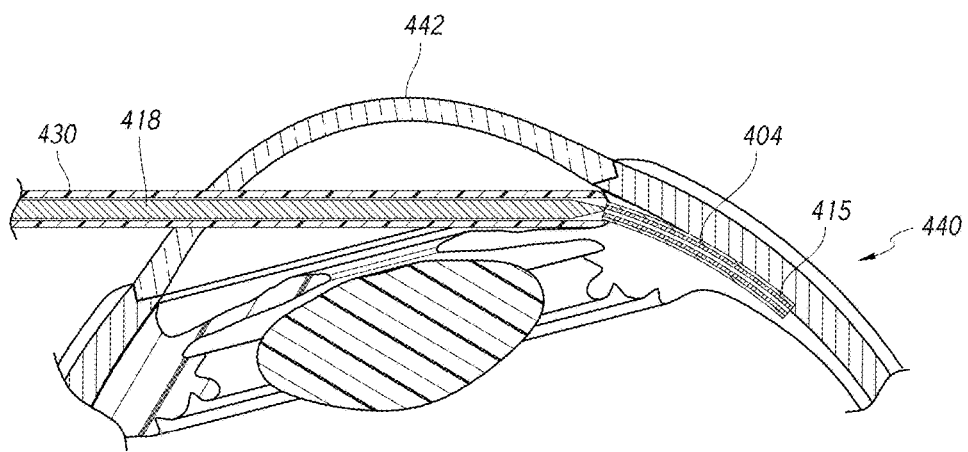

FIGS. 35A-35B show device 400 at the end of the first stage of deployment of the shunt 415 from device 400 and into the eye 440. This figure shows that the distal portion 401b of the housing 401 remains refracted within the proximal portion 401a of the housing 401, and that the hollow shaft 404 remains extended from the sleeve 430. As is shown in these figures, pusher 418 has been engaged and, which allows shunt 415 to be deployed from the hollow shaft 404. A portion of the shunt 415 can extend beyond an end of the shaft 404 and be located in the intra-Tenon's space.

Reference is now made to FIGS. 36A-36D. In the second stage of shunt deployment, the retraction component of deployment mechanism is engaged and the distal portion of the deployment mechanism is retracted to within the proximal portion of the deployment mechanism, thereby completing deployment of the shunt from the deployment device. During the second stage, rotating portion 410a of the proximal portion 410 of the deployment mechanism 403 is further rotated, resulting in movement of members 414a and 414b along second portions 413a2 and 413b2 in channels 413a and 413b. Since the second portion 413b2 of channel 413b is straight and runs perpendicular to the length of the rotating portion 410a, rotation of rotating portion 410a does not cause axial movement of member 414b. Without axial movement of member 414b, there is no further advancement of pusher 418. Since the second portion 413a2 of channel 413a runs diagonally along the length of the rotating portion 410a, downwardly toward a proximal end of the deployment mechanism 403, rotation of rotating portion 410a causes axial movement of member 414a toward a proximal end of the device. Axial movement of member 414a toward a distal proximal end of the device results in retraction of the distal portion 409 to within the proximal portion 410 of the deployment mechanism 403. Retraction of the distal portion 409, results in retraction of the hollow shaft 404. Since the shunt 415 abuts the pusher component 418, the shunt remains stationary as the hollow shaft 404 retracts from around the shunt 415. The hollow shaft 404 retracts completely to within the sleeve 430 of the distal portion 401b of the housing 401. During both stages of the deployment process, the sleeve 430 remains stationary and in a fixed position.

Referring to FIGS. 36A-36D, which show schematics of the deployment mechanism at the end of the second stage of deployment of the shunt from the deployment device. As is shown in FIG. 36A, members 414a and 414b have finished traversing along second portions 413a2 and 413b2 of channels 413a and 413b. Additionally, distal portion 409 has retracted to within proximal portion 410, thus resulting in retraction of the hollow shaft 404 to within the sleeve 430. FIG. 36A shows the shaft in a straight configuration, after it has been refracted into the stiff outer sleeve.

FIGS. 36B to 36D show a schematic of the device 400 in the eye 430 after the second stage of deployment has been completed. FIG. 36B shows that the distal portion 401b of the housing 401 remains retracted within the proximal portion 401a of the housing 401. As is shown in FIGS. 36B and 36C, shaft 404 has withdrawn through the sclera 434 to be fully retracted to within sleeve 430. At completion of the second stage of deployment, a distal portion of the shunt 415 has been deployed and resides in the intra-Tenon's space (see FIG. 36B) or in the suprachoroidal space (see FIG. 36C), a middle portion of the shunt 415 spans the sclera, and a proximal portion of shunt 415 has been deployed from shaft 404 yet still resides within sleeve 430. The proximal portion of the shunt 415 still abuts pusher 418.

Referring to FIG. 36D, in the post-deployment configuration, the deployed indicator 419 is visible through slot 406 of the housing 401, providing feedback to the operator that the deployment mechanism 403 has been fully engaged and that the deployment mechanism 403 has completed its second stage of deployment.

Referring to FIG. 37A-37B, which show schematics of the device 400 after completion of deployment of the shunt 415 from the device 400 and in to the eye 440. After completion of the second stage of the deployment by the deployment mechanism 403, as indicated to the operator by visualization of deployed indicator 419 through slot 406 of the housing 401, the operator may pull the device 400 from the eye 440. Backward force by the operator reengages spring mechanism 420 and results in uncoiling of spring 421 (FIG. 37A). Uncoiling of spring 421 proceeds as the proximal portion 401a of housing 401 is pulled from the eye 440. Such action causes distal portion 401b to return to its extended state within proximal portion 401a of housing 401 (FIG. 37A). Continued backward force by the operator continues to pull the device 400 from the eye 440. As the device 400 is continued to be pulled from the eye, the sleeve 430 is also pulled backward and the proximal portion of the shunt 415 is exposed from within the sleeve 430 and resides within the anterior chamber 441 of the eye 440 (FIG. 37B). The operator continues to apply backward force until the device 400 is completely withdrawn from the eye 440. At this point, in some embodiments, a distal portion of the shunt 415 has been deployed and can reside in the suprachoroidal space (see FIGS. 36C and 37B), a middle portion of the shunt 415 spans the sclera, and a proximal portion of shunt 415 has been deployed and resides in the anterior chamber.

Three Stage Deployment Mechanism

Another embodiment by which the hollow shaft 404 may be extended from the sleeve 430 involves a deployment mechanism that is a three-stage mechanism. The three-stage mechanism operates similarly to the above described device that uses a spring loaded distal portion and a two-stage deployment mechanism. In the three-stage system, the channels of the deployment mechanism are extended to accommodate the new first stage. The newly added portion of the channels run diagonally upward along the length of the rotating portion toward the proximal end of the deployment mechanism. Axial movement by the members within the channels results in the extension of the hollow shaft 404 from the sleeve 430. The new first stage replaces the spring loaded distal portion and results in extension of the hollow shaft 404 from the sleeve 430. The engagement of the pusher component 418 becomes the second stage and retraction of the distal portion 409 of deployment mechanism 403 to within the proximal portion 410 of the deployment mechanism 403 becomes the third stage. The second and third stages of the three-stage system are the same as the first and second stages of the two-stage system and operate as described above. Rotation of the rotating portion of the distal portion of the deployment mechanism sequentially extends the hollow shaft from the sleeve, engages the pusher component and then engages the retraction component.

Referring now to FIGS. 38A-38E, the sleeve 505 may include an edge 531 at a distal end that provides resistance feedback to an operator upon insertion of the deployment device 500 within an eye 532 of a person during delivery of the shunt 515. Upon advancement of the device 500 across an anterior chamber 533 of the eye 532, the hollow sleeve 505 will eventually contact the sclera 534, providing resistance feedback to an operator that no further advancement of the device 500 is necessary. The edge 531 of the sleeve 505 prevents the shaft 504 from accidentally being pushed too far through the sclera 534.

Combinations of Embodiments

As will be appreciated by one skilled in the art, individual features of some embodiments may be used separately or in any combination. Particularly, it is contemplated that one or more features of the individually described above embodiments may be combined into a single shunt.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The inventions may be embodied in other specific forms without departing from the spirit or essential characteristics thereof. The foregoing embodiments are therefore to be considered in all respects illustrative rather than limiting on the inventions described herein.

What is claimed is:

1. A device for deploying an intraocular shunt, the device comprising:
   a housing;
   a sleeve coupled to the housing;
   a needle (i) positioned at least partially within the sleeve and (ii) configured to hold an intraocular shunt;
   a pusher component axially movable within the needle;
   a retraction component configured to retract the needle inside the housing; and
   a rotatable deployment portion configured to rotate in a first direction to sequentially move the pusher component and to continue rotation in the first direction to subsequently engage with and move the retraction component.

2. The device according to claim 1, wherein a distal portion of the housing is movable (i) relative to the pusher component, the retraction component, and the needle and (ii) between a distal position and a proximal position, the distal portion being biased toward the distal position.

3. The device according to claim 2, further comprising a member that limits axial retraction of the distal portion of the housing.

4. The device according to claim 2, wherein the distal portion further comprises a capsule, the capsule being at least partially within a proximal portion of the housing when the distal portion is in the proximal position.

5. The device according to claim 2, wherein a distal end of the needle extends distally from the sleeve when the distal portion is in the proximal position.

6. The device according to claim 1, further comprising an intraocular shunt that is at least partially disposed within the needle.

7. The device according to claim 6, wherein the pusher component is configured to push the shunt partially out of the needle, and the retraction component is configured to retract the needle relative to the shunt.

8. The device according to claim 1, further comprising at least one member that limits axial movement of the needle.

9. The device according to claim 1, further comprising an indicator mechanism formed on the housing that provides feedback to an operator as to a position of at least one of the pusher component or the retraction component.

10. The device according to claim 9, wherein the indicator mechanism comprises a slot, formed in and extending along the housing, for providing a visual indication of the position of at least one of the pusher component or the retraction component.

11. The device according to claim 1, wherein the rotatable deployment portion is configured to rotate about a longitudinal axis of the device in the first direction to sequentially move the pusher component and to continue rotation in the first direction to subsequently move the retraction component.

12. A device for deploying an intraocular shunt, the device comprising:
a housing comprising a sleeve, the sleeve comprising a distal contact surface that provides resistance against advancement of the device when the contact surface contacts anterior chamber angle tissue on an inside of an anterior chamber;
a deployment mechanism at least partially disposed within the housing; and
a needle coupled inside the housing to the deployment mechanism, wherein the needle is configured to hold an intraocular shunt;
wherein the device comprises an insertion configuration and a deployment configuration and, when the device is in the insertion configuration, the needle extends distally beyond the sleeve, and when the device is in the deployment configuration, the needle is fully disposed within the sleeve; and
wherein the deployment mechanism is configured to rotate in a first direction to sequentially push the shunt within the needle and to continue rotation in the first direction to subsequently engage with and retract the needle relative to the housing.

13. The device according to claim 12, wherein the contact surface comprises a radial protrusion.

14. The device according to claim 13, wherein the protrusion is formed integrally with a distal end of the sleeve.

15. The device according to claim 13, wherein the protrusion is formed separately from the sleeve and connected to a distal end of the sleeve.

16. The device according to claim 12, wherein the contact surface surrounds a distal end of the sleeve.

17. The device according to claim 12, wherein the contact surface extends around only a portion of the sleeve.

18. The device according to claim 12, wherein the contact surface comprises a collar that surrounds a distal end of the sleeve.

19. The device according to claim 12, wherein the deployment mechanism is configured to rotate about a longitudinal axis of the device in the first direction to sequentially push the shunt within the needle and to continue rotation in the first direction to subsequently retract the needle relative to the housing.

20. A device for deploying an intraocular shunt, the device comprising:
a housing comprising a sleeve;
a deployment mechanism at least partially disposed within the housing; and
a needle extending within the sleeve and coupled to the deployment mechanism, the needle being configured to hold an intraocular shunt, the needle being fully disposed within the sleeve when the shunt is released from the needle;
wherein the deployment mechanism is configured to rotate in a first direction to sequentially push the shunt within the needle and to continue rotation in the first direction to subsequently engage with and retract the needle relative to the housing.

21. The device according to claim 20, wherein the needle is fully disposed within the housing when the shunt is released from the needle.

22. The device according to claim 20, wherein the sleeve comprises a distal contact surface that provides resistance against advancement of the device when the contact surface contacts scleral tissue on an inside of an anterior chamber, the contact surface comprising a protrusion that comprises a flat bottom portion and an angled top portion.

23. The device according to claim 20, wherein the deployment mechanism is configured to rotate about a longitudinal axis of the device in the first direction to sequentially push the shunt within the needle and to continue rotation in the first direction to subsequently retract the needle relative to the housing.

* * * * *